US010907158B2

(12) United States Patent
Greenberg et al.

(10) Patent No.: US 10,907,158 B2
(45) Date of Patent: Feb. 2, 2021

(54) ANTISENSE ANTIBACTERIAL COMPOUNDS AND METHODS

(71) Applicants: Board of Regents, The University of Texas System, Austin, TX (US); Oregon State University, Corvallis, OR (US)

(72) Inventors: David Greenberg, Coppell, TX (US); Bruce L. Geller, Corvallis, OR (US); Erdal Toprak, Plano, TX (US)

(73) Assignees: Board of Regents, The University of Texas System, Austin, TX (US); Oregon State University, Corvallis, OR (US)

( * ) Notice: Subject to any disclaimer, the term of this patent is extended or adjusted under 35 U.S.C. 154(b) by 0 days.

(21) Appl. No.: 16/064,273

(22) PCT Filed: Dec. 22, 2016

(86) PCT No.: PCT/US2016/068373
§ 371 (c)(1),
(2) Date: Jun. 20, 2018

(87) PCT Pub. No.: WO2017/112885
PCT Pub. Date: Jun. 29, 2017

(65) Prior Publication Data
US 2019/0078095 A1     Mar. 14, 2019

Related U.S. Application Data

(60) Provisional application No. 62/433,669, filed on Dec. 13, 2016, provisional application No. 62/408,518, filed on Oct. 14, 2016, provisional application No. 62/301,406, filed on Feb. 29, 2016, provisional application No. 62/387,176, filed on Dec. 23, 2015.

(51) Int. Cl.
| | |
|---|---|
| *C12N 15/113* | (2010.01) |
| *A61K 47/64* | (2017.01) |
| *A61K 31/713* | (2006.01) |
| *A61P 31/04* | (2006.01) |
| *C07K 4/02* | (2006.01) |
| *C07K 14/005* | (2006.01) |
| *C12N 9/12* | (2006.01) |

(52) U.S. Cl.
CPC ........ *C12N 15/1133* (2013.01); *A61K 31/713* (2013.01); *A61K 47/64* (2017.08); *A61P 31/04* (2018.01); *C07K 4/02* (2013.01); *C07K 14/005* (2013.01); *C12N 9/1247* (2013.01); *C12N 15/113* (2013.01); *C12N 2310/11* (2013.01); *C12N 2310/3233* (2013.01)

(58) Field of Classification Search
None
See application file for complete search history.

(56) References Cited

U.S. PATENT DOCUMENTS

| | | | |
|---|---|---|---|
| 5,034,506 A | 7/1991 | Summerton et al. | |
| 5,142,047 A | 8/1992 | Summerton et al. | |
| 5,166,315 A | 11/1992 | Summerton et al. | |
| 5,185,444 A | 2/1993 | Summerton et al. | |
| 5,217,866 A | 6/1993 | Summerton et al. | |
| 5,506,337 A | 4/1996 | Summerton et al. | |
| 5,521,063 A | 5/1996 | Summerton et al. | |
| 5,698,685 A | 12/1997 | Summerton et al. | |
| 6,245,747 B1 | 6/2001 | Porter et al. | |
| 6,965,025 B2 | 11/2005 | Gaarde et al. | |
| 6,969,400 B2 | 11/2005 | Rhee et al. | |
| 7,026,136 B2 * | 4/2006 | Oethinger | A61K 31/085 |
| | | | 435/32 |
| 7,625,873 B2 | 12/2009 | Geller et al. | |
| 7,790,694 B2 | 9/2010 | Geller et al. | |
| 8,067,571 B2 | 11/2011 | Weller et al. | |
| 8,076,476 B2 | 12/2011 | Reeves et al. | |
| 8,299,206 B2 | 10/2012 | Fox et al. | |
| 8,314,072 B2 | 11/2012 | Geller et al. | |
| 8,536,147 B2 | 9/2013 | Weller et al. | |
| 9,249,243 B2 | 2/2016 | Weller et al. | |
| 9,790,495 B2 | 10/2017 | Geller et al. | |
| 2004/0029129 A1 | 2/2004 | Wang et al. | |
| 2005/0288246 A1 | 12/2005 | Iversen et al. | |
| 2006/0241075 A1 | 10/2006 | McSwiggen | |
| 2006/0270621 A1 | 11/2006 | Christiano | |
| 2007/0049542 A1 | 3/2007 | Geller et al. | |
| 2008/0194463 A1 | 8/2008 | Weller et al. | |
| 2010/0016215 A1 | 1/2010 | Moulton et al. | |
| 2010/0234281 A1 | 9/2010 | Weller et al. | |

(Continued)

FOREIGN PATENT DOCUMENTS

| | | |
|---|---|---|
| KR | 10-2013-0005208 | 1/2013 |
| WO | WO 2016/108930 | 7/1916 |

(Continued)

OTHER PUBLICATIONS

GenBank D1251363.1, Jul. 8, 2014.
Greenberg et al., "Antisense phosphorodiamidate morpholino oligomers targeted to an essential gene inhibit Burkholderia cepacia complex," *The Journal of Infectious Diseases*, 201(12):1822-1830, 2010.
Partial Supplementary European Search Report issued in European Application No. 15795398.5, dated Nov. 29, 2017.
PCT International Preliminary Report on Patentability issued in International Application No. PCT/US2016/068373, dated Jun. 26, 2018.

(Continued)

*Primary Examiner* — Tracy Vivlemore
(74) *Attorney, Agent, or Firm* — Parker Highlander PLLC

(57) ABSTRACT

Provided are antisense morpholino oligomers targeted against bacterial virulence factors such as genes that contribute to antibiotic resistance or biofilm formation, or essential genes, and related compositions and methods of using the oligomers and compositions, for instance, in the treatment of an infected mammalian subject.

19 Claims, 21 Drawing Sheets

Specification includes a Sequence Listing.

(56) References Cited

U.S. PATENT DOCUMENTS

| | | | |
|---|---|---|---|
| 2010/0261777 | A1 | 10/2010 | Shaw et al. |
| 2012/0040460 | A1 | 2/2012 | Rigoutsos et al. |
| 2012/0122769 | A1 | 5/2012 | Iversen |
| 2012/0213663 | A1 | 8/2012 | Atieh et al. |
| 2012/0289457 | A1 | 11/2012 | Hanson |
| 2012/0296087 | A1 | 11/2012 | Sinha et al. |
| 2013/0197220 | A1 | 8/2013 | Ueda |
| 2013/0288369 | A1 | 10/2013 | Iversen |
| 2015/0141321 | A1 | 5/2015 | Kole et al. |
| 2015/0361425 | A1 | 12/2015 | Geller et al. |
| 2016/0106857 | A1 | 4/2016 | Geller et al. |
| 2018/0362982 | A1 | 12/2018 | Greenberg et al. |

FOREIGN PATENT DOCUMENTS

| | | |
|---|---|---|
| WO | WO 2017/112885 | 6/1917 |
| WO | WO 2017/112888 | 6/1917 |
| WO | WO 2018/161027 | 9/1918 |
| WO | WO 2019/083823 | 5/1919 |
| WO | WO 1993/001286 | 1/1993 |
| WO | WO 2004/097017 | 11/2004 |
| WO | WO 2006/085973 | 8/2006 |
| WO | WO 2007/009094 | 1/2007 |
| WO | WO 2008/008113 | 1/2008 |
| WO | WO 2009/005793 | 1/2009 |
| WO | WO 2009/064471 | 5/2009 |
| WO | WO 2012/043730 | 4/2012 |
| WO | WO 2012/064991 | 5/2012 |
| WO | WO 2012/150960 | 11/2012 |
| WO | WO 2013/011072 | 1/2013 |
| WO | WO 2015/175977 | 11/2015 |
| WO | WO 2015/179249 | 11/2015 |

OTHER PUBLICATIONS

PCT International Preliminary Report on Patentability issued in International Application No. PCT/US2015/031150, dated Nov. 22, 2016.

PCT International Preliminary Report on Patentability issued in International Application No. PCT/US2015/031213, dated Nov. 22, 2016.

PCT International Preliminary Report on Patentability issued in International Application No. PCT/US2015/000280, dated Jul. 4, 2017.

PCT International Preliminary Report on Patentability issued in International Application No. PCT/US2016/068376, dated Jun. 26, 2018.

PCT International Search Report and Written Opinion issued in International Application No. PCT/US2016/068373, dated May 4, 2017.

PCT International Search Report and Written Opinion issued in International Application No. PCT/US2015/031150, dated Jan. 14, 2016.

PCT International Search Report and Written Opinion issued in International Application No. PCT/US2015/031213, dated Sep. 2, 2015.

PCT International Search Report and Written Opinion issued in International Application No. PCT/US2015/000280, dated May 2, 2016.

PCT International Search Report and Written Opinion issued in International Application No. PCT/US2016/068376, dated Mar. 13, 2017.

Summerton et al., "Morpholino antisense oligomers: design, preparation, and properties," *Antisense and Nucleic Acid Drug Development*, 7(3):187-195, 1997.

Supplementary European Search Report issued in European Application No. 15792493.7, dated Nov. 29, 2017.

Youngblood et al., "Stability of cell-penetrating peptide-morpholino oligomer conjugates in human serum and in cells," *Bioconjugate Chemistry*, 18(1):50-60, 2007.

Confer and Ayalew, "The OmpA family of proteins: roles in bacterial pathogenesis and immunity," *Veterinary Microbiology*, 163:207-222, 2013.

Geller et al., "Morpholino oligomers tested in vitro, in biofilm and in vivo against multidrug-resistant *Klebsiella pneumoniae*," *J Antimicrob Chemother.*, 73:1611-1619, 2018.

Partial Supplementary European Search Report and Provisional Opinion issued in European Application No. 16880104, dated Jul. 19, 2019.

\* cited by examiner

| Strain ID | Species | CsuE-PPMO#21 | SecA-PPMO#24 | OmpA-PPMO#1 | RpoD-PPMO#32 | CsuE-PPMO#22 | PgiL-PPMO#25 | PilU1-PPMO#26 |
|---|---|---|---|---|---|---|---|---|
| ATCC1709 | A. baumannii | | | | | | | |
| H | A. baumannii | | | | | | | |
| M28188 | A. baumannii | | | | | | | |
| H49874 | A. iwoffii | | | | | | | |
| NDM1 | A. baumannii | | | | | | | |
| AB307 | A. baumannii | | | | | | | |
| 17978 | A. baumannii | | | | | | | |
| 19606 | A. baumannii | | | | | | | |
| AYE | A. baumannii | | | | | | | |
| HUMC1 | A. baumannii | | | | | | | |
| ATCC17961 | A. baumannii | | | | | | | |
| AE2013 | A. baumannii | | | | | | | |

Legend: <10%, 25%, 50%, >50%, NT

FIG. 2

ANTISENSE ANTIBACTERIAL COMPOUNDS AND METHODS

CROSS-REFERENCE TO RELATED APPLICATIONS

This application is a national phase application under 35 U.S.C. § 371 of International Application No. PCT/US2016/068373, filed Dec. 22, 2016, which claims the benefit of priority to: U.S. Provisional Application No. 62/387,176, filed Dec. 23, 2015, and U.S. Provisional Application No. 62/301,406, filed Feb. 29, 2016, U.S. Provisional Application No. 62/408,518, filed Oct. 14, 2016, and U.S. Provisional Application No. 62/433,669, filed Dec. 13, 2016, each of which is herein incorporated by reference in its entirety.

STATEMENT REGARDING FEDERALLY SPONSORED RESEARCH

This invention was made with government support under grant number AI098724 awarded by The National Institutes of Health. The government has certain rights in the invention.

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is SATH-007_04WO_SeqList_ST25.txt. The text file is about 33 KB, was created on Dec. 19, 2016, and is being submitted electronically via EFS-Web.

BACKGROUND

Technical Field

The present disclosure relates to antisense morpholino oligomers targeted against bacterial virulence factors such as genes that contribute to antibiotic resistance, biofilm formation or essential processes, and related compositions and methods of using the oligomers and compositions, for instance, in the treatment of an infected mammalian subject.

Description of the Related Art

Currently, there are several types of antibiotic compounds in use against bacterial pathogens and these compounds act through a variety of anti-bacterial mechanisms. For example, beta-lactam antibiotics, such as penicillin and cephalosporin, act to inhibit the final step in peptidoglycan synthesis. Glycopeptide antibiotics, including vancomycin and teichoplanin, inhibit both transglycosylation and transpeptidation of muramyl-pentapeptide, again interfering with peptidoglycan synthesis. Other well-known antibiotics include the quinolones, which inhibit bacterial DNA replication, inhibitors of bacterial RNA polymerase, such as rifampin, and inhibitors of enzymes in the pathway for production of tetrahydrofolate, including the sulfonamides.

Some classes of antibiotics act at the level of protein synthesis. Notable among these are the aminoglycosides, such as kanamycin and gentamicin. This class of compounds targets the bacterial 30S ribosome subunit, preventing the association with the 50S subunit to form functional ribosomes. Tetracyclines, another important class of antibiotics, also target the 30S ribosome subunit, acting by preventing alignment of aminoacylated tRNA's with the corresponding mRNA codon. Macrolides and lincosamides, another class of antibiotics, inhibit bacterial synthesis by binding to the 50S ribosome subunit, and inhibiting peptide elongation or preventing ribosome translocation.

Despite impressive successes in controlling or eliminating bacterial infections by antibiotics, the widespread use of antibiotics both in human medicine and as a feed supplement in poultry and livestock production has led to drug resistance in many pathogenic bacteria. Antibiotic resistance mechanisms can take a variety of forms. One of the major mechanisms of resistance to beta lactams, particularly in Gram-negative bacteria, is the enzyme beta-lactamase, which renders the antibiotic inactive by cleaving the lactam ring. Likewise, resistance to aminoglycosides often involves an enzyme capable of inactivating the antibiotic, in this case by adding a phosphoryl, adenyl, or acetyl group. Active efflux of antibiotics is another way that many bacteria develop resistance. Genes encoding efflux proteins, such as the tetA, tetG, tetL, and tetK genes for tetracycline efflux, have been identified. A bacterial target may develop resistance by altering the target of the drug. For example, the so-called penicillin binding proteins (PBPs) in many beta-lactam resistant bacteria are altered to inhibit the critical antibiotic binding to the target protein. Resistance to tetracycline may involve, in addition to enhanced efflux, the appearance of cytoplasmic proteins capable of competing with ribosomes for binding to the antibiotic. For those antibiotics that act by inhibiting a bacterial enzyme, such as for sulfonamides, point mutations in the target enzyme may confer resistance.

Biofilm formation can also lead to antibiotic resistance, among other clinical difficulties. Typically, in situations where bacteria form a biofilm within an infected host, the infection turns out to be untreatable and can develop into a chronic state. Hallmarks of chronic biofilm-based infections not only include resistance to antibiotic treatments and many other conventional antimicrobial agents but also a capacity for evading host defenses. Therefore, strategies that prevent or breakdown biofilm would be of therapeutic interest and benefit.

The appearance of antibiotic resistance in many pathogenic bacteria, including cases involving multi-drug resistance (MDR), raises the fear of a post-antibiotic era in which many bacterial pathogens were simply untreatable by medical intervention. Thus, there is a need for antimicrobial agents that (i) are not subject to the principal types of antibiotic resistance currently hampering antibiotic treatment of bacterial infection, (ii) can be developed rapidly and with some reasonable degree of predictability as to target-bacteria specificity, (iii) are effective at low doses, and (iv) show few side effects.

SUMMARY

Embodiments of the present disclosure relate, in part, to the discovery that the antisense targeting of bacterial virulence factors can, inter alia, increase the antibiotic susceptibility of otherwise antibiotic-resistant pathogenic bacteria, and reduce the ability of certain pathogenic bacteria to form and maintain difficult-to-treat biofilms. For example, the antisense targeting of antibiotic resistance genes such as carbapenemases and efflux pumps was shown to increase the susceptibility of antibiotic resistant (e.g., multi-drug resistant) bacteria to many commonly used antibiotics, and could thus find utility in the treatment of such bacteria, for instance, in combination with antibiotics. Also, the antisense targeting of genes associated with biofilm formation was shown to break down existing biofilms and reduce the production of new biofilms. Such antisense targeting could find utility in standalone therapies against biofilm-forming bacteria, and as combination therapies, for example, to increase the susceptibility of biofilm-forming bacteria to antibiotics.

Embodiments of the present disclosure therefore include a substantially uncharged antisense morpholino oligomer, composed of morpholino subunits and phosphorus-containing intersubunit linkages joining a morpholino nitrogen of one subunit to a 5'-exocyclic carbon of an adjacent subunit, and having (a) about 10-40 nucleotide bases, and (b) a targeting sequence of sufficient length and complementarity to specifically hybridize to a bacterial mRNA target sequence that encodes a virulence factor; where the oligomer is conjugated to a cell-penetrating peptide (CPP).

In certain embodiments, the target sequence comprises a translational start codon of the bacterial mRNA and/or a sequence within about 30 bases upstream or downstream of the translational start codon of the bacterial mRNA.

In some embodiments, the virulence factor is an antibiotic resistance protein or a biofilm formation protein. In some embodiments, the virulence factor is an essential protein.

In certain embodiments, the antibiotic resistance protein is selected from one or more of New Delhi metallo-beta-lactamase (NDM-1), serine beta-lactamase (KPC), acridine resistance complex protein AcrA, acridine resistance complex protein AcrB, acridine resistance complex repressor protein AcrR, acridine resistance complex protein TolC, and outer membrane protein A (OmpA). In specific embodiments, the target sequence is selected from Table 1A. Some antisense oligomers comprise, consist, or consist essentially of a targeting sequence set forth in Table 2A, a fragment of at least 10 contiguous nucleotides of a targeting sequence in Table 2A, or variant having at least 80% sequence identity to a targeting sequence in Table 2A.

In some embodiments, the biofilm formation protein is encoded by one or more of cepl, suhB, CsuE, SecA, Pg1L, PilU1, AlgZ, AlgU, LasR, FleR and PelF. In particular embodiments, the target sequence is selected from Table 1B. Some antisense oligomers comprise, consist, or consist essentially of a targeting sequence set forth in Table 2B, a fragment of at least 10 contiguous nucleotides of a targeting sequence in Table 2B, or variant having at least 80% sequence identity to a targeting sequence in Table 2B.

In some embodiments, the essential protein is an RNA polymerase encoded by one or more of RpoD. In some embodiments, the essential protein is a DNA polymerase II encoded by one or more of PolB. Some antisense oligomers comprise, consist, or consist essentially of a targeting sequence set forth in Table 2C, a fragment of at least 10 contiguous nucleotides of a targeting sequence in Table 2C, or variant having at least 80% sequence identity to a targeting sequence in Table 2C.

In certain embodiments, an antisense morpholino oligomer of the disclosure may be of formula (I):

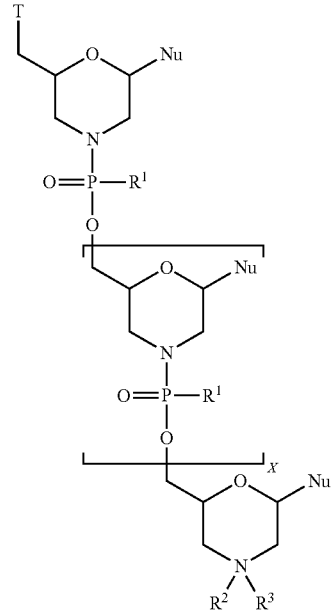

(I)

or a pharmaceutically acceptable salt thereof, where each Nu is a nucleobase which taken together forms a targeting sequence;

X is an integer from 9 to 38;

T is selected from OH and a moiety of the formula:

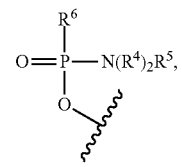

where each $R^4$ is independently $C_1$-$C_6$ alkyl, and $R^5$ is selected from an electron pair and H, and $R^6$ is selected from OH, —N($R^7$)$CH_2C(O)NH_2$, and a moiety of the formula:

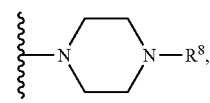

where:

$R^7$ is selected from H and $C_1$-$C_6$ alkyl, and $R^8$ is selected from G, —C(O)—$R^9$OH, acyl, trityl, and 4-methoxytrityl, where:

$R^9$ is of the formula —(O-alkyl)$_y$- wherein y is an integer from 3 to 10 and each of the y alkyl groups is independently selected from $C_2$-$C_6$ alkyl;

each instance of $R^1$ is —N($R^{10}$)$_2R^{11}$ wherein each $R^{10}$ is independently $C_1$-$C_6$ alkyl, and $R^{11}$ is selected from an electron pair and H;

$R^2$ is selected from H, G, acyl, trityl, 4-methoxytrityl, benzoyl, stearoyl, and a moiety of the formula:

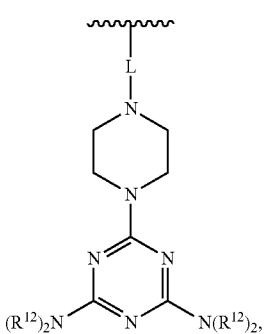

where L is selected from —C(O)(CH$_2$)$_6$C(O)— and —C(O)(CH$_2$)$_2$S$_2$(CH$_2$)$_2$C(O)—, and each R$^{12}$ is of the formula —(CH$_2$)$_2$OC(O)N(R$^{14}$)$_2$ wherein each R$^{14}$ is of the formula —(CH$_2$)$_6$NHC(=NH)NH$_2$; and R$^3$ is selected from an electron pair, H, and C$_1$-C$_6$ alkyl, wherein G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, and —C(O)CH$_2$NH—CPP, or G is of the formula:

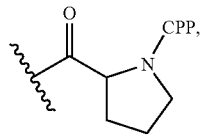

wherein the CPP is attached to the linker moiety by an amide bond at the CPP carboxy terminus, with the proviso that only one instance of G is present, wherein the targeting sequence specifically hybridizes to a bacterial mRNA target sequence that encodes a virulence factor.

In certain embodiments, the CPP is an arginine-rich peptide. In certain embodiments, the CPP is selected from Table C1.

Also included are methods of reducing expression and activity of a virulence factor in a bacteria or bacterium, comprising contacting the bacteria or bacterium with an antisense oligomer described herein.

In some embodiments, the bacterium is in a subject, and the method comprises administering the antisense oligomer to the subject.

In certain embodiments, the bacterium is selected from the genus *Escherichia, Acinetobacter, Klebsiella*, and *Burkholderia*. In certain embodiments, the bacterium is *Escherichia coli, Acinetobacter baumannii, Klebsiella pneumoniae*, or *Burkholderia cepacia* (complex). In certain embodiments, the bacterium is *Escherichia coli, Acinetobacter baumannii*, or *Klebsiella pneumoniae*, and where the virulence factor is an antibiotic resistance protein selected from one or more of NDM-1 and AdeA.

In some embodiments, the bacterium is *Burkholderia cepacia* (complex) and where the virulence factor is a biofilm formation protein encoded by one or more of cepI and suhB. In certain embodiments, the *Burkholderia cepacia* (complex) comprises one or more of *Burkholderia cenocepacia, Burkholderia multivorans, Burkholderia vietnamiensis, Burkholderia stabilis, Burkholderia anthina, Burkholderia pyrrocinia, Burkholderia dolosa*, and/or *Burkholderia ambifaria*. In certain embodiments, administration of the antisense oligomer reduces biofilm formation or existing biofilm by at least about 10%. In certain embodiments, the subject is immunocompromised and has an underlying lung disease. In specific embodiments, the subject has cystic fibrosis (CF) or chronic granulomatous disease (CGD).

In some embodiments, the bacterium is *Acinetobacter baumannii* and where the virulence factor is a chaperone-usher pili assembly system protein encoded by one or more of CsuE. In some embodiments, the bacterium is *Acinetobacter baumannii* and where the virulence factor is a chaperone-usher pili assembly system protein encoded by one or more of CsuE. In some embodiments, the bacterium is *Acinetobacter baumannii* and where the virulence factor is an ATPase associated with cell membrane transport encoded by one or more of SecA. In some embodiments, the bacterium is *Acinetobacter baumannii* and where the virulence factor is encoded by one or more of PglL. In some embodiments, the bacterium is *Acinetobacter baumannii* and where the virulence factor is encoded by one or more of PilU1. In some embodiments, the bacterium is *Pseudomonas aeruginosa* and where the virulence factor is a protein associated with alginate biosynthesis encoded by one or more of AlgZ. In some embodiments, the bacterium is *Pseudomonas aeruginosa* and where the virulence factor is a protein associated with alginate biosynthesis encoded by one or more of AlgU. In some embodiments, the bacterium is *Pseudomonas aeruginosa* and where the virulence factor is a transcriptional activator protein encoded by one or more of LasR. In some embodiments, the bacterium is *Pseudomonas aeruginosa* and where the virulence factor is a transcriptional regulator of flagella expression encoded by one or more of FleR. In some embodiments, the bacterium is *Pseudomonas aeruginosa* and where the virulence factor is a polysaccharide biosynthesis protein encoded by one or more of PelF. In certain embodiments, administration of the antisense oligomer reduces biofilm formation or existing biofilm by at least about 10%.

Some methods include administering the oligomer separately or concurrently with an antimicrobial agent, for example, where administration of the oligomer increases susceptibility of the bacterium to the antimicrobial agent. Some methods include administering the oligomer by aerosolization.

In certain embodiments, the bacterium is *Escherichia coli, Acinetobacter baumannii*, or *Klebsiella pneumoniae*, the virulence factor is NDM-1, and the antimicrobial agent is a carbapenem. In certain embodiments, the carbapenem is selected from one or more of meropenem, imipenem, ertapenem, doripenem, panipenem, biapenem, razupenem, tebipenem, lenapenem, and tomopenem.

In certain embodiments, the bacterium is *Escherichia coli, Acinetobacter baumannii*, or *Klebsiella pneumoniae*, the virulence factor is KPC or KPC 1-4, and the antimicrobial agent is a carbapenem. In certain embodiments, the carbapenem is selected from one or more of meropenem, imipenem, ertapenem, doripenem, panipenem, biapenem, razupenem, tebipenem, lenapenem, and tomopenem.

In some embodiments, the bacterium is *Escherichia coli, Acinetobacter baumannii*, or *Klebsiella pneumoniae*, the virulence factor is AdeA, and the antimicrobial agent is selected from one or more of aminoglycoside antibiotics, tetracycline antibiotics, and β-lactam antibiotics. In certain embodiments, the aminoglycoside is selected from one or more of tobramycin, gentamicin, kanamycin a, amikacin, dibekacin, sisomicin, netilmicin, neomycin B, neomycin C, neomycin E (paromomycin), and streptomycin. In certain embodiments, the tetracycline antibiotic is selected from one or more of tetracycline, chlortetracycline, oxytetracycline, demeclocycline, lymecycline, meclocycline, methacycline, minocycline, rolitetracycline, and doxycyline. In certain embodiments, the β-lactam antibiotic is selected from one or more of carbapenems, penicillin derivatives (penams), cephalosporins (cephems), and monobactams.

In certain embodiments, the bacterium is *Escherichia coli*, *Acinetobacter baumannii*, or *Klebsiella pneumoniae*, the virulence factor is an acridine resistance complex protein encoded by one or more of AcrA, AcrB, AcrR, and TolC, and the antimicrobial agent can be any antibiotic. In another embodiment, the antimicrobial agent is selected from one or more of Clindamycin, Piperacillin-tazobactam, Doxycycline, Chloramphenicol, Fusidic acid, Oxacillin, Erythromycin and/or Trimethoprim.

In certain embodiments, the bacterium is *Escherichia coli*, *Acinetobacter baumannii*, or *Klebsiella pneumoniae*, the virulence factor is an outer membrane protein A encoded by one or more of OmpA, and the antimicrobial agent can be any antibiotic. In another embodiment, the antimicrobial agent is selected from one or more of Clindamycin, Piperacillin-tazobactam, Doxycycline, Chloramphenicol, Fusidic acid, Oxacillin, Erythromycin and/or Trimethoprim.

In certain embodiments, the bacterium is *Burkholderia cepacia* (complex), the virulence factor is a biofilm formation protein encoded by one or more of cepI or suhB, and the antimicrobial agent is selected from one or more of ceftazidime, doxycycline, piperacillin, meropenem, chloramphenicol, and co-trimoxazole (trimethoprim/sulfamethoxazole).

In certain embodiments, the bacterium is *Acinetobacter baumannii*, the virulence factor is a biofilm formation protein encoded by one or more of CsuE, SecA, Pg1L and PilU1, and the antimicrobial agent is selected from one or more of ceftazidime, minocycline, doxycycline, piperacillin, meropenem, chloramphenicol, and co-trimoxazole (trimethoprim/sulfamethoxazole).

In certain embodiments, the bacterium is *Pseudomonas aeruginosa*, the virulence factor is a biofilm formation protein encoded by one or more of AlgZ, AlgU, LasR, FleR and PelF, and the antimicrobial agent is selected from one or more of ceftazidime, minocycline, doxycycline, piperacillin, meropenem, chloramphenicol, and co-trimoxazole (trimethoprim/sulfamethoxazole).

In certain embodiments, the bacterium is *Acinetobacter baumannii*, the virulence factor is an essential protein encoded by one or more of RpoD, and the antimicrobial agent is selected from one or more of ceftazidime, minocycline, doxycycline, piperacillin, meropenem, chloramphenicol, and co-trimoxazole (trimethoprim/sulfamethoxazole).

In certain embodiments, the bacterium is *Pseudomonas aeruginosa*, the virulence factor is an essential protein encoded by one or more of PolB, and the antimicrobial agent is selected from one or more of ceftazidime, minocycline, doxycycline, piperacillin, meropenem, chloramphenicol, and co-trimoxazole (trimethoprim/sulfamethoxazole).

In some embodiments, the oligomer reduces the minimum inhibitory concentration (MIC) of the antimicrobial agent against the bacterium by at least about 10% relative to the antimicrobial agent alone. In certain embodiments, the oligomer increases the susceptibility of the bacterium to the antimicrobial agent by at least about 10% relative to the antimicrobial agent alone.

Also included are pharmaceutical compositions, comprising an antisense oligomer described herein and a pharmaceutically-acceptable carrier. Certain pharmaceutical compositions can further comprise one or more antimicrobial agents.

BRIEF DESCRIPTION OF THE FIGURES

FIGS. 1F-1H show exemplary peptide PMO conjugates structures used in the exemplary PPMOs.

FIG. 2 shows that PPMOs prevent formation of biofilm in *Acinetobacter* spp. *A. baumannii* or *A. iwoffii* strains were grown on MSEC biofilm plates for 20 hours in the presence or absence of PPMOs. Crystal violet staining of the pegs was performed and the amount of biofilm present was measured at OD570. The heat map displays percentage of biofilm reduction compared to no treatment controls at a PPMO concentration of 8 µM. CsuE-PPMO#21 showed a >50% reduction in biofilm in 10/12 (83%) of strains tested.

(FIG. 7A) The MIC of meropenem was measured in various concentrations of NDM-1 PPMO#18. (FIG. 7B) Viable cells were measured before (0 hr) or after growth of strain BAA-2149 for 24 hr with meropenem and/or NDM-1 PPMO#19.

(FIG. 9*a*) Infection and treatment schedule. (FIG. 9*b*) Survival of mice was recorded, (FIG. 9*c*) Body temperatures were monitored, (FIG. 9*d*) Level of bacteremia was measured 6 h post-infection, (FIG. 9*e*) Survival of mice treated with meropenem (1 mg) and various amounts of NDM-1 PPMO (33.3 μg (n=13), 11.1 μg (n=11), 3.7 μg (n=11)), Ser PPMO (33.3 μg (n=10)), or meropenem only (n=10). (FIG. 9*f*, FIG. 9*g*) Body temperature and bacteria in the blood (6 h post-infection) were monitored. (FIG. 9*h*) Survival of mice treated at the time of infection (n=7), 0.5 h post-infection (n=8), or 1 h post-infection (n=7), with meropenem (1 mg) and PPMO (250 μg). Mice treated with meropenem and Ser PPMO at the time of infection (n=7) and mice treated with PBS (n=7) were used as negative controls. For Kaplan-Meyer survival curves, *$p<0.001$ $p<0.01$ *$p<0.05$ by log-rank (Mantel-Cox) test. For other graphs, data represented as the mean±SEM, *$p<0.001$ $p<0.01$ *$p<0.05$ by two-tailed Mann-Whitney U test.

FIG. 13A: AcrA expression in *E. coli* cells in increasing concentrations of acrA-PPMO was quantified using an anti-AcrA antibody (top panel). AcrA expression was normalized against the expression of cAMP receptor protein (CRP). AcrA translation was ~30 times lower when *E. coli* cells were treated with 3 μM or higher concentrations of acrA-PPMO (middle panel). No AcrA expression was detected when the acrA gene was deleted in *E. coli*. Error bars represent the standard deviations of normalized AcrA expression in six experimental replicates. Consistent with the reduced AcrA translation in increasing concentrations of acrA-PPMO, growth rates of *E. coli* in fixed concentrations of clindamycin gradually decreased in increasing concentrations of acrA-PPMO (bottom panel).

FIG. 13B: Sample antibiotic dose response curves of *E. coli* cells in the absence of acrA-PPMO (open circles), in the presence of 10 μM acrA-PPMO (squares), in the presence of 10 μM scrambled PPMO (filed circles), and *E. coli* cells with acrA deletion (triangles).

FIG. 13C: Histogram of the measured fold changes in MIC values for the *E. coli* cells in the absence of acrA-PPMO (left), *E. coli* cells in the presence of 10 μM acrA-PPMO (right), and *E. coli* cells with the acrA deletion (center).

FIG. 13D: Killing of *E. coli* BW25113, *Klebsiella pneumoniae* F45153 (clinical urine isolate) and *Burkholderia cenocepacia* complex K56-2 (cystic fibrosis clinical isolate) by Piperacillin-Tazobactam alone (black circles) or in combination with 10 μM scrambled PPMO (grey circles), or acrA-PPMO (squares) after 18 hour incubation. The horizontal dashed line represents the inoculum ($5\times10^5$ CFU mL$^{-1}$) prior to 18-hour incubation. The x-axis represents the normalized concentration of Piperacillin-Tazobactam in MIC units. The bacteria were grown overnight in cation-adjusted Mueller-Hinton II broth (MHII, Becton, Dickinson and Co., Sparks, Md.) at 37° C, 220 rpm. Cultures were diluted to $5\times10^5$ CFU mL$^{-1}$ in fresh MHII and incubated with serial 2-fold dilutions of Piperacillin/Tazobactam (Pip/Tazo) alone or in combination with 10 μM Ser PPMO or AcrA PPMO#3 in a 96-well plate and incubated for 18 h at 37° C., 220 rpm. Growth controls included H$_2$O, 10 μM Ser PPMO, and 10 μM AcrA PPMO#3 alone. The minimum inhibitory concentration (MIC) was defined as the Pip/Tazo concentration at which no visible growth was detected at 18 h; for reference, the MIC values were 4, 2, and 64 μg mL$^{-1}$ for *E. coli* BW25113, *K. pneumoniae* F45153, and *B. cenocepacia* K56-2, respectively. Growth controls and wells at 1-, 0.5-, and 0.25-fold the MIC of Pip/Tazo alone or in combination were serially diluted in PBS and plated on trypticase soy agar+5% sheep blood (Remel, Lenexa, Kans.) for CFU enumeration. Experiments were repeated in triplicate.

FIG. 13E: HBEC3KT human cells were incubated in increasing doses of acrA-PPMO and number of viable cells was counted (Cell-Titer-Glo, Promega) every 24 hours. No significant toxicity was detected due to the use of acrA-PPMO.

FIG. 14A: Minimum inhibitory concentrations measured in two-dimensional gradients of (left) trimethoprim and sulfamethoxazole and (right) trimethoprim and piperacillin-tazobactam; for the wild type *E. coli* cells (circle), for the wild type *E. coli* cells in the presence of 10 μM acrA-PPMO (square), and *E. coli* cells with acrA deletion (triangle).

FIG. 14B: Area under the MIC curves shown in FIG. 13A for the wild type *E. coli* cells (left bars), for the wild type *E. coli* cells in the presence of 10 μM acrA-PPMO (right bars), and *E. coli* cells with acrA deletion (center bars).

DETAILED DESCRIPTION

Definitions

Figure 1C:
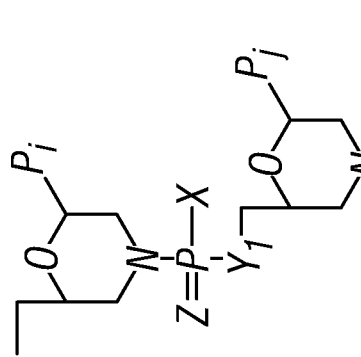
FIGS. 1B-1E show the repeating subunit segment of exemplary morpholino oligomers, designated B through E.
Figure 1E:
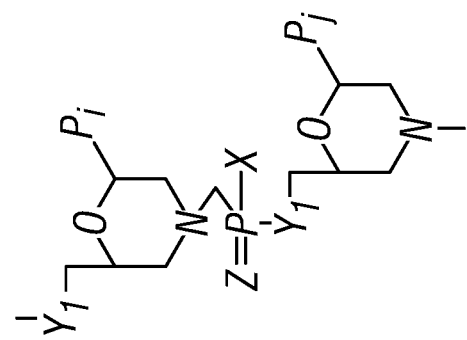
Figure 1B:
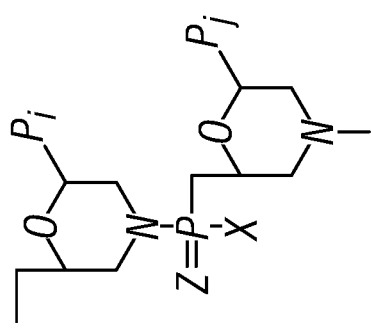
Figure 1D:
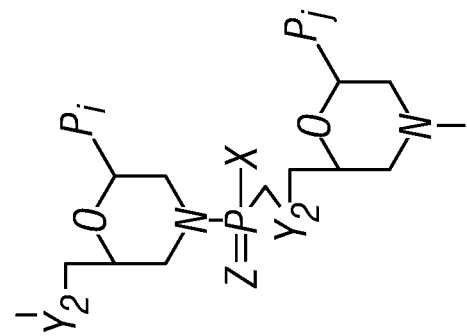

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight, or length that varies by as much as 30, 25, 20, 15, 10, 9, 8, 7, 6, 5, 4, 3, 2 or 1% to a reference quantity, level, value, number, frequency, percentage, dimension, size, amount, weight, or length.

By "coding sequence" is meant any nucleic acid sequence that contributes to the code for the polypeptide product of a gene. By contrast, the term "non-coding sequence" refers to any nucleic acid sequence that does not directly contribute to the code for the polypeptide product of a gene.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

As used herein, the terms "contacting a cell", "introducing" or "delivering" include delivery of the oligomers of this disclosure into a cell by methods routine in the art, e.g., transfection (e.g., liposome, calcium-phosphate, polyethyleneimine), electroporation (e.g., nudeofection), microinjection), transformation, and administration.

The terms "cell penetrating peptide" (CPP) or "a peptide moiety which enhances cellular uptake" are used interchangeably and refer to cationic cell penetrating peptides, also called "transport peptides", "carrier peptides", or "peptide transduction domains". In some aspects, the peptides have the capability of inducing cell penetration within about or at least about 30%, 40%, 50%, 60%, 70%, 80%, 90%, or 100% of cells of a given population and/or allow macromolecular translocation to or within multiple tissues in vivo upon systemic administration. Particular examples of CPPs include "arginine-rich peptides." CPPs are well-known in the art and are disclosed, for example, in U.S. Application No. 2010/0016215, which is incorporated by reference in its entirety.

"An electron pair" refers to a valence pair of electrons that are not bonded or shared with other atoms.

"Homology" refers to the percentage number of amino acids that are identical or constitute conservative substitutions. Homology may be determined using sequence comparison programs such as GAP (Deveraux et al., 1984, Nucleic Acids Research 12, 387-395) or BLAST. In this way sequences of a similar or substantially different length to those cited herein could be compared by insertion of gaps into the alignment, such gaps being determined, for example, by the comparison algorithm used by GAP.

By "isolated" is meant material that is substantially or essentially free from components that normally accompany it in its native state. For example, an "isolated polynucleotide" or "isolated oligomer," as used herein, may refer to a polynucleotide that has been purified or removed from the sequences that flank it in a naturally-occurring state, e.g., a DNA fragment that is removed from the sequences that are adjacent to the fragment in the genome. The term "isolating" as it relates to cells refers to the purification of cells (e.g., fibroblasts, lymphoblasts) from a source subject (e.g., a subject with a polynucleotide repeat disease). In the context of mRNA or protein, "isolating" refers to the recovery of mRNA or protein from a source, e.g., cells.

The term "modulate" includes to "increase" or "decrease" one or more quantifiable parameters, optionally by a defined and/or statistically significant amount. By "increase" or "increasing," "enhance" or "enhancing," or "stimulate" or "stimulating," refers generally to the ability of one or antisense compounds or compositions to produce or cause a greater physiological response (i.e., downstream effects) in a cell or a subject relative to the response caused by either no antisense compound or a control compound. Relevant physiological or cellular responses (in vivo or in vitro) will be apparent to persons skilled in the art. An "increased" or "enhanced" amount is typically a "statistically significant" amount, and may include an increase that is 1.1, 1.2, 2, 3, 4, 5, 6, 7, 8, 9, 10, 15, 20, 30, 40, 50 or more times (e.g., 500, 1000 times) (including all integers and ranges between and above 1), e.g., 1.5, 1.6, 1.7, 1.8) the amount produced by no antisense compound (the absence of an agent) or a control compound. The term "reduce" or "inhibit" may relate generally to the ability of one or more antisense compounds or compositions to "decrease" a relevant physiological or cellular response, such as a symptom of a disease or condition described herein, as measured according to routine techniques in the diagnostic art. Relevant physiological or cellular responses (in vivo or in vitro) will be apparent to persons skilled in the art, and may include reductions in bacterial cell growth, reductions in the minimum inhibitory concentration (MIC) of an antimicrobial agent, and others. A "decrease" in a response may be "statistically significant" as compared to the response produced by no antisense compound or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers and ranges in between.

As used herein, an "antisense oligomer," "oligomer" or "oligomer" refers to a linear sequence of nucleotides, or nucleotide analogs, which allows the nucleobase (for example a purine or pyrimidine base-pairing moiety) to hybridize to a target sequence in an RNA by Watson-Crick base pairing, to form an oligomer:RNA heteroduplex within the target sequence. The terms "antisense oligomer", "antisense oligomer", "oligomer" and "compound" may be used interchangeably to refer to an oligomer. The cyclic subunits may be based on ribose or another pentose sugar or, in certain embodiments, a morpholino group (see description of morpholino oligomers below).

The term "oligomer," "oligomer," or "antisense oligomer" also encompasses an oligomer having one or more additional moieties conjugated to the oligomer, e.g., at its 3'- or 5'-end, such as a polyethylene glycol moiety or other hydrophilic polymer, e.g., one having 10-100 monomeric subunits, which may be useful in enhancing solubility, or a moiety such as a lipid or peptide moiety that is effective to enhance the uptake of the compound into target bacterial cells and/or enhance the activity of the compound within the cell, e.g., enhance its binding to a target polynucleotide.

A "nuclease-resistant" oligomers refers to one whose backbone is substantially resistant to nuclease cleavage, in non-hybridized or hybridized form; by common extracellular and intracellular nucleases in the body or in a bacterial cell (for example, by exonucleases such as 3'-exonucleases, endonucleases, RNase H); that is, the oligomer shows little or no nuclease cleavage under normal nuclease conditions to which the oligomer is exposed. A "nuclease-resistant heteroduplex" refers to a heteroduplex formed by the binding of an antisense oligomer to its complementary target, such that the heteroduplex is substantially resistant to in vivo degradation by intracellular and extracellular nucleases, which are capable of cutting double-stranded RNA/RNA or RNA/DNA complexes. A "heteroduplex" refers to a duplex between an antisense oligomer and the complementary portion of a target RNA.

As used herein, "nucleobase" (Nu), "base pairing moiety" or "base" are used interchangeably to refer to a purine or pyrimidine base found in native DNA or RNA (uracil, thymine, adenine, cytosine, and guanine), as well as analogs of the naturally occurring purines and pyrimidines, that confer improved properties, such as binding affinity to the oligomer. Exemplary analogs include hypoxanthine (the base component of the nucleoside inosine); 2,6-diaminopurine; 5-methyl cytosine; C5-propynyl-modified pyrimidines; 9-(aminoethoxy)phenoxazine (G-clamp) and the like.

A nucleobase covalently linked to a ribose, sugar analog or morpholino comprises a nucleoside. "Nucleotides" are composed of a nucleoside together with one phosphate group. The phosphate groups covalently link adjacent nucleotides to one another to form an oligomer.

An oligomer "specifically hybridizes" to a target sequence if the oligomer hybridizes to the target under physiological conditions, with a Tm substantially greater than 40° C. or 45° C., preferably at least 50° C., and typically 60° C.-80° C. or higher. Such hybridization preferably corresponds to stringent hybridization conditions. At a given ionic strength and pH, the Tm is the temperature at which 50% of a target sequence hybridizes to a complementary polynucleotide. Such hybridization may occur with "near" or "substantial" complementarity of the antisense oligomer to the target sequence, as well as with exact complementarity.

As used herein, "sufficient length" includes an antisense oligomer that is complementary to at least about 8, more typically about 8-10, 8-11, 8-12, 8-13, 8-14, 8-15, 8-16, 8-17, 8-18, 8-19, 8-20, 8-30, 8-40, or 10-11, 10-12, 10-13, 10-14, 10-15, 10-16, 10-17, 10-18, 10-19, 10-20, 10-30, 10-40 (including all integers and ranges in between) contiguous or non-contiguous nucleobases in a region of a bacterial mRNA target sequence. An antisense oligomer of sufficient length has at least a minimal number of nucleotides to be capable of specifically hybridizing to a region of the bacterial mRNA target. In some embodiments, an oligomer of sufficient length is from 10 to 40 or 10 to 30 nucleotides in length, for example, about 10-11, 10-12, 10-13, 10-14, 10-15, 10-16, 10-17, 10-18, 10-19, 10-20, 10-25, 10-28, 10-30, 10-40, 11-12, 11-13, 11-14, 11-15, 11-16, 11-17, 11-18, 11-19, 11-20, 11-25, 11-28, 11-30, or 11-40 nucleotides in length, or about 10, 11, 12, 13, 14, 15, 16, 17, 18, 19, 20, 21, 22, 23, 24, 25, 26 27, 28, 29, 30, 31, 32, 33, 34, 35, 36, 37, 38, 39, or 40 nucleotides in length.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., Nucl. Acids Res. 25:3389, 1997.

A "subject" or a "subject in need thereof" includes a mammalian subject such as a human subject.

The terms "TEG," "EG3," or "triethylene glycol tail" refer to triethylene glycol moieties conjugated to the oligomer, e.g., at its 3'- or 5'-end. For example, in some embodiments, "TEG" includes, for example, wherein T of the compound of formula (I), (II), or (III) is of the formula:

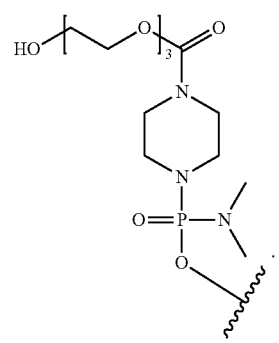

The term "pip-PDA" refers to a 5' terminal piperazine-phosphorodiamidate moiety that connects a G group, where the G group comprises a cell-penetrating peptide (CPP) and linker moiety further discussed below, to the 5' end of the oligomer by way of an amide bond between the G group linker and the piperazinyl nitrogen. For example, in some embodiments, "pip-PDA" includes wherein T of the compound of formula (I) or (II) is of the formula:

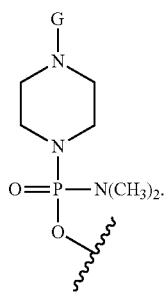

The term "target sequence" refers to a portion of the target RNA, for example, a bacterial mRNA, against which the antisense oligomer is directed, that is, the sequence to which the oligomer will hybridize by Watson-Crick base pairing of a complementary sequence. In certain embodiments, the target sequence may be a contiguous region of the translation initiation region of a bacterial gene.

The "translational start codon region" refers to a region that is 30 bases upstream or downstream of a translation initiation codon of a gene.

The term "targeting sequence" or "antisense targeting sequence" refers to the sequence in an oligomer that is complementary or substantially complementary to the target sequence in the RNA, e.g., the bacterial mRNA. The entire sequence, or only a portion, of the antisense compound may be complementary to the target sequence. For example, in an oligomer of about 10-30 bases, about 6, 7, 8, 9, 10, 11, 12, 13, 14, 15, 16, 17, 18, 19, 20, 21, 22, 23, 24, 25, 26, 27, 28, or 29 of the bases may be targeting sequences that are complementary to the target region. Typically, the targeting sequence is formed of contiguous bases, but may alternatively be formed of non-contiguous sequences that when placed together, e.g., from opposite ends of the oligomer, constitute sequence that spans the target sequence.

A "targeting sequence" may have "near" or "substantial" complementarity to the target sequence and still function for the purpose of the present disclosure, that is, still be "complementary." Preferably, the oligomer analog compounds employed in the present disclosure have at most one mismatch with the target sequence out of 10 nucleotides, and preferably at most one mismatch out of 20. Alternatively, the antisense oligomers employed have at least 90% sequence homology, and preferably at least 95% sequence homology, with the exemplary targeting sequences as designated herein.

As used herein, the term "quantifying", "quantification" or other related words refer to determining the quantity, mass, or concentration in a unit volume, of a nucleic acid, polynucleotide, oligomer, peptide, polypeptide, or protein.

As used herein, "treatment" of a subject (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

Sequences for Targeting Bacterial Virulence Factors

Certain embodiments relate to antisense oligomers, and related compositions and methods, which are of sufficient length and complementarity to specifically hybridize to a bacterial mRNA target sequence that encodes a virulence factor. General examples of virulence factors include antibiotic resistance genes, biofilm formation genes and their encoded proteins. In addition, virulence factors include genes that encode regulatory proteins that control the expression (transcription and/or translation) of other genes which provide a benefit to the bacterium during the process of infection.

In certain embodiments, the target sequence contains all or a portion (e.g., 1 or 2 nucleotides) of a translational start codon of the bacterial mRNA. In some embodiments, the target sequence contains a sequence that is about or within about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 bases upstream or downstream of a translational start codon (e.g., ATG; AUG) of the bacterial mRNA target sequence. For example, in particular embodiments, the 5'-end of the target sequence is the adenine, uracil, or guanine nucleotide in a translational start codon of the bacterial mRNA. In some embodiments, the 5'-end or 3'-end of the target sequence begins at residue 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 downstream of the last nucleotide (e.g., guanine) of a translational start codon of the bacterial mRNA. In some embodiments, the 5'-end or 3'-end of the target sequence begins at residue 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 upstream of the first nucleotide (e.g., adenine) of a translational start codon of the bacterial mRNA In some embodiments, the virulence factor is an antibiotic resistance gene or its encoded protein, i.e., a gene or protein that is associated with resistance of the bacteria to at least one antimicrobial agent. General examples of antibiotic resistance genes include beta-lactamases, which can enzymatically deactivate certain antimicrobial agents, and proteins that increase the permeability or active efflux (pumping-out) of an antimicrobial agent. Particular examples of antibiotic resistance genes include New Delhi metallo-beta-lactamase (NDM-1), resistance-nodulation-cell division (RND)-type multidrug efflux pump subunit AdeA (adeA), serine beta-lactamase (KPC or KPC 1-4), acridine resistance complex protein AcrA, acridine resistance complex protein AcrB, acridine resistance complex repressor protein AcrR, acridine resistance complex protein TolC, and outer membrane protein A (OmpA). Exemplary translational start codon region sequences of the NDM-1 and AdeA resistance genes are provided in Table 1A below.

In some embodiments, the virulence factor is a biofilm formation gene or its encoded protein, i.e., a gene or protein that is associated with or contributes to the formation of biofilm. A biofilm can include any group of bacterial cells that adhere to each other on a surface, for example, a tissue surface or a surface of an implanted medical device. Such adherent cells are often embedded within a self-produced matrix of extracellular polymeric substance (EPS), a polymeric mixture composed, for example, of extracellular DNA, proteins, and polysaccharides. Bacteria form a biofilm in response to many factors, which may include cellular recognition of specific or non-specific attachment sites on a surface, nutritional cues, or in some cases, by exposure of cells to sub-inhibitory concentrations of antibiotics. The microbial cells growing in a biofilm are physiologically distinct from individual cells of the same organism. For example, when a bacterial cell switches to the biofilm mode of growth, it undergoes a phenotypic shift in behavior in which certain genes (e.g., biofilm formation-associated) are differentially regulated. Particular examples of biofilm formation genes include cepI, cepR, suhB, CsuE, SecA, Pg1L, PilU1, AlgZ, AlgU, LasR, FleR and PelF. In particular embodiments, the cepI gene is from a *Burkholderia* species or sub-species (e.g., *Burkholderia cepacia* complex, *Burkholderia cenocepacia*) and encodes an acylhomoserine lactone synthase. In some embodiments, the suhB gene is from a *Burkholderia* species or sub-species (e.g., *Burkholderia cepacia* complex, *Burkholderia cenocepacia*) and encodes a putative inositol-1-monophosphatase. In certain embodiments, the cepR gene is from a *Burkholderia* species or sub-species (e.g., *Burkholderia cepacia* complex, *Burkholderia cenocepacia*) and encodes an acylhomoserine lactone dependent regulatory protein. In some embodiments, the CsuE gene is from *Acinetobacter baumannii* and encodes a chaperone-usher pili assembly system protein. In some embodiments, the SecA gene is from *Acinetobacter baumannii* and encodes an ATPase associated with cell membrane transport. In some embodiments, the Pg1L gene is from *Acinetobacter baumannii*. In some embodiments, the PilU1 gene is from *Acinetobacter baumannii*. In some embodiments, the AlgZ gene is from *Pseudomonas aeruginosa* and encodes a protein associated with alginate biosynthesis. In some embodiments, the AlgU gene is from *Pseudomonas aeruginosa* and encodes a protein associated with alginate biosynthesis. In some embodiments, the LasR gene is from *Pseudomonas aeruginosa* and encodes a transcriptional activator protein. In some embodiments, the FleR gene is from *Pseudomonas aeruginosa* and encodes a transcriptional regulator of flagellar expression. In some embodiments, the PelF gene is from *Pseudomonas aeruginosa* and encodes a polysaccharide biosynthesis protein. Exemplary translational start codon region sequences of biofilm formation genes from *Burkholderia* are provided in Table 1B below. In some embodiments, the rpoD gene is from *Acinetobacter baumannii* and encodes an RNA polymerase. In some embodiments, the PolB gene is from *Pseudomonas aeruginosa* and encodes a DNA polymerase II.

TABLE 1

Exemplary Target Sequences

| Description | Sequence* | SEQ ID NO: |
|---|---|---|
| A: Exemplary Antibiotic Resistance Target Sequence | | |
| *E. coli* New Delhi Metallo-beta-lactamase-1 (NDM-1) | GTTTTTAATG CTGAATAAAA GGAAAACTTG ATGGAATTGC CCAATATTAT GCACCCGGTC | 1 |
| *Klebsiella pneumoniae* clone KPM_nasey New Delhi metallo-beta-lactamase (blaNDM-1) gene | GTTTTTAATG CTGAATAAAA GGAAAACTTG ATGGAATTGC CCAATATTTA GCACCCGGTC | 2 |
| *Acinetobacter baumannii* metalio-beta-lactamase | AACATCAAAA AGTCACTAGG TTTGGACAGT ATGCAAAAGC ATCTTTTACT TCCTTTATTT | 3 |
| *Acinetobacter baumannii* 1605 RND-type multidrug efflux pump subunit AdeA | AACATCAAAA AGTCACTAGG TTTGGACAGT ATGCAAAAGC ATCTTTTACT TCCTTTATTT | 4 |
| B: Exemplary Biofprm Formation Target Sequence | | |
| cenI *Burkholderia cenocepacia* J2315 N-acylhomoserine lactone synthase | GCATACAAAA GCACAGATCC GAGGACATCC ATGCAGACCT TCGTTCACGA GGAAGGGCGG | 5 |
| cepI *Actinetobacter baumannii* AB307-0294 | TCACTTGAAA AATAAGTGGA AGCACTTGTA ATGAATATTA TTGCTGGATT TCAAAACAAT | 6 |
| suhB *Actinetobacter baumannii* AYE | TCTTCAAATT TGTATTGTAG TGGGTGTTCA ATGGAACCTA TGGTGGTGAT GGCTGCGCGT | 7 |
| SuhB *Burkholderia cenocepacia* | CCCGTGCCGC CGGCTACAGG ATCCAGGCTC ATGCATCCCA TGCTCAACAT TGCTGTCAAG | 8 |

TABLE 1 -continued

Exemplary Target Sequences

| Description | Sequence* | SEQ ID NO: |
|---|---|---|
| J2315 Inositol-1-monophosphate suhB Gene ID: 6932290 Locus Tag BCAL2157 | CCCGTGCCGCCGGCTACAGGATCCAGGCTCATGCATCCCATGC TCAACATTGCTGTCAAGGCTGCGCGCCGCGCCGGACAGATCAT CAATCGCGCGTCCCTCGATCTCGACCTGATCGAGATCCGCAAG AAGCAGCAGAACGACTTCGTCACCGAAGTGGACAAGGCCGCCG AAGACGCGATCATCGAGACGCTGAAGACCGCCTACCCCGACCA CGCGATCCTCGCGGAGGAATCGGGCGAATCCGACAACGAATCC GAATTCAAGTGGATCATCGATCCGCTCGACGGCACGACCAACT TCATCCACGGCTTCCCGTATTACTGCGTATCGATCGCGCTCGA GCACAAGGGCGTCGTCACGCAGGCCGTCGTCTACGATCCGAAC AAGAACGACCTGTTCACGGCCACCCGCGGCCGCGGCGCATACC TGAACGACCGCCGCATCCGCGTCGGCCGCCGCGACCGCCTGGC AGACGCACTGGTCGGCACGGGCTTCCCGTTCCGCGAGAAGGAC GGCCTCGACGCCTACGCGCGCCTCTTCACCGAAATGACGCAGG CCTGCACGGGCCTGCGCCGTCCGGGCGCGGCGGCGCTCGATCT CGCGAACGTCGCGGCCGGCCGCCTCGACGCGTTCTTCGAGCAA GGCATCAACGTGTGGGACATGGCAGCGGGCAGCCTGCTGATCA CCGAGGCCGGCGGCCTCGTCGGGAACTACACGGGCGACGCCGA TTTCCTGCATCGCCACGAGATCGTCGCCGCGAACCC | |

*The thymines (T) can be uracils (U)

Thus, in certain embodiments, antisense targeting sequences are designed to hybridize to a region of one or more of the target sequences listed in Table 1 or a target gene described herein. Selected antisense targeting sequences can be made shorter, e.g., about 8, 9, 10, 11, 12, 13, 14, or 15 bases, or longer, e.g., about 20, 30, or 40 bases, and include a small number of mismatches, as long as the sequence is sufficiently complementary to reduce transcription or translation upon hybridization to the target sequence, and optionally forms with the RNA a heteroduplex having a Tm of 45° C. or greater.

In certain embodiments, the degree of complementarity between the target sequence and antisense targeting sequence is sufficient to form a stable duplex. The region of complementarity of the antisense oligomers with the target RNA sequence may be as short as 8-9 bases, 8-10 bases, 8-11 bases, 8-12 bases, 10-11 bases, 10-12 bases, but can be 12-15 bases or more, e.g., 10-40 bases, 12-30 bases, 12-25 bases, 15-25 bases, 12-20 bases, or 15-20 bases, including all integers in between these ranges. An antisense oligomer of about 10-15 bases is generally long enough to have a unique complementary sequence. In certain embodiments, a minimum length of complementary bases may be required to achieve the requisite binding Tm, as discussed herein.

In certain embodiments, oligomers as long as 40 bases may be suitable, where at least a minimum number of bases, e.g., 10-12 bases, are complementary to the target sequence. In general, however, facilitated or active uptake in cells is optimized at oligomer lengths of less than about 30 or less than about 20 bases. Included are antisense oligomers that consist of about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases, in which at least about 6, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 contiguous or non-contiguous bases are complementary to a target gene described herein, for example, a target sequence of Table 1 (e.g., SEQ ID NOS: 1-9).

In certain embodiments, antisense oligomers may be 100% complementary to the target sequence, or may include mismatches, e.g., to accommodate variants, as long as a heteroduplex formed between the oligomer and target sequence is sufficiently stable to withstand the action of cellular nucleases and other modes of degradation which may occur in vivo, and reduce expression of the targeted mRNA. Hence, certain oligomers may have about or at least about 70% sequence complementarity, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence complementarity, between the oligomer and the target sequence. Oligomer backbones that are less susceptible to cleavage by nucleases are discussed herein. Mismatches, if present, are typically less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the target sequence, it is effective to stably and specifically bind to the target sequence, for example, such that translation of the target RNA is reduced.

The stability of the duplex formed between an oligomer and a target sequence is a function of the binding Tm and the susceptibility of the duplex to cellular enzymatic cleavage. The Tm of an oligomer with respect to complementary-sequence RNA may be measured by conventional methods, such as those described by Names et al., Nucleic Acid Hybridization, IRL Press, 1985, pp. 107-108 or as described in Miyada C. G. and Wallace R. B., 1987, Oligomer Hybridization Techniques, Methods Enzymol. Vol. 154 pp. 94-107.

In certain embodiments, antisense oligomers may have a binding Tm, with respect to a complementary-sequence RNA, of greater than body temperature and preferably greater than about 45° C. or 50° C. Tm's in the range 60-80° C. or greater are also included. According to well-known principles, the Tm of an oligomer, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer.

Tables 2A-2C below shows exemplary targeting sequences (in a 5'-to-3' orientation) of antisense oligomers described herein.

TABLE 2A

Exemplary Antibiotic Resistance Targeting Sequences

| Target Gene | Targeting Sequence (TS)* | TS SEQ ID NO: |
|---|---|---|
| OmpA | CAT GGA TAT CC | 10 |
| AcrA | ATG TAA ACC TC | 11 |
| AcrA | GTT CAT ATG TA | 12 |
| AcrA | AAC CCT CTG TT | 13 |
| AcrA | TGT TCA TAT GT | 14 |
| AcrB | GTC TTA ACG GC | 15 |
| AcrB | AGG CAT GTC IT | 16 |
| AcrB | TAG GCA TGT CT | 17 |
| AcrR | TAT GTT CGT GA | 18 |
| TolC | TTC ATT TGC AT | 19 |
| TolC | ATT CCT TGT GG | 20 |
| TolC | TTT GCA TTC CT | 21 |
| KPC | GAT ACA GTG AC | 22 |
| KPC 1-4 | AAC GAT ATT CC | 23 |
| NDM-1 | TCA AGT TTT CC | 24 |
| NDM-1 | TCC TTT TAT TC | 25 |
| NDM-1 | GGCAATTCCAT | 50 |

TABLE 2B

Exemplary Biofilm Formation Targeting Sequences

| Target Gene | Targeting Sequence (TS) | TS SEQ. ID NO: |
|---|---|---|
| CsuE | TTA TAT TCA TGG | 26 |
| CsuE | TCA TGG CAA AG | 27 |
| CsuE | TIT CCT GTC AA | 28 |
| SecA | TTG CCA ACA TG | 29 |
| PglL | CAT TAC CCA AG | 30 |
| PilU1 | TTA AAA TCC AT | 31 |
| AlgZ | TAG GCA TCG AC | 32 |
| AlgU | AAA GCT CCT CT | 33 |
| LasR | AGG CCA TAG CG | 34 |
| FleR | TTA CTC CTG AA | 35 |
| PelF | TTC GGT CAT GT | 36 |

TABLE 2C

Exemplary Essential Targeting Sequences

| Target Gene | Targeting Sequence (TS)* | TS SEQ ID NO: |
|---|---|---|
| RpoD | TCA TCT TTG CT | 37 |
| PolB | AGT AAC TCC AC | 38 |

*The thymines (T) can be uracils (U).

Certain antisense oligomers thus comprise, consist, or consist essentially of a targeting sequence in Tables 2A-2C (e.g., SEQ ID NOS: 10-38) or a variant or contiguous or non-contiguous portion(s) thereof. For instance, certain antisense oligomers comprise about or at least about 6, 7, 8, 9, 10, 11, 12, 13, 14, 15, 16, 17, 18, 19, 20, 21, 22, 23, 24, 25, 26, or 27 contiguous or non-contiguous nucleotides of any of the targeting sequences in Tables 2A-2C (e.g., SEQ ID NOS: 10-38). For non-contiguous portions, intervening nucleotides can be deleted or substituted with a different nucleotide, or intervening nucleotides can be added. Additional examples of variants include oligomers having about or at least about 70% sequence identity or homology, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity or homology, over the entire length of any of the targeting sequences in Tables 2A-2C (e.g., SEQ ID NOS: 10-38).

The activity of antisense oligomers and variants thereof can be assayed according to routine techniques in the art (see, e.g., the Examples).

I. Antisense Oligomer Compounds

The antisense oligomers typically comprises a base sequence of sufficient length and complementarity to specifically hybridize to a bacterial mRNA target sequence that encodes a virulence factor, and thereby reduce expression (e.g., translation) of the virulence factor protein. This requirement is optionally met when the oligomer compound has the ability to be actively taken up by bacterial cells, and once taken up, form a stable duplex (or heteroduplex) with the target mRNA, optionally with a Tm greater than about 40° C. or 45° C.

A. Antisense Oligomer Chemical Features

In certain embodiments, the backbone of the antisense oligomer is substantially uncharged, and is optionally recognized as a substrate for active or facilitated transport across a cell wall and/or cell membrane. The ability of the oligomer to form a stable duplex with the target RNA may also relate to other features of the backbone, including the length and degree of complementarity of the antisense oligomer with respect to the target, the ratio of G:C to A:T base matches, and the positions of any mismatched bases. The ability of the antisense oligomer to resist cellular nucleases may promote survival and ultimate delivery of the agent to the cell. Exemplary antisense oligomer targeting sequences are listed in Tables 2A-2C (supra).

In certain embodiments, the antisense oligomer is a morpholino-based oligomer, for example, a phosphorodiamidate morpholino oligomer (PMO). Morpholino-based oligomers refer to an oligomer comprising morpholino subunits supporting a nucleobase and, instead of a ribose, contains a morpholine ring. Exemplary internucleoside linkages include, for example, phosphoramidate or phosphorodiamidate internucleoside linkages joining the morpholine ring nitrogen of one morpholino subunit to the 4' exocyclic carbon of an adjacent morpholino subunit. Each morpholino subunit comprises a purine or pyrimidine nucleobase effective to bind, by base-specific hydrogen bonding, to a base in an oligonucleotide.

Morpholino-based oligomers (including antisense oligomers) are detailed, for example, in U.S. Pat. Nos. 5,698,685; 5,217,866; 5,142,047; 5,034,506; 5,166,315; 5,185,444; 5,521,063; 5,506,337 and pending U.S. patent application Ser. Nos. 12/271,036; 12/271,040; and PCT Publication No. WO/2009/064471 and WO/2012/043730 and Summerton et al. 1997, Antisense and Nucleic Acid Drug Development, 7, 187-195, which are hereby incorporated by reference in their entirety.

Within the oligomer structure, the phosphate groups are commonly referred to as forming the "internucleoside linkages" of the oligomer. The naturally occurring internucleoside linkage of RNA and DNA is a 3' to 5' phosphodiester linkage. A "phosphoramidate" group comprises phosphorus having three attached oxygen atoms and one attached nitrogen atom, while a "phosphorodiamidate" group comprises phosphorus having two attached oxygen atoms and two attached nitrogen atoms. In the uncharged or the cationic internucleoside linkages of the morpholino-based oligomers described herein, one nitrogen is always pendant to the linkage chain. The second nitrogen, in a phosphorodiamidate linkage, is typically the ring nitrogen in a morpholine ring structure.

Accordingly, various embodiments of the disclosure include a substantially uncharged antisense morpholino oligomer, composed of morpholino subunits and phosphorus-containing intersubunit linkages joining a morpholino nitrogen of one subunit to a 5'-exocyclic carbon of an adjacent subunit, and having (a) about 10-40 nucleotide bases, and (b) a targeting sequence of sufficient length and complementarity to specifically hybridize to a bacterial mRNA target sequence that encodes a virulence factor; where the oligomer is conjugated to a cell-penetrating peptide (CPP). In particular embodiments, the morpholino subunits are joined by phosphorous-containing intersubunit linkages in accordance with the structure:

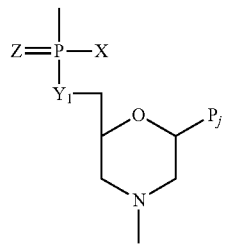

where $Y_1$=oxygen (O) or sulfur, nitrogen, or carbon; Z=oxygen or sulfur, preferably oxygen; Pj is a purine or pyrimidine base-pairing moiety effective to bind, by base-specific hydrogen bonding, to a base in a polynucleotide, and X is —NRR' where R and R' are the same or different and are either H or alkyl. In particular embodiments, X is —NRR', where R and R' are the same or different and are either H or methyl.

Figure 1A:
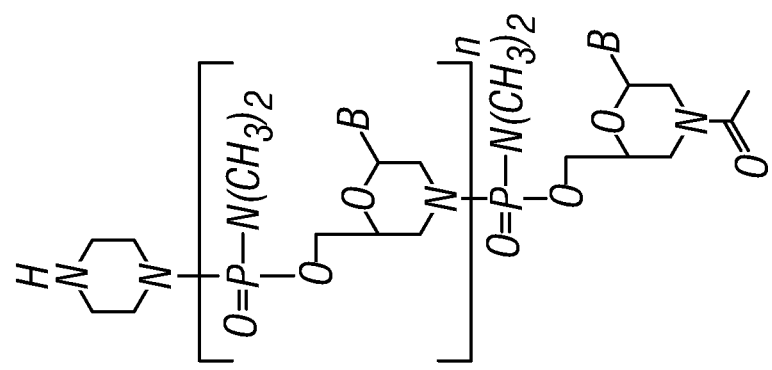
FIG. 1A shows an exemplary morpholino oligomer structure with a phosphorodiamidate linkage.

Also included are antisense oligomer that comprise a sequence of nucleotides of the formula in FIGS. 1A-1E. In FIG. 1A, B is a purine or pyrimidine base-pairing moiety effective to bind, by base-specific hydrogen bonding, to a base in a polynucleotide. $Y_1$ or $Y_2$ may be oxygen, sulfur, nitrogen, or carbon, preferably oxygen. The X moiety pendant from the phosphorus may be fluorine, an alkyl or substituted alkyl, an alkoxy or substituted alkoxy, a thioalkoxy or substituted thioalkoxy, or unsubstituted, monosubstituted, or disubstituted nitrogen, including cyclic structures, such as morpholines or piperidines. Alkyl, alkoxy and thioalkoxy include 1-6 carbon atoms. The Z moieties may be sulfur or oxygen, and are preferably oxygen.

In various aspects, an antisense oligomer of the disclosure includes a compound of formula (I):

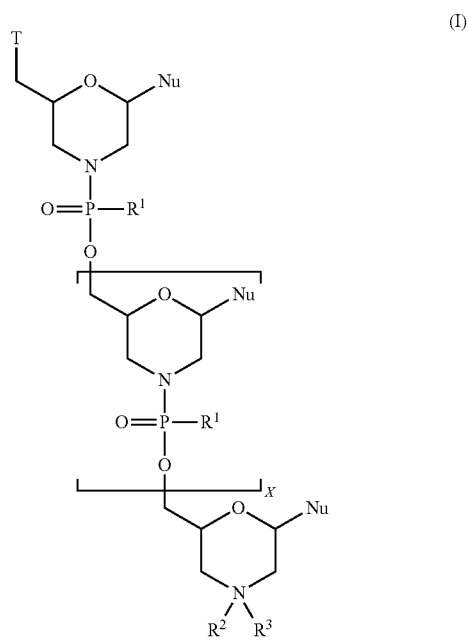

or a pharmaceutically acceptable salt thereof, where each Nu is a nucleobase which taken together forms a targeting sequence;

X is an integer from 9 to 38;

T is selected from OH and a moiety of the formula:

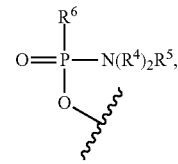

where each $R^4$ is independently $C_1$-$C_6$ alkyl, and $R^5$ is selected from an electron pair and H, and $R^6$ is selected from OH, —N($R^7$)$CH_2C(O)NH_2$, and a moiety of the formula:

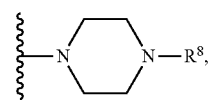

where:

$R^7$ is selected from H and $C_1$-$C_6$ alkyl, and $R^8$ is selected from G, —C(O)—$R^9$OH, acyl, trityl, and 4-methoxytrityl, where:

$R^9$ is of the formula —(O-alkyl)$_y$- wherein y is an integer from 3 to 10 and each of the y alkyl groups is independently selected from $C_2$-$C_6$ alkyl;

each instance of $R^1$ is $—N(R^{10})_2R^{11}$ wherein each $R^{10}$ is independently $C_1$-$C_6$ alkyl, and $R^{11}$ is selected from an electron pair and H;

$R^2$ is selected from H, G, acyl, trityl, 4-methoxytrityl, benzoyl, stearoyl, and a moiety of the formula:

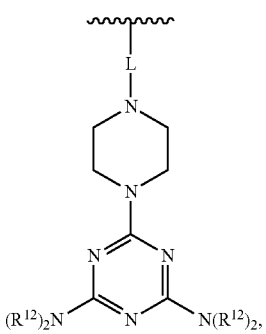

where L is selected from $—C(O)(CH_2)_6C(O)—$ and $—C(O)(CH_2)_2S_2(CH_2)_2C(O)—$, and each $R^{12}$ is of the formula $—(CH_2)_2OC(O)N(R^{14})_2$ wherein each $R^{14}$ is of the formula $—(CH_2)_6NHC(=NH)NH_2$; and $R^3$ is selected from an electron pair, H, and $C_1$-$C_6$ alkyl, wherein G is a cell penetrating peptide ("CPP") and linker moiety selected from $—C(O)(CH_2)_5NH—CPP$, $—C(O)(CH_2)_2NH—CPP$, $—C(O)(CH_2)_2NHC(O)(CH_2)_5NH—CPP$, and $—C(O)CH_2NH—CPP$, or G is of the formula:

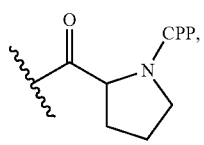

wherein the CPP is attached to the linker moiety by an amide bond at the CPP carboxy terminus, with the proviso that only one instance of G is present, wherein the targeting sequence specifically hybridizes to a bacterial mRNA target sequence that encodes a virulence factor.

In some embodiments, X is from 9 to 18. In certain embodiments, X is 9, 10, 11, 12, 13, 14, 15, 16, 17, 18, 19, 20, 21, 22, 23, 24, 25, 26, 27, 28, 29 or 30.

In certain embodiments, T is selected from:

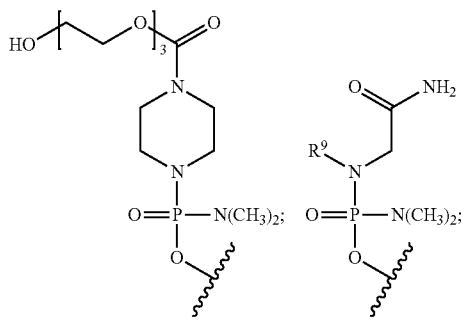

-continued

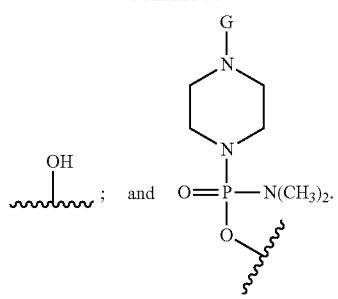

In some embodiments, $R^2$ is selected from H, G, acyl, trityl, 4-methoxytrityl, benzoyl, and stearoyl.

In various embodiments, T is selected from:

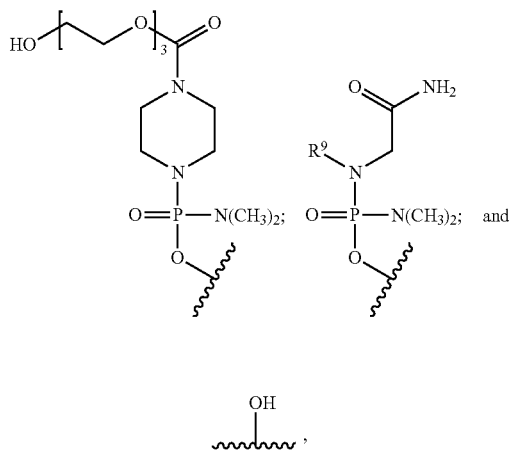

and $R^2$ is G.

In some embodiments, T is of the formula:

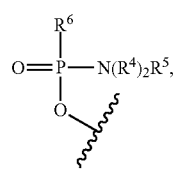

$R^6$ is of the formula:

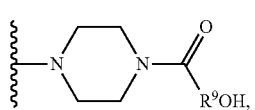

and $R^2$ is G.

In certain embodiments, T is of the formula:

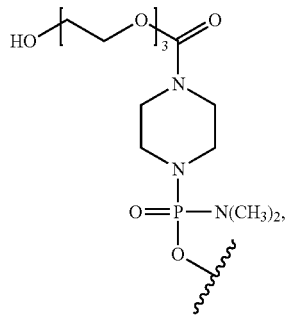

and R² is G.

In certain embodiments, T is of the formula:

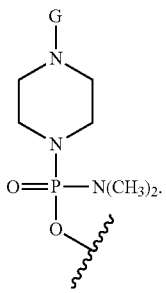

In some embodiments, R² is G or T is of the formula:

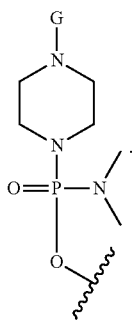

In some embodiments, R² is selected from H, acyl, trityl, 4-methoxytrityl, benzoyl, and stearoyl.

In various embodiments, R² is selected from H or G, and R³ is selected from an electron pair or H. In a particular embodiment, R² is G. In some embodiments, R² is H or acyl. In some embodiments, each R¹ is —N(CH₃)₂. In some embodiments, at least one instance of R¹ is —N(CH₃)₂. In certain embodiments, each instance of R¹ is —N(CH₃)₂.

In various embodiments of the disclosure, an antisense oligomer of the disclosure includes a compound of formula (II):

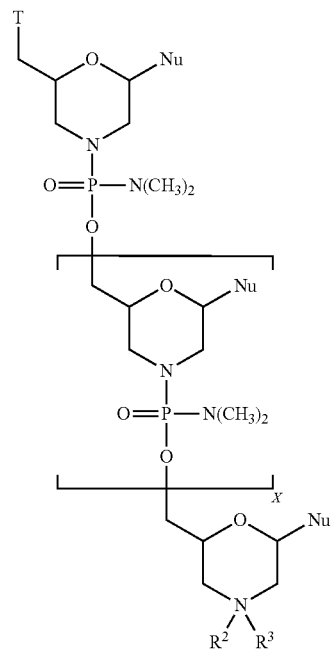

or a pharmaceutically acceptable salt thereof, where each Nu is a nucleobase which taken together forms a targeting sequence;

X is an integer from 9 to 28;

T is selected from:

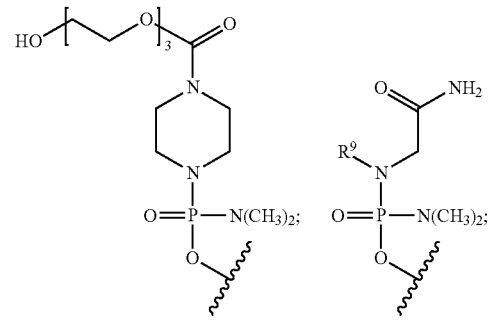

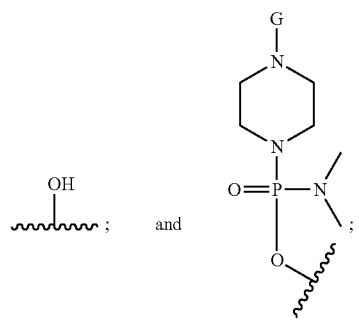

$R^2$ is selected from H, G, acyl, trityl, 4-methoxytrityl, benzoyl, and stearoyl; and $R^3$ is selected from an electron pair, H, and $C_1$-$C_6$ alkyl, wherein G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, and —C(O)CH$_2$NH—CPP, or G is of the formula:

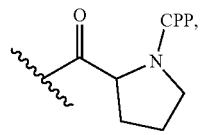

wherein the CPP is attached to the linker moiety by an amide bond at the CPP carboxy terminus, with the proviso that only one instance of G is present. In various embodiments, $R^2$ is G or T is of the formula:

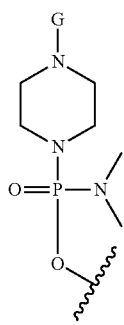

In some embodiments, T is TEG as defined above, $R^2$ is G, and $R^3$ is an electron pair or H. In certain embodiments, $R^2$ is selected from H, acyl, trityl, 4-methoxytrityl, benzoyl, and stearoyl and T is of the formula:

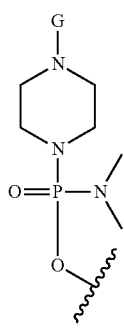

In various aspects, an antisense oligomer of the disclosure includes a compound of formula (III):

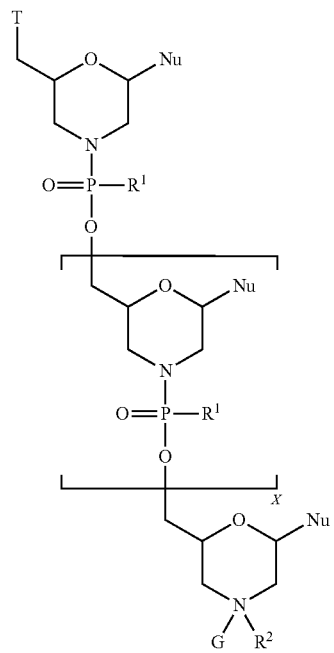

or a pharmaceutically acceptable salt thereof, where each Nu is a nucleobase which taken together forms a targeting sequence;

X is an integer from 9 to 28;

T is selected from:

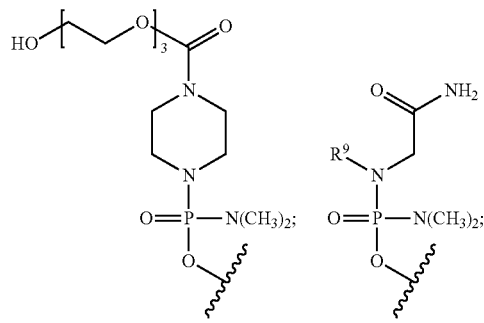

each instance of $R^1$ is —N($R^{10}$)$_2$$R^{11}$ wherein each $R^{10}$ is independently $C_1$-$C_6$ alkyl, and $R^{11}$ is selected from an electron pair and H;

$R^2$ is selected from an electron pair, H, and $C_1$-$C_6$ alkyl; and

G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, and —C(O)CH$_2$NH—CPP, or G is of the formula:

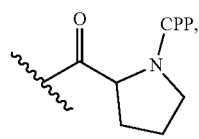

wherein the CPP is attached to the linker moiety by an amide bond at the CPP carboxy terminus.

In some embodiments, at least one instance of R$^1$ is —N(CH$_3$)$_2$. In certain embodiments, each instance of R$^1$ is —N(CH$_3$)$_2$.

In various aspects, an antisense oligomer of the disclosure includes a compound of formula (IV):

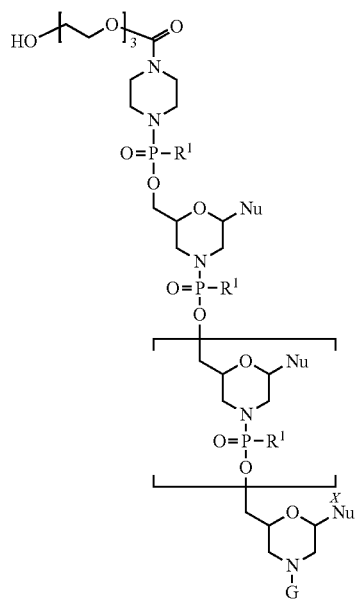

(IV)

or a pharmaceutically acceptable salt thereof, wherein:
X is an integer from 9 to 28;
each Nu is a nucleobase which taken together forms a targeting sequence;
each instance of R$^1$ is —N(R$^{10}$)$_2$R$^{11}$ wherein each R$^{10}$ is independently C$_1$-C$_6$ alkyl, and R$^{11}$ is selected from an electron pair and H; and
G is a cell penetrating peptide ("CPR") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, and —C(O)CH$_2$NH—CPP, or G is of the formula:

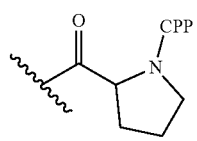

wherein the CPP is attached to the linker moiety by an amide bond at the CPP carboxy terminus. In some embodiments, at least one instance of R$^1$ is —N(CH$_3$)$_2$. In certain embodiments, each instance of R$^1$ is —N(CH$_3$)$_2$.

In various aspects, an antisense oligomer of the disclosure can be a compound of formula (V):

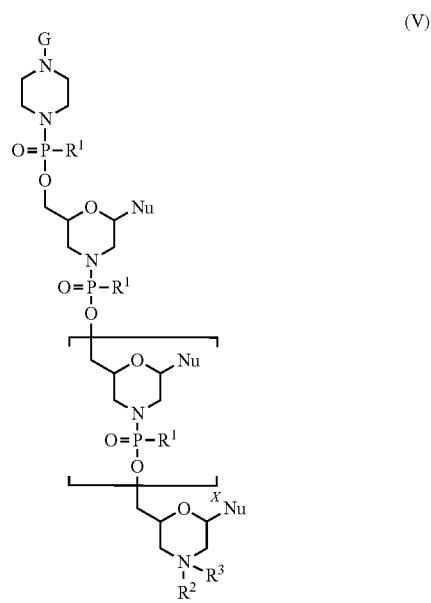

(V)

wherein:
X is an integer from 9 to 18;
each Nu is a nucleobase which taken together forms a targeting sequence;
each instance of R$^1$ is —N(R$^{10}$)$_2$R$^{11}$ wherein each R$^{10}$ is independently C$_1$-C$_6$ alkyl, and R$^{11}$ is selected from an electron pair and H;
R$^2$ is selected from H, trityl, 4-methoxytrityl, acyl, benzoyl, and stearoyl; and
R$^3$ is selected from an electron pair, H, and C$_1$-C$_6$ alkyl,
wherein G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, and —C(O)CH$_2$NH—CPP, or G is of the formula:

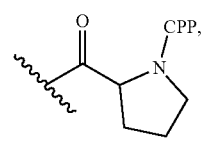

wherein the CPP is attached to the linker moiety by an amide bond at the CPP carboxy terminus. In some embodiments, at least one instance of R$^1$ is —N(CH$_3$)$_2$. In certain embodiments, each instance of R$^1$ is —N(CH$_3$)$_2$.

In various aspects, an antisense oligomer of the disclosure includes a compound of formula (VI):

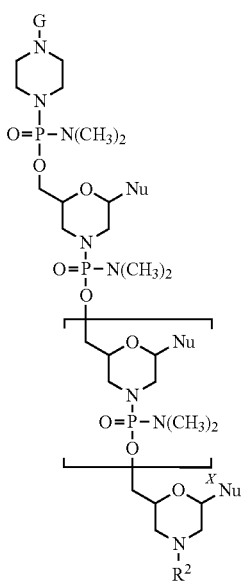

(VI)

or a pharmaceutically acceptable salt thereof, wherein:
X is an integer from 9 to 28;
each Nu is a nucleobase which taken together forms a targeting sequence;
$R^2$ is selected from H or acyl; and
G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, and —C(O)CH$_2$NH—CPP, or G is of the formula:

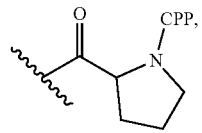

wherein the CPP is attached to the linker moiety by an amide bond at the CPP carboxy terminus.

The antisense oligomers can be prepared by stepwise solid-phase synthesis, employing methods known in the art and described in the references cited herein.

B. Cell-Penetrating Peptides

In certain embodiments, the antisense oligomer is conjugated to a cell-penetrating peptide (CPP). In some embodiments, the CPP is an arginine-rich peptide. By "arginine-rich carrier peptide" is meant that the CPP has at least 2, and preferably 2, 3, 4, 5, 6, 7, or 8 arginine residues, each optionally separated by one or more uncharged, hydrophobic residues, and optionally containing about 6-14 amino acid residues. FIGS. 1F-1H show exemplary chemical structures of CPP-PMO conjugates used in the Examples, including 5' and 3' PMO conjugates.

TABLE C1

Exemplary Cell-Penetrating Peptides

| Name | Sequence | SEQ ID NO: |
|---|---|---|
| (RXR)$_4$ | RXRRXRRXRRXR | 43 |
| (RFF)$_3$R | RFFRFFRFFR | 44 |

TABLE C1-continued

Exemplary Cell-Penetrating Peptides

| Name | Sequence | SEQ ID NO: |
|---|---|---|
| (RXR)$_4$XB | RXRRXRRXRRXRXB | 45 |
| (RFF)$_3$RXB | RFFRFFRFFRXB | 46 |
| (RFF)$_3$RG | RFFRFFRFFR | 47 |
| R$_6$G | RRRRRRG | 48 |
| R$_6$ | RRRRRR | 49 |

X is 6-aminohexanic acid; B is β-alanine;
F is phenylalanine; G is glycine

CPPs, their synthesis, and methods of conjugating a CPP to an oligomer are detailed, for example, in International Patent Application Publication Nos. WO 2004/097017, WO 2009/005793, and WO 2012/150960, which are all incorporated by reference in their entirety.

In some embodiments, the CPP is linked at its C-terminus to the 3'-end or the 5'-end of the oligomer via a 1, 2, 3, 4, or 5 amino acid linker. In particular embodiments, including antisense oligomer compounds of formula (I)-(VI), the linkers can include: —C(O)(CH$_2$)$_5$NH—CPP (X linker), —C(O)(CH$_2$)$_2$NH—CPP (B linker), —C(O)(CH$_2$)$_2$NHC(O)(CH$_2$)$_5$NH—CPP (XB peptide linker), and —C(O)CH$_2$NH—CPP (Gly linker), or G is of the formula:

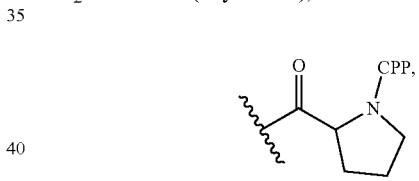

wherein the CPP is attached to the linker moiety by an amide bond at the CPP carboxy terminus. In some embodiments of the disclosure, including antisense oligomer compounds of formula (I)-(VI), G is selected from SEQ ID NOs: 45 to 48. In various embodiments, including antisense oligomer compounds of formula (I)-(VI), the CPP is selected from SEQ ID NO: 43, 44, and 49, and the linker is selected from the group described above.

In some embodiments, including antisense oligomer compounds of formula (I)-(VI), the CPP is selected from:

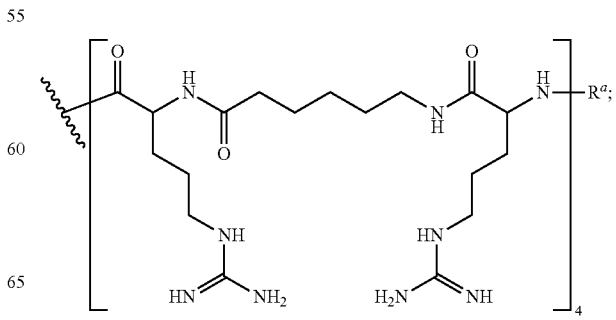

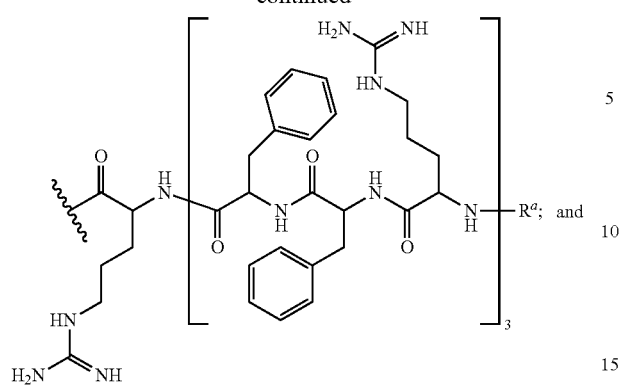
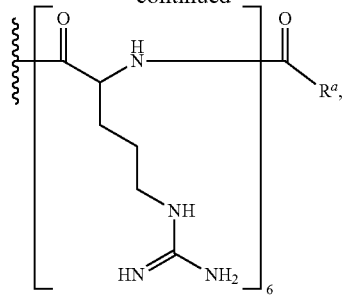
wherein $R^a$ is selected from H, acetyl, benzoyl, and stearoyl.
In some embodiments, including antisense oligomer compounds of formula (I)-(VI), G is selected from:
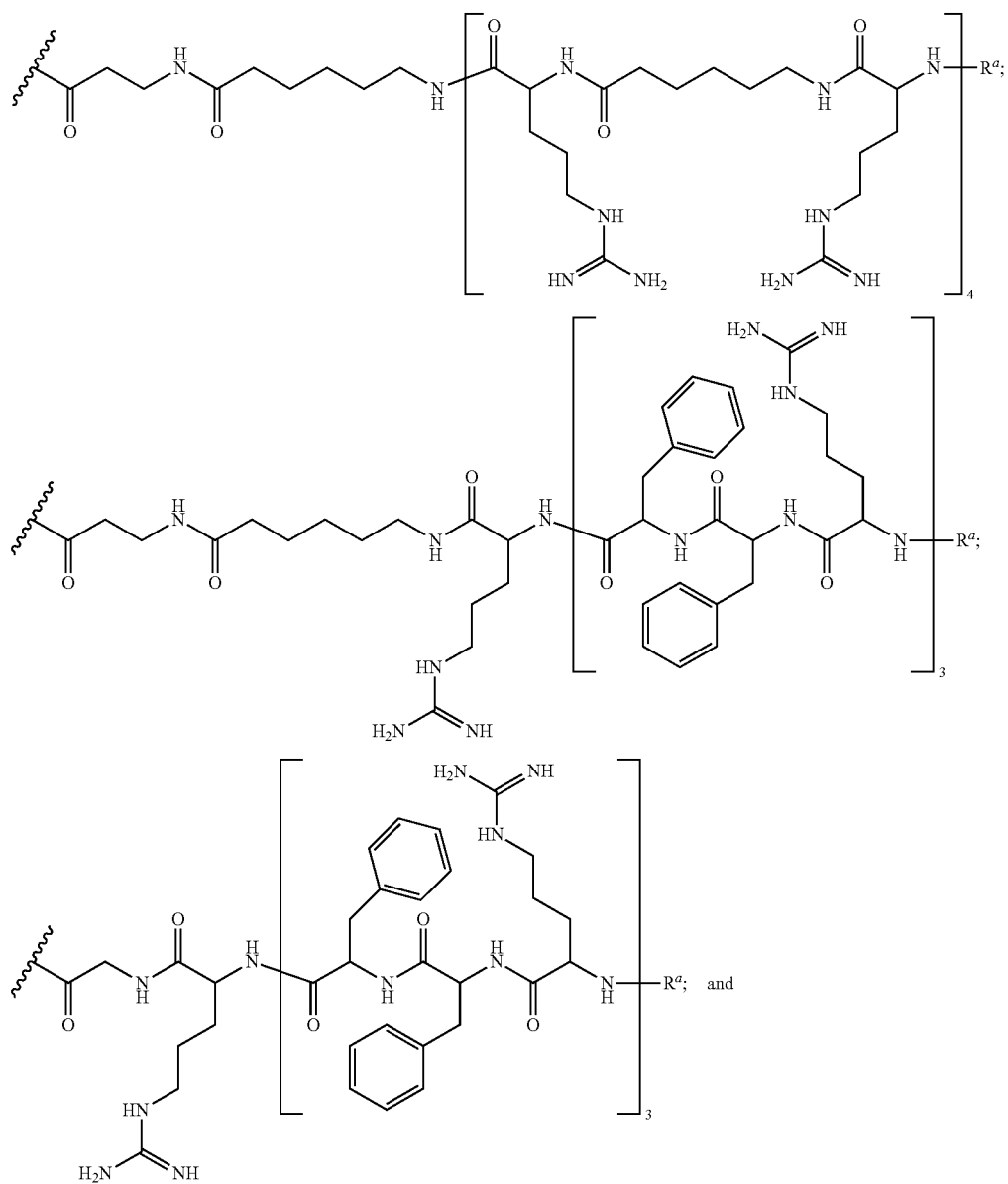

-continued
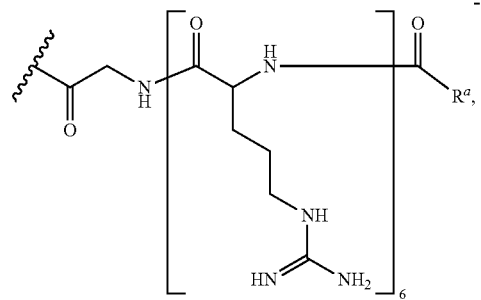
wherein $R^a$ is selected from H, acetyl, benzoyl, and stearoyl.
In various aspects, an antisense oligomer of the disclosure, or a pharmaceutically acceptable salt thereof, includes an antisense oligomer of the formula (VII) selected from:

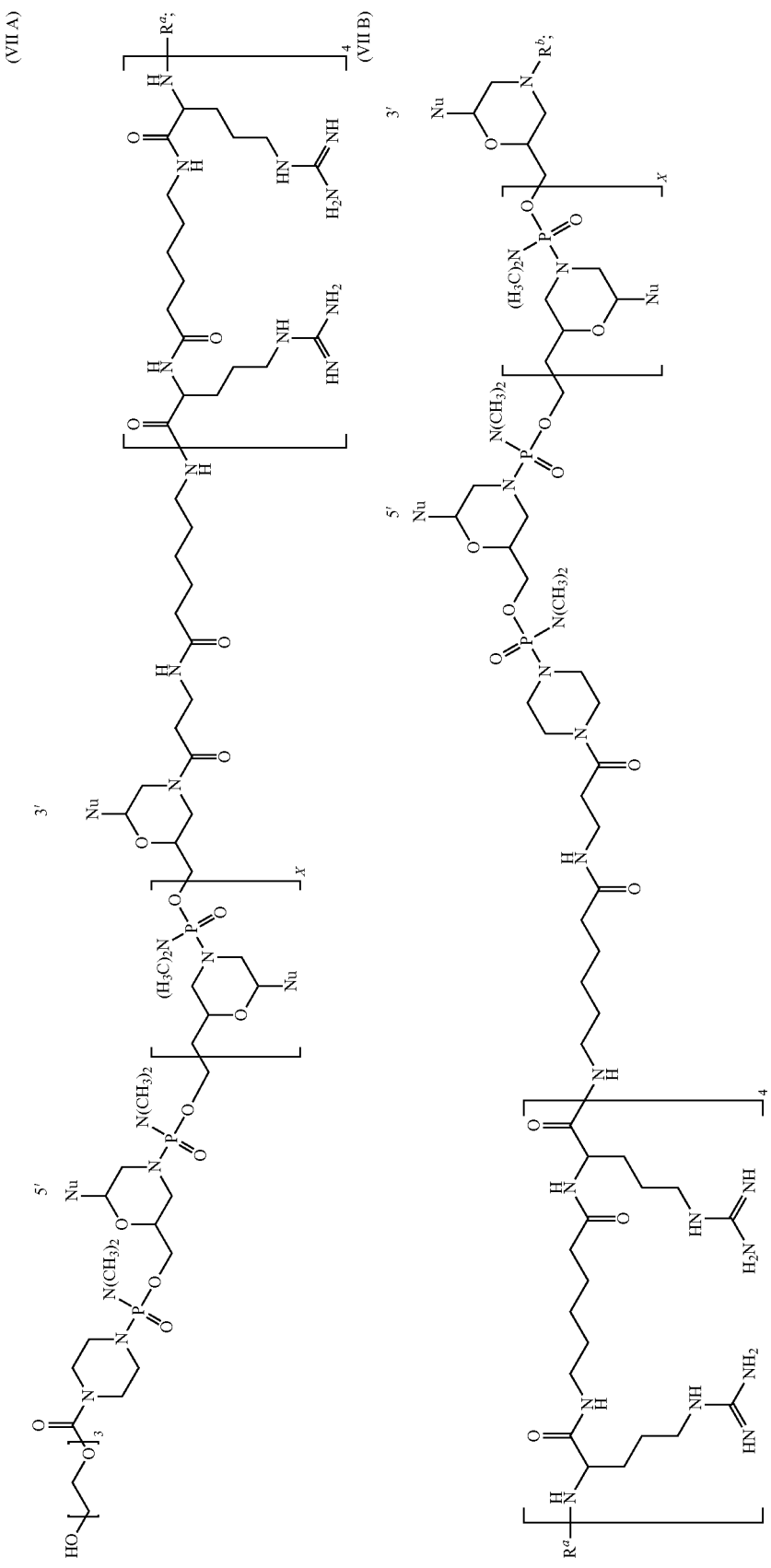

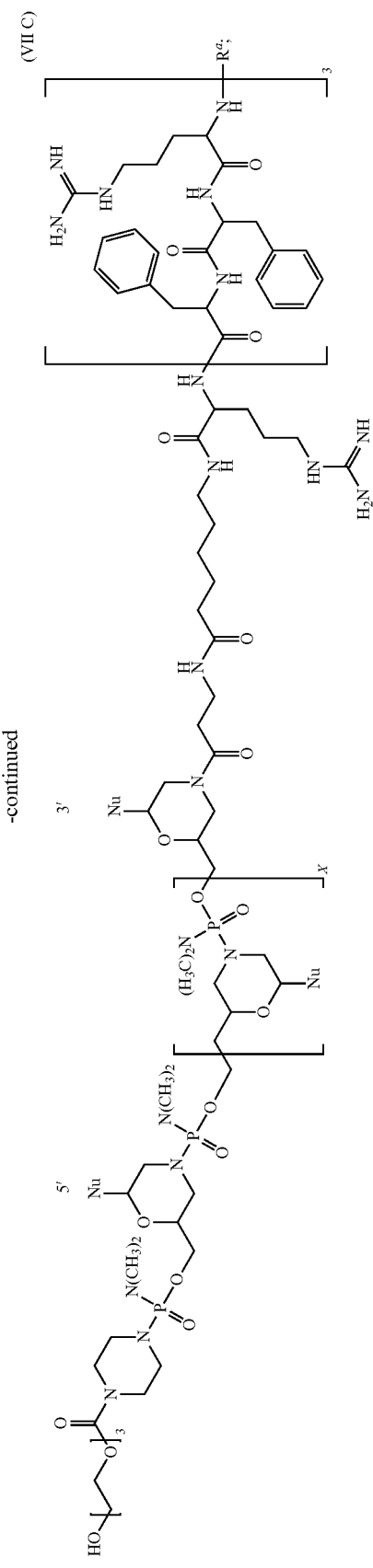
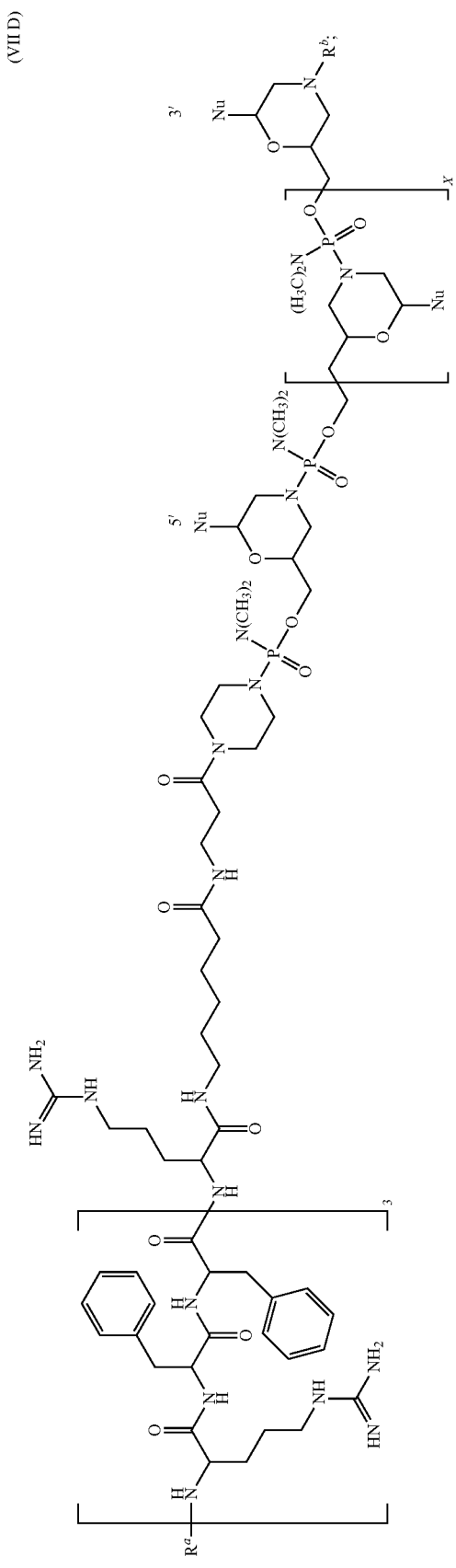

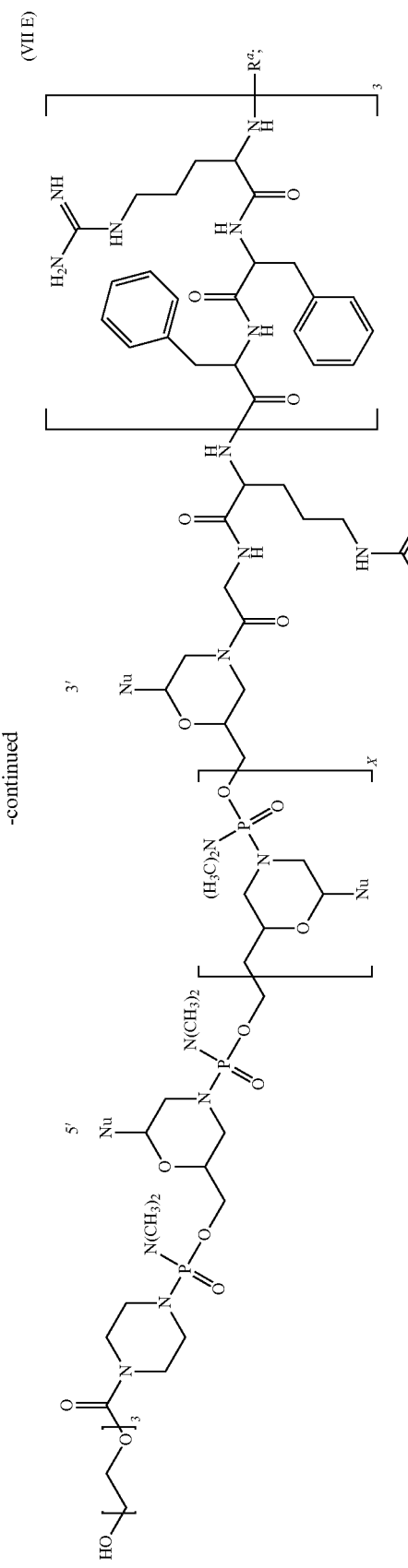
(VIIE)
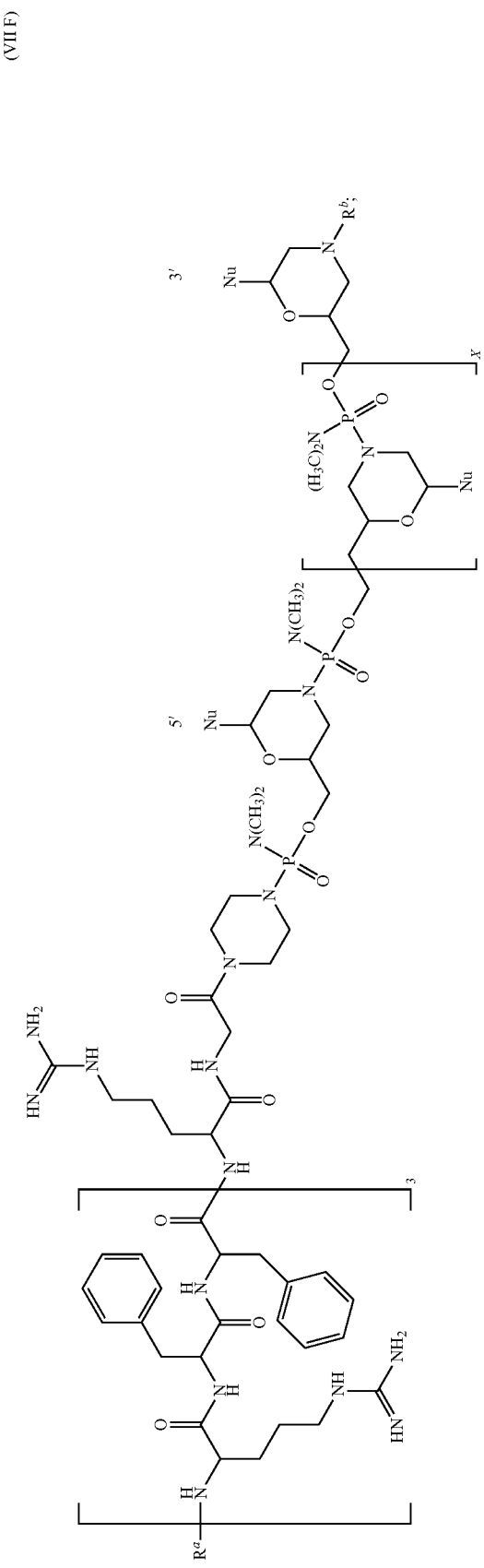
(VIIF)

(VIIG)
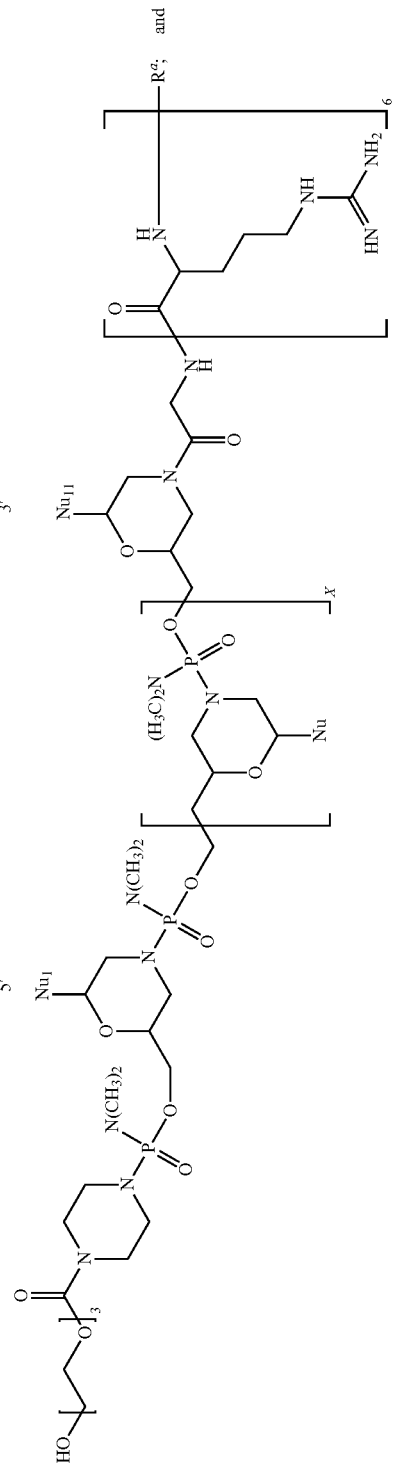
(VIIH)
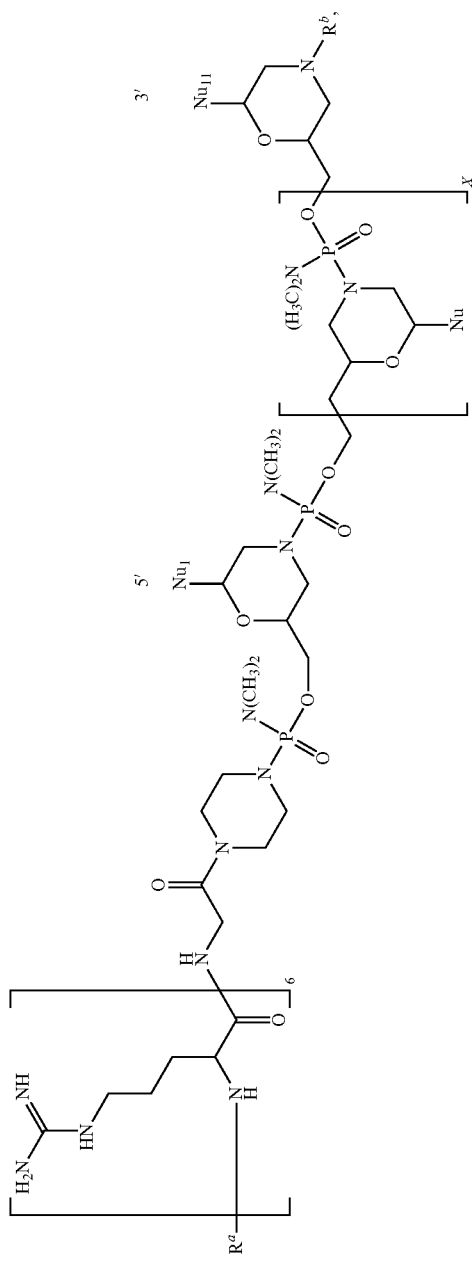

wherein X is an integer from 9 to 38, $R^a$ is selected from H, acetyl, benzoyl, and stearoyl, $R^b$ is selected from H, acetyl, benzoyl, stearoyl, trityl, and 4-methoxytrityl, and each Nu is a purine or pyrimidine base-pairing moiety which taken together form a targeting sequence described above.

C. Antisense Oligomer Targeting Sequence

In various embodiments of the antisense oligomers of the disclosure, including the antisense oligomer compounds of formulas (I)-(VII), the targeting sequence can specifically hybridize to a bacterial mRNA target sequence that encodes a virulence factor. In some embodiments, the target sequence comprises a translational start codon of the bacterial mRNA and/or a sequence within about 30 bases upstream or downstream of the translational start codon of the bacterial mRNA. In certain embodiments, the virulence factor can be an antibiotic resistance protein, a biofilm formation protein or an essential protein. In some embodiments, the antibiotic resistance protein may be selected from at least one of New Delhi metallo-beta-lactamase (NDM-1), resistance-nodulation-cell division (RND)-type multidrug efflux pump subunit AdeA (adeA), serine beta-lactamase (KPC or KPC 1-4), acridine resistance complex protein AcrA, acridine resistance complex protein AcrB, acridine resistance complex repressor protein AcrR, acridine resistance complex protein TolC, and outer membrane protein A (OmpA). In some embodiments, the target sequence can be selected from SEQ ID NOS: 1-4, wherein thymine bases (T) are optionally uracil bases (U). In certain embodiments, the targeting sequence may be one of the targeting sequences set forth in SEQ ID NOS: 10-25, may comprise a fragment of at least 10 contiguous nucleotides of SEQ ID NOS: 10-25, or may comprise a variant having at least 80% sequence identity to SEQ ID NOS: 10-25, wherein thymine bases (T) are optionally uracil bases (U). In some embodiments, the biofilm formation protein may be encoded by at least one of CepI, SuhB, CsuE, SecA, PglL, PilU1, AlgZ, AlgU, LasR, FleR and PelF. In certain embodiments, the target sequence can be selected from SEQ ID NOS: 5-9, wherein thymine bases (T) are optionally uracil bases (U). In some embodiments, the targeting sequence may be one of the targeting sequences set forth in SEQ ID NOS: 26-36, may comprise a fragment of at least 10 contiguous nucleotides of SEQ ID NOS: 26-36, or may comprise a variant having at least 80% sequence identity to SEQ ID NOS: 26-36, wherein thymine bases (T) are optionally uracil bases (U). In some embodiments, an essential protein may be encoded by at least one of RpoD or PolB. In some embodiments, the targeting sequence may be one of the targeting sequences set forth in SEQ ID NOS: 37-38, may comprise a fragment of at least 10 contiguous nucleotides of SEQ ID NOS: 37-38, or may comprise a variant having at least 80% sequence identity to SEQ ID NOS: 37-38, wherein thymine bases (T) are optionally uracil bases (U). In some embodiments of the disclosure, including the antisense oligomer compounds of formulas (I)-(VII), the targeting sequence is selected from:

a) (CAT GGA TAT CC);  SEQ ID NO: 10
b) (ATG TAA ACC TC);  SEQ ID NO: 11
c) (GTT CAT ATG TA);  SEQ ID NO: 12
d) (AAC CCT CTG TT);  SEQ ID NO: 13
e) (TGT TCA TAT GT);  SEQ ID NO: 14
f) (GTC TTA ACG GC);  SEQ ID NO: 15
g) (AAG CAT GTC TT);  SEQ ID NO: 16
h) (TAG GCA TGT CT);  SEQ ID NO: 17
i) (TAT GTT CGT GA);  SEQ ID NO: 18
j) (TTC ATT TGC AT);  SEQ ID NO: 19
k) (ATT CCT TGT GG);  SEQ ID NO: 20
l) (TTT GCA TTC CT);  SEQ ID NO: 21
m) (GAT ACA GTG AC);  SEQ ID NO: 22
n) (AAC GAT ATT CC);  SEQ ID NO: 23
o) (TCA AGT TTC CC);  SEQ ID NO: 24
and
p) (TCC TTT TAT TC),  SEQ ID NO: 25 wherein X is 9, and thymine bases (T) may be uracil bases(U).

In various embodiments of the disclosure, including the antisense oligomer compounds of formulas (I)-(VII), the targeting sequence is selected from:

a) (TTA TAT TCA TGG);  SEQ ID NO: 26
b) (TCA TGG CAA AG);  SEQ ID NO: 27
c) (TTT CCT GTC AA);  SEQ ID NO: 28
d) (TTG CCA ACA TG);  SEQ ID NO: 29
e) (CAT TAC CCA AG);  SEQ ID NO: 30
f) (TTA AAA TCC AT);  SEQ ID NO: 31
g) (TAG GCA TCG AC);  SEQ ID NO: 32
h) (AAA GCT CCT CT);  SEQ ID NO: 33
i) (AGG CCA TAG CG);  SEQ ID NO: 34
j) (TTA CTC CTG AA);  SEQ ID NO: 35
and
k) (TTC GGT CAT GT),  SEQ ID NO: 36 wherein X is 9, and thymine bases (T) may be uracil bases(U).

In various embodiments of the disclosure, including the antisense oligomer compounds of formulas (I)-(VII), the targeting sequence is selected from:

a) (TCA TCT TTG CT); SEQ ID NO: 37
and b) (TCA TGG CAA AG), SEQ ID NO: 38 wherein X is 9, and thymine bases (T) may be uracil bases(U).

D. Exemplary Antisense Oligomers

Exemplary antisense oligomers (AONs) of the disclosure include those described in Tables 3A-3C below.

TABLE 3A

Exemplary Antibiotic Resistance Targeting AONs

| PMO Name | Target Gene | Targeting Sequence (TS)* | TS SEQ ID NO: | 5' Attachment*** | 3' Attachment** | CPP SEQ ID NO. |
|---|---|---|---|---|---|---|
| PPMO#1 | OmpA | CAT GGA TAT CC | 10 | (RXR)$_4$XB— | H or —C(O)CH$_3$ | 45 |
| PPMO#2 | AcrA | ATG TAA ACC TC | 11 | (RXR)$_4$XB— | H or —C(O)CH$_3$ | 45 |
| PPMO#3 | AcrA | GTT CAT ATG TA | 12 | (RXR)$_4$XB— | H or —C(O)CH$_3$ | 45 |
| PPMO#4 | AcrA | AAC CCT CTG TT | 13 | (RXR)$_4$XB— | H or —C(O)CH$_3$ | 45 |
| PPMO#5 | AcrA | TGT TCA TAT GT | 14 | (RXR)$_4$XB— | H or —C(O)CH$_3$ | 45 |
| PPMO#6 | AcrB | GTC TTA ACG GC | 15 | (RXR)$_4$XB— | H or —C(O)CH$_3$ | 45 |
| PPMO#7 | AcrB | AGG CAT GTC TT | 16 | (RXR)$_4$XB— | H or —C(O)CH$_3$ | 45 |
| PPMO#8 | AcrB | TAG GCA TGT CT | 17 | (RXR)$_4$XB— | H or —C(O)CH$_3$ | 45 |
| PPMO#9 | AcrR | TAT GTT CGT GA | 18 | (RXR)$_4$XB— | H or —C(O)CH$_3$ | 45 |
| PPMO#10 | TolC | TTC ATT TGC AT | 19 | (RXR)$_4$XB— | H or —C(O)CH$_3$ | 45 |
| PPMO#11 | TolC | ATT CCT TGT GG | 20 | (RXR)$_4$XB— | H or —C(O)CH$_3$ | 45 |
| PPMO#12 | TolC | TTT GCA TTC CT | 21 | (RXR)$_4$XB— | H or —C(O)CH$_3$ | 45 |
| PPMO#13 | KPC | GAT ACA GTG AC | 22 | (RXR)$_4$XB— | H | 45 |
| PPMO#14 | KPC 1-14 | AAC GAT ATT CC | 23 | (RXR)$_4$XB— | H | 45 |
| PPMO#34 | KPC | GAT ACA GTG AC | 22 | TEG | R$_6$G | 48 |
| PPMO#35 | KPC | GAT ACA GTG AC | 22 | TEG | (RXR)$_4$XB— | 45 |
| PPMO#15 | NDM-1 | TCA AGT TTT CC | 24 | TEG | R$_6$G | 48 |
| PPMO#16 | NDM-1 | TCC TTT TAT TC | 25 | R$_6$G | H or —C(O)CH$_3$ | 48 |
| PPMO#17 | NDM-1 | TCA AGT TTT CC | 24 | R$_6$G | H or —C(O)CH$_3$ | 48 |
| PPMO#18 | NDM-1 | TCC TTT TAT TC | 25 | TEG | (RXR)$_4$XB— | 45 |
| PPMO#19 | NDM-1 | TCA AGT TTT CC | 24 | TEG | (RXR)$_4$XB— | 45 |
| PPMO#36 | NDM-1 | TCC TTT TAT TC | 25 | TEG | R$_6$G | 48 |
| PPMO#37 | NDM-1 | GGCAATTCCAT | 50 | TEG | R$_6$G | 48 |

*The thymines (T) can be uracils (U);
**X is 6-aminohexanoic acid, B is beta-alanine, G is glycine and TEG is defined above.
***X is 6-aminohexanoic acid, B is beta-alanine, G is glycine, TEG is defined above, and a 5' CPP is linked through a pip-PDA moiety described above.

TABLE 3B

Exemplary Biofilm Formation Targeting AONs

| PMO Name | Target Gene | Targeting Sequence (TS)* | TS SEQ ID NO: | 5' Attachment*** | 3' Attachment** | CPP SEQ ID NO. |
|---|---|---|---|---|---|---|
| PPMO#20 | CsuE | TTA TAT TCA TGG | 26 | R$_6$G | H or —C(O)CH$_3$ | 48 |
| PPMO#21 | CsuE | TCA TGG CAA AG | 27 | (RXR)$_4$XB— | H or —C(O)CH$_3$ | 45 |

TABLE 3B-continued

Exemplary Biofilm Formation Targeting AONs

| PMO Name | Target Gene | Targeting Sequence (TS)* | TS SEQ ID NO: | 5' Attachment*** | 3' Attachment** | CPP SEQ ID NO. |
|---|---|---|---|---|---|---|
| PPMO#22 | CsuE | TTA TAT TCA TGG | 26 | (RXR)$_4$XB— | H or —C(O)CH$_3$ | 45 |
| PPMO#23 | CsuE | TTT CCT GTC AA | 28 | (RXR)$_4$XB— | H or —C(O)CH$_3$ | 45 |
| PPMO#24 | SecA | TTG CCA ACA TG | 29 | (RXR)$_4$XB— | H or —C(O)CH$_3$ | 45 |
| PPMO#25 | PglL | CAT TAC CCA AG | 30 | (RXR)$_4$XB— | H or —C(O)CH$_3$ | 45 |
| PPMO#26 | PilU1 | TTA AAA TCC AT | 31 | (RXR)$_4$XB— | H or —C(O)CH$_3$ | 45 |
| PPMO#27 | AlgZ | TAG GCA TCG AC | 32 | (RXR)$_4$XB— | H or —C(O)CH$_3$ | 45 |
| PPMO#28 | AlgU | AAA GCT CCT CT | 33 | (RXR)$_4$XB— | H or —C(O)CH$_3$ | 45 |
| PPMO#29 | LasR | AGG CCA TAG CG | 34 | (RXR)$_4$XB— | H or —C(O)CH$_3$ | 45 |
| PPMO#30 | FleR | TTA CTC CTG AA | 35 | (RXR)$_4$XB— | H or —C(O)CH$_3$ | 45 |
| PPMO#31 | PelF | TTC GGT CAT GT | 36 | (RXR)$_4$XB— | H or —C(O)CH$_3$ | 45 |

*The thymines (T) can be uracils (U);
**TEG is defined above.
***X is 6-aminohexanoic acid, B is beta-alanine, G is glycine and a 5' CPP is linked through a pip-PDA moiety described above.

TABLE 3C

Exemplary Essential Genes Targeting AONs

| PMO Name | Target Gene | Targeting Sequence (TS)* | TS SEQ ID NO: | 5' Attachment*** | 3' Attachment** | CPP SEQ ID NO. |
|---|---|---|---|---|---|---|
| PPMO#32 | RpoD | TCA TCT TTG CT | 37 | TEG | (RXR)$_4$XB— | 45 |
| PPMO#33 | PolB | AGT AAC TCC AC | 38 | (RXR)$_4$XB— | H or —C(O)CH$_3$ | 45 |

*The thymines (T) can be uracils (U);
**X is 6-aminohexanoic acid, B is beta-alanine, TEG is defined above.
***X is 6-aminohexanoic acid, B is beta-alanine, TEG is defined above and a 5' CPP is linked through a pip-PDA moiety described above.

II. Methods of Use and Formulations

Embodiments of the present disclosure include methods of using the antisense oligomers described herein to reduce the expression and activity of one or more bacterial virulence factors. Certain embodiments include methods of using the antisense oligomers to reduce replication, proliferation, virulence factors, or growth of bacteria, for example, to treat bacterial infections in a subject, either alone or in combination with one or more additional antimicrobial agents. In some instances, the antisense oligomers increase the susceptibility of the bacterium to antibiotics. Certain embodiments include methods of using the antisense oligomers described herein to reduce the formation or existence of bacterial biofilms, for instance, to treat bacterial infections in a subject, either alone or in combination with one or more additional antimicrobial agents.

Also included are pharmaceutical compositions comprising the antisense oligomers, typically in combination with a pharmaceutically-acceptable carrier. The methods provided herein can be practiced in vitro or in vivo.

For example, certain embodiments include methods of treating a bacterial infection in a subject, comprising administering to a subject in need thereof (e.g., subject having or at risk for having a bacterial infection) an antisense oligomer or pharmaceutical composition described herein. Also included are methods of reducing virulence and/or biofilm formation of a bacteria or bacterium which comprises a gene encoding a virulence factor, comprising contacting the bacteria or bacterium with an antisense oligomer described herein.

In some embodiments, the bacterium is selected from the genus *Escherichia*, *Acinetobacter*, *Klebsiella*, *Burkholderia*, and *Pseudomonas*.

*Escherichia* is a genus of Gram-negative, non-spore forming, facultatively anaerobic, rod-shaped bacteria from the family Enterobacteriaceae, and includes the species *Escherichia coli*, which is responsible for the vast majority of *Escherichia*-related pathogenesis.

*Acinetobacter* is a genus of Gram-negative bacteria belonging to the class of Gammaproteobacteria. Examples of clinically-relevant *Acinetobacter* complexes include the *Acinetobacter calcoaceticus-baumanii* complex (glucose-oxidizing nonhemolytic), *Acinetobacter iwoffii* (glucose-negative nonhemolytic), and *Acinetobacter haemolyticus* (hemolytic). Specific examples include *Acinetobacter baumannii*. *Acinetobacter baumannii* is a ubiquitous organism that has emerged over recent years to be a significant cause of hospital-acquired infections. It is all the more concerning given that *A. baumannii* has become one of the most antibiotic resistant Gram-negative pathogens that the medical community currently faces worldwide. The rapid increase in multidrug-resistance in *A. baumannii* has left few therapeutic choices for the treating physician. Older drugs such as colistin are now frequently used, although colistin-resistant strains have now emerged. *A. baumannii* can cause a variety of clinical infections, with pneumonia being one of the most frequent.

*Klebsiella* is a genus of non-motile, Gram-negative, oxidase-negative, rod-shaped bacteria with a prominent polysaccharide-based capsule. *Klebsiella* organisms can lead to a wide range of disease states, such as pneumonia, urinary tract infections, septicemia, meningitis, diarrhea, and soft tissue infections. The majority of human infections are caused by *Klebsiella pneumoniae* and *Klebsiella oxytoca*. *Klebsiella* has become increasingly drug resistant. A recent outbreak of *Klebsiella* infections at the National Institutes of Health Clinical Center illustrates the difficulty in treating patients with these infections and the complexities that institutions can face in trying to eradicate these strains from the hospital environment. The spread of carbapenem-resistant Enterobacteriaceae (CRE) (including *K. pneumoniae*) has happened rapidly worldwide, including in the U.S. where carbapenemase-producing CRE has now been reported in most states.

*Burkholderia* (previously part of *Pseudomonas*) refers to a group of near ubiquitous gram-negative, motile, obligately aerobic rod-shaped bacteria. These protobacteria include pathogenic bacteria such as *Burkholderia mallei*, responsible for glanders; *Burkholderia pseudomallei*, causative agent of melioidosis; and *Burkholderia cepacia*, a significant pathogen of pulmonary infections, for example, in subjects with cystic fibrosis (CF). *Burkholderia cepacia* (or *Burkholderia cepacia* complex) is a Gram-negative bacterium composed of many different sub-species, including, for example, *Burkholderia cenocepacia*, *Burkholderia multivorans*, *Burkholderia vietnamiensis*, *Burkholderia stabilis*, *Burkholderia anthina*, *Burkholderia pyrrocinia*, *Burkholderia dolosa*, and/or *Burkholderia ambifaria*.

*Pseudomonas* is a genus of Gram-negative aerobic gammaproteobacteria, belonging to the family Pseudomonadaceae. *Pseudomonas aeruginosa* is increasingly recognized as an emerging opportunistic pathogen of clinical relevance. *Pseudomonas aeruginosa* can cause a variety of infections in the hospital setting including VAP, bacteremia and wound infections in burn patients. In addition, it is the major pathogen associated with lung infections in cystic fibrosis. Eighty percent of CP patients are infected with *P. aeruginosa* by adulthood, and chronic lung infections with this pathogen are the primary cause of morbidity and mortality. In the CF patient, complete eradication of *P. aeruginosa* is rarely achieved. *P. aeruginosa* is naturally resistant to many antibiotics and is becoming resistant to those it was once sensitive to. Importantly, multi-drug resistant isolates of *P. aeruginosa* are now common in both CF and non-CF patients leaving virtually no therapeutic options. The formation of biofilm is a major virulence trait in *Pseudomonas*.

Thus, in some embodiments, the bacterium is any of the foregoing members of the genera *Escherichia*, *Acinetobacter*, *Klebsiella*, *Burkholderia*, and *Pseudomonas*. In specific embodiments, the bacterium is one or more of *Escherichia coli*, *Acinetobacter baumannii*, *Klebsiella pneumoniae*, *Burkholderia cepacia* (complex), or *Pseudomonas aeruginosa*.

In certain embodiments, the bacterium is multi-drug resistance (MDR) bacteria or bacterium. Multiple drug resistance (MDR), multi-drug resistance or multiresistance is a condition enabling disease-causing microorganisms (bacteria, viruses, fungi or parasites) to resist distinct antimicrobials such as antibiotics, antifungal drugs, antiviral medications, antiparasitic drugs, and others. In particular embodiments, the bacterium is extensively-drug resistant (XDR) or pan-drug resistant (PDR). In some embodiments, the bacterium is an extended-spectrum β-lactamase (ESBLs) producing Gram-negative bacteria, *Klebsiella pneumoniae* carbapenemase (KPC or KPC 1-4) producing Gram-negative bacteria, or a multi-drug-resistant gram negative rod (MDR GNR) MDRGN bacteria. In specific embodiments, the bacterium is MDR *Escherichia coli*, MDR *Acinetobacter baumannii*, MDR *Klebsiella pneumoniae*, MDR *Burkholderia cepacia* (complex), or MDR *Pseudomonas aeruginosa*.

As noted above, the bacteria or bacterium described herein typically comprise (e.g., encode) one or more virulence factors such as antibiotic resistance genes and/or biofilm formation genes. General examples of antibiotic resistance genes (and their related proteins) include beta-lactamases, which can enzymatically deactivate certain antimicrobial agents, and genes/proteins which increase the permeability or active efflux (pumping out) of an antimicrobial agent. Particular examples of antibiotic resistance genes include New Delhi metallo-beta-lactamase (NDM-1), resistance-nodulation-cell division (RND)-type multidrug efflux pump subunit AdeA (adeA), serine beta-lactamase (KPC or KPC 1-4), acridine resistance complex protein AcrA, acridine resistance complex protein AcrB, acridine resistance complex repressor protein AcrR, acridine resistance complex protein TolC, and outer membrane protein A (OmpA). In specific embodiments, the bacterium is *Escherichia coli*, *Acinetobacter baumannii*, or *Klebsiella pneumoniae*, which comprises or expresses at least one antibiotic resistance gene selected from NDM-1, AdeA, KPC, KPC 1-4, AcrA, AcrB, AcrR, TolC and OmpA.

Examples of biofilm formation genes (and their related proteins) include: cepI, cepR and suhB genes, for example, from *Burkholderia*; CsuE, SecA, PglL and PilU1 genes, for example, from *Acinetobacter baumannii*; AlgZ, AlgU, LasR, FleR and PelF genes, for example, from *Pseudomonas aeruginosa*. In particular embodiments, the bacterium comprises or expresses a cepI gene, which encodes an acylhomoserine lactone synthase. In some embodiments, the bacterium comprises or expresses a suhB gene, which encodes an inositol-1-monophosphate. In specific embodiments, the bacterium that comprises or expresses one more biofilm formation genes is a *Burkholderia* species, for example, *Burkholderia cepacia* or *Burkholderia cepacia* (complex). In some of these and related embodiments, the subject in need thereof is immunocompromised and has an underlying lung disease, such as cystic fibrosis (CF) or chronic granulomatous disease (CGD).

In some embodiments, the bacterium comprises or expresses a CsuE gene, which encodes a chaperone-usher pili assembly system protein. In some embodiments, the bacterium comprises or expresses a SecA gene, which encodes an ATPase associated with cell membrane transport. In some embodiments, the bacterium comprises or expresses a PglL gene. In some embodiments, the bacterium comprises or expresses a PilU1 gene. In specific embodiments, the bacterium that comprises or expresses one more biofilm formation genes is an *Acinetobacter* species, for example, *Acinetobacter baumannii*.

In some embodiments, the bacterium comprises or expresses an AlgZ gene, which encodes a protein associated with alginate biosynthesis. In some embodiments, the bacterium comprises or expresses an AlgU gene, which encodes a protein associated with alginate biosynthesis. In some embodiments, the bacterium comprises or expresses a LasR gene, which encodes a transcriptional activator protein. In some embodiments, the bacterium comprises or expresses a FleR gene, which encodes a transcriptional regulator of flagella expression. In some embodiments, the bacterium comprises or expresses the PelF gene, which encodes a polysaccharide biosynthesis protein. In specific embodiments, the bacterium that comprises or expresses one more biofilm formation genes is a *Pseudomonas* species, for example, *Pseudomonas aeruginosa*.

Examples of essential genes (and their related proteins) include: RpoD gene, for example, from *Acinetobacter baumannii* and PolB gene, for example, from *Pseudomonas aeruginosa*. In some embodiments, the bacterium comprises or expresses an RpoD gene, which encodes an RNA polymerase. In specific embodiments, the bacterium that comprises or expresses one more essential genes is a *Acinetobacter* species, for example, *Acinetobacter baumannii*. In some embodiments, the bacterium comprises or expresses a PolB gene, which encodes a DNA polymerase II. In specific embodiments, the bacterium that comprises or expresses one more biofilm formation genes is a *Pseudomonas* species, for example, *Pseudomonas aeruginosa*.

In some embodiments, the antisense oligomer reduces or inhibits the growth of the bacterium. For instance, in some embodiments, the antisense oligomer reduces growth of the bacterium by about or at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to a control (e.g., absence of the antisense oligomer, scrambled oligomer, prior to contacting with the oligomer), or by about or at least about 2, 3, 4, 5, 6, 7, 8, 9, 10, 15, 20, 25, 30, 35, 40, 45, 50, 55, 60, 65, 70, 75, 80, 85, 90, 95, or 100-fold or more (including all integers and ranges in between), relative to a control. Bacterial growth can be measured in vitro (see, e.g., the Examples) or in vivo. In some embodiments, as described herein, the antisense oligomer is employed in combination with one or more antimicrobial agents.

In some embodiments, the antisense oligomer reduces beta-lactamase (e.g., carbapenemase) activity in the periplasm of the bacterium by about or at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to a control, or by at least about 2, 3, 4, 5, 6, 7, 8, 9, 10, 15, 20, 25, 30, 35, 40, 45, 50, 55, 60, 65, 70, 75, 80, 85, 90, 95, or 100-fold or more (including all integers and ranges in between), relative to a control. In some embodiments, the antisense oligomer reduces meropenemase enzymatic activity in the periplasm of the bacterium. In particular embodiments, the antisense oligomer that reduces beta-lactamase (e.g., carbapenemase) activity is targeted against NDM-1, and the bacterium is an *Acinetobacter, Escherichia*, or *Klebsiella* species, for example, *Escherichia coli, Acinetobacter baumannii*, or *Klebsiella pneumoniae* which comprises or expresses NDM-1. These are exemplary bacterial species and it is expected that any bacterium expressing the NDM-1 gene is susceptible to the compounds and methods described herein. In particular embodiments, the antisense oligomer that reduces beta-lactamase (e.g., carbapenemase) activity is targeted against KPC or KPC1-4, and the bacterium is an *Acinetobacter, Escherichia*, or *Klebsiella* species, for example, *Escherichia coli, Acinetobacter baumannii*, or *Klebsiella pneumoniae* which comprises or expresses KPC or KPC 1-4. These are exemplary bacterial species and it is expected that any bacterium expressing the KPC or KPC 1-4 gene is susceptible to the compounds and methods described herein. Beta-lactamase (e.g., carbapenemase) activity can be measured according to routine techniques in the art.

In some embodiments, the antisense oligomer reduces multi-drug efflux pump activity in the bacterium by about or at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to a control, or by at least about 2, 3, 4, 5, 6, 7, 8, 9, 10, 15, 20, 25, 30, 35, 40, 45, 50, 55, 60, 65, 70, 75, 80, 85, 90, 95, or 100-fold or more (including all integers and ranges in between), relative to a control. In particular embodiments, the antisense oligomer that reduces multi-drug efflux pump activity is targeted against AcrA, AcrB, AcrR or TolC, and the bacterium is an *Acinetobacter, Escherichia*, or *Klebsiella* species, for example, *Escherichia coli, Acinetobacter baumannii*, or *Klebsiella pneumoniae* which comprises or expresses AcrA, AcrB, AcrR or TolC. These are exemplary bacterial species and it is expected that any bacterium expressing the AcrA, AcrB, AcrR or TolC gene is susceptible to the compounds and methods described herein. Multi-drug efflux pump activity can be measured according to routine techniques in the art.

In some embodiments, the antisense oligomer reduces porin activity in the bacterium by about or at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to a control, or by at least about 2, 3, 4, 5, 6, 7, 8, 9, 10, 15, 20, 25, 30, 35, 40, 45, 50, 55, 60, 65, 70, 75, 80, 85, 90, 95, or 100-fold or more (including all integers and ranges in between), relative to a control. In particular embodiments, the antisense oligomer that reduces porin activity is targeted against OmpA, and the bacterium is an *Acinetobacter, Escherichia*, or *Klebsiella* species, for example, *Escherichia coli, Acinetobacter baumannii*, or *Klebsiella pneumoniae* which comprises or expresses OmpA. These are exemplary bacterial species and it is expected that any bacterium expressing the OmpA gene is susceptible to the compounds and methods described herein. Porin activity can be measured according to routine techniques in the art.

In some embodiments, the antisense oligomer reduces biofilm formation and/or the levels of existing biofilm relative to a control (e.g., absence of the oligomer). For instance, in some embodiments, the antisense oligomer reduces biofilm formation and/or the levels of existing biofilm by at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to a control, or by at least about 2, 3, 4, 5, 6, 7, 8, 9, 10, 15, 20, 25, 30, 35, 40, 45, 50, 55, 60, 65, 70, 75, 80, 85, 90, 95, or 100-fold or more (including all integers and ranges in between), relative to a control. In particular embodiments, the antisense oligomer that reduces biofilm formation and/or the levels of existing biofilm is targeted against cepI, cepR, and/or suhB, and the bacterium is a *Burkholderia* species, for example, *Burkholderia cepacia* (complex) or a subspecies thereof (e.g., *Burkholderia cenocepacia, Burkholderia multivorans, Burkholderia vietnamiensis, Burkholderia stabilis, Burkholderia anthina, Burkholderia pyrrocinia, Burkholderia dolosa, Burkholderia ambifaria*), which comprises or expresses cepI, cepR and/or suhB. In particular embodiments, the antisense oligomer that reduces biofilm formation and/or the levels of existing biofilm is targeted against CsuE, SecA, Pg1L and/or PilU1, and the bacterium is a *Acinetobacter* species, for example, *Acinetobacter baumannii*, which comprises or expresses CsuE, SecA, Pg1L and/or PilU1. In particular embodiments, the antisense oligomer that reduces biofilm formation and/or the levels of existing biofilm is targeted against AlgZ, AlgU, LasR, FleR and/or PelF, and the bacterium is a *Pseudomonas* species, for example, *Pseudomonas aeruginosa*, which comprises or expresses AlgZ, AlgU, LasR, FleR and/or PelF. Biofilm formation and/or the levels of existing biofilm can be measured in vitro (see, e.g., the Examples) or in vivo.

In some embodiments, the methods are practiced in vivo, and comprise administering the antisense oligomer to a subject in need thereof, for example, a subject in need thereof that is infected or at risk for being infected by one or more of the bacteria or bacterium described herein. The antisense oligomers of the disclosure can thus be administered to subjects to treat (prophylactically or therapeutically) an infection by any of the bacteria or bacterium described herein. In conjunction with such treatment, pharmacogenomics (e.g., the study of the relationship between an individual's genotype/phenotype and that individual's response to a foreign compound or drug) may be considered. Differences in metabolism of therapeutics can lead to severe toxicity or therapeutic failure by altering the relation between dose and blood concentration of the pharmacologically active drug.

Thus, a physician or clinician may consider applying knowledge obtained in relevant pharmacogenomics studies in determining whether to administer a therapeutic agent as well as tailoring the dosage and/or therapeutic regimen of treatment with a therapeutic agent.

Effective delivery of the antisense oligomer to the target nucleic acid is one aspect of treatment. Routes of antisense oligomer delivery include, but are not limited to, various systemic routes, including oral and parenteral routes, e.g., intravenous, subcutaneous, intraperitoneal, and intramuscular, as well as inhalation, transdermal, and topical delivery. The antisense oligomer may be aerosolized for delivery. The appropriate route may be determined by one of skill in the art, as appropriate to the condition of the subject under treatment. Vascular or extravascular circulation, the blood or lymph system, and the cerebrospinal fluid are some non-limiting sites where the antisense oligomers may be introduced. Direct CNS delivery may be employed, for instance, intracerebral, intraventricular, or intrathecal administration may be used as routes of administration.

In certain embodiments, the antisense oligomers of the disclosure can be delivered by transdermal methods (e.g., via incorporation of the antisense oligomers into, e.g., emulsions, with such antisense oligomers optionally packaged into liposomes). Such transdermal and emulsion/liposome-mediated methods of delivery are described for delivery of antisense oligomers in the art, e.g., in U.S. Pat. No. 6,965,025, the contents of which are incorporated in their entirety by reference herein.

In certain embodiments, the antisense oligomers of this disclosure can be delivered by aerosolization. Advantages to administering medications to the lung as an aerosol include: a more rapid onset of action compared to oral therapy; high local concentration by delivery directly to the airways; needle-free systemic delivery of drugs with poor oral bioavailability; and pain- and needle-free delivery for drugs that require subcutaneous or intravenous injection. Traditional aerosol therapies with the lung as the target consist of short-acting β2-adrenergic agonists and long-acting β2-adrenergic agonists (LABA), anticholinergics, inhaled corticosteroids (ICSs), nonsteroidal antiinflammatories, antibiotics and mucolytics. Devices that deliver these drugs include pressurized metered-dose inhalers (pMDIs), used either alone, or attached to spacers, or valved holding chambers (VHCs), breathactuated (BA)-pMDIs, dry powder inhalers (DPIs), jet nebulizers, vibrating mesh nebulizers and soft mist inhalers. Well-established treatment guidelines for the management of asthma and chronic obstructive pulmonary disease (COPD) each recommend inhaled therapy as the primary route to administer these medications. Treatment guidelines for cystic fibrosis (CF) also include recommendations for inhalation of aerosolized medications.

The antisense oligomers described herein may also be delivered via an implantable device. Design of such a device is an art-recognized process, with, e.g., synthetic implant design described in, e.g., U.S. Pat. No. 6,969,400, the contents of which are incorporated by reference.

Antisense oligomers can be introduced into cells using art-recognized techniques (e.g., transfection, electroporation, fusion, liposomes, colloidal polymeric particles and viral and non-viral vectors as well as other means known in the art). The method of delivery selected will depend at least on the oligomer chemistry, the cells to be treated and the location of the cells and will be apparent to the skilled artisan. For instance, localization can be achieved by liposomes with specific markers on the surface to direct the liposome, direct injection into tissue containing target cells, specific receptor-mediated uptake, or the like.

As known in the art, antisense oligomers may be delivered using, e.g., methods involving liposome-mediated uptake, lipid conjugates, polylysine-mediated uptake, nanoparticle-mediated uptake, and receptor-mediated endocytosis, as well as additional non-endocytic modes of delivery, such as microinjection, permeabilization (e.g., streptolysin-O permeabilization, anionic peptide permeabilization), electroporation, and various non-invasive non-endocytic methods of delivery that are known in the art (see, e.g., Dokka and Rojanasakul, Advanced Drug Delivery Reviews 44:35-49, incorporated by reference in its entirety).

The antisense oligomers may be administered in any convenient vehicle or carrier which is physiologically and/or pharmaceutically acceptable. Such a composition may include any of a variety of standard pharmaceutically acceptable carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration. "Pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions The compounds (e.g., antisense oligomers, antimicrobial agents) described herein may generally be utilized as the free acid or free base. Alternatively, the compounds of this disclosure may be used in the form of acid or base addition salts. Acid addition salts of the free amino compounds of the present disclosure may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids.

Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" is intended to encompass any and all acceptable salt forms.

In addition, prodrugs are also included within the context of this disclosure. Prodrugs are any covalently bonded carriers that release a compound in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this disclosure wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the antisense oligomers of the disclosure. Further, in the case of a carboxylic acid (—COOH), esters may be employed, such as methyl esters, ethyl esters, and the like.

In some instances, liposomes may be employed to facilitate uptake of the antisense oligomer into cells (see, e.g., Williams, S. A., Leukemia 10(12):1980-1989, 1996; Lappalainen et al., Antiviral Res. 23:119, 1994; Uhlmann et al., antisense oligomers: a new therapeutic principle, Chemical Reviews, Volume 90, No. 4, 25 pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. Alternatively, the oligomers may be administered in microspheres or microparticles. (See, e.g., Wu, G. Y. and Wu, C. H., J. Biol. Chem. 262:4429-4432, 30 1987). Alternatively, the use of gas-filled microbubbles complexed with the antisense oligomers can enhance delivery to target tissues, as described in U.S. Pat. No. 6,245,747. Sustained release compositions may also be used. These may include semipermeable polymeric matrices in the form of shaped articles such as films or microcapsules.

In certain embodiments, the antisense oligomer is administered to a mammalian subject, e.g., human or domestic animal, exhibiting the symptoms of a bacterial infection (e.g., antibiotic resistance or MDR bacterial infection), in a suitable pharmaceutical carrier. In some aspects, the subject is a human subject, e.g., a patient diagnosed as having a bacterial infection. In particular embodiments, the antisense oligomer is contained in a pharmaceutically acceptable carrier, and is delivered orally. In some embodiments, the antisense oligomer is contained in a pharmaceutically acceptable carrier, and is delivered intravenously (i.v.).

In some embodiments, the antisense oligomer is administered in an amount and manner effective to result in a peak blood concentration of at least 200-400 nM antisense oligomer. Typically, one or more doses of antisense oligomer are administered, generally at regular intervals, for a period of about one to two weeks. Certain doses for oral administration are from about 1-1000 mg oligomer per 70 kg. In some cases, doses of greater than 1000 mg oligomer/patient may be necessary. For i.v. administration, some doses are from about 0.5 mg to 1000 mg oligomer per 70 kg. The antisense oligomer may be administered at regular intervals for a short time period, e.g., daily for two weeks or less. However, in some cases the antisense oligomer is administered intermittently over a longer period of time. Administration may be followed by, or concurrent with, administration of an antimicrobial (e.g., antibiotic) or other therapeutic treatment, as described herein. The treatment regimen may be adjusted (dose, frequency, route, etc.) as indicated, based on the results of immunoassays, other biochemical tests and physiological examination of the subject under treatment.

An effective in vivo treatment regimen using the antisense oligomers of the disclosure may vary according to the duration, dose, frequency and route of administration, as well as the condition of the subject under treatment (i.e., prophylactic administration versus administration in response to localized or systemic infection). Accordingly, such in vivo therapy will often include monitoring by tests appropriate to the particular type of disorder or bacterial infection under treatment, and corresponding adjustments in the dose or treatment regimen, in order to achieve an optimal therapeutic outcome.

Treatment may be monitored, e.g., by general indicators of disease known in the art. The efficacy of an in vivo administered antisense oligomer of the disclosure may be determined from biological samples (tissue, blood, urine etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of a mutant mRNA in relation to a reference normal mRNA or protein as determined by standard techniques such as RT-PCR, Northern blotting, ELISA or Western blotting.

III. Combination Therapies

Certain embodiments include combination therapies, for example, the administration of antisense oligomers in combination with antimicrobial agents such as antibiotics. Combination therapies can be employed, for example, to increase the sensitivity or susceptibility of a given bacteria to one or more antimicrobial agents, and thereby improve the therapeutic outcome (e.g., resolution of the infection). Likewise, certain combination therapies can be employed, for example, to reduce or reverse the antibiotic resistance of a given bacteria to one or more antimicrobial agents. In particular embodiments, the antisense oligomer reduces the minimum inhibitory concentration (MIC) of an antibiotic against a bacterium. Also included are pharmaceutical compositions, as described herein, which comprise an antisense oligomer and an antimicrobial agent such as antibiotic.

In some embodiments, the antisense oligomer and the antimicrobial agent are administered separately. In certain embodiments, the antisense oligomer and the antimicrobial agent are administered sequentially. In some embodiments, the antisense oligomer and the antimicrobial agent are administered concurrently, for example, as part of the same or different pharmaceutical composition.

Examples of antimicrobial agents (e.g., antibiotics) that can be administered in combination with an antisense oligomer include beta-lactam antibiotics such as carbapenems, penicillin and penicillin derivatives (or penams), cephalosporins (e.g., Cefacetrile (cephacetrile), Cefadroxil (cefadroxyl; Duricef), Cephalexin (cefalexin; Keflex), Cefaloglycin (cephaloglycin), Cefalonium (cephalonium), Cefaloridine (cephaloradine), Cefalotin (cephalothin; Keflin), Cefapirin (cephapirin; Cefadryl), Cefatrizine, Cefazaflur, Cefazedone, Cefazolin (cephazolin; Ancef, Kefzol), Cefradine (cephradine; Velosef), Cefroxadine, Ceftezole, Cefaclor (Cedor, Distaclor, Keflor, Ranidor), Cefonicid (Monocid), Cefprozil (cefproxil; Cefzil), Cefuroxime (Zefu, Zinnat, Zinacef, Ceftin, Biofuroksym, Xorimax), Cefuzonam, Cefmetazole, Cefotetan, Cefoxitin, loracarbef (Lorabid); Cephamycins: cefbuperazone, cefmetazole (Zefazone), cefminox, cefotetan (Cefotan), cefoxitin (Mefoxin), Cefotiam (Pansporin), Cefcapene, Cefdaloxime, Cefdinir (Sefdin, Zinir, Omnicef, Kefnir), Cefditoren, Cefetamet, Cefixime (Fixx, Zifi, Suprax), Cefmenoxime, Cefodizime, Cefotaxime (Claforan), Cefovecin (Convenia), Cefpimizole, Cefpodoxime (Vantin, PECEF), Cefteram, Ceftibuten (Cedax), Ceftiofur, Ceftiolene, Ceftizoxime (Cefizox), Ceftriaxone (Rocephin), Cefoperazone (Cefobid), Ceftazidime (Meezat, Fortum, Fortaz), latamoxef (moxalactam), Cefdidine, cefepime (Maxipime), cefluprenam, cefoselis, Cefozopran, Cefpirome (Cefrom), Cefquinome, flomoxef, Ceftobiprole, Ceftaroline, Cefaloram, Cefaparole, Cefcanel, Cefedrolor, Cefempidone, Cefetrizole, Cefivitril, Cefmatilen, Cefmepidium, Cefoxazole, Cefrotil, Cefsumide, Ceftioxide, Cefuracetime), and monobactams (e.g., aztreonam, tigemonam, nocardin A, tabtoxin); aminoglycosides such as tobramycin, gentamicin, kanamycin a, amikacin, dibekacin, sisomicin, netilmicin, neomycin B, neomycin C, neomycin E (paromomycin), and streptomycin; tetracyclines such as tetracycline, chlortetracycline, oxytetracycline, demeclocycline, lymecycline, meclocycline, methacycline, minocycline, rolitetracycline, and doxycyline; sulfonamides such as sulfacetamide, sulfadiazine, sulfadimidine, sulfafurazole, sulfisomidine, sulfadoxine, sulfamethoxazole, sulfamoxole, sulfadimethoxine, sulfamethoxypyridazine, sulfametoxydiazine, sulfadoxine, and sulfametopyrazine; quinolones such as cinoxacin, nalidixic acid, oxolinic acid (Uroxin), piromidic acid (Panacid), pipemidic acid (Dolcol) rosoxacin (Eradacil), ciprofloxacin (Alcipro.Ciprobay, Cipro, Ciproxin, ultracipro), enoxacin (Enroxil, Penetrex), fleroxacin (Megalone, Roquinol), lomefloxacin (Maxaquin), nadifloxacin (Acuatim, Nadoxin, Nadixa), norfloxacin (Lexinor, Noroxin, Quinabic, Janacin), ofloxacin (Floxin, Oxaldin, Tarivid), pefloxacin (Peflacine), rufloxacin (Uroflox), balofloxacin (Baloxin), grepafloxacin (Raxar), levofloxacin (Cravit, Levaquin, Tavanic), pazufloxacin (Pasil, Pazucross), sparfloxacin (Zagam), temafloxacin (Omniflox), tosufloxacin (Ozex, Tosacin), dinafloxacin, gatifloxacin (Zigat, Tequin) (Zymar-opth.), gemifloxacin (Factive), moxifloxacin (Acflox Woodward, Avelox,Vigamox, sitafloxacin (Gracevit), trovafloxacin (Trovan), prulifloxacin (Quisnon); oxazolidinones such as eperezolid, linezolid, posizolid, radezolid, ranbezolid, sutezolid, and tedizolid; polymyxins such as polysporin, neosporin, polymyxin B, polymyxin E (colistin); rifamycins such as rifampicin or rifampin, rifabutin, rifapentine, and rifaximin; lipiarmycins such as fidaxomicin; macrolides such as azithromycin, clarithromycin, dirithromycin, erythromycin, roxithromycin, telithromycin, carbomycin A, josamycin, kitasamycin, midecamycin/midecamycin acetate, oleandomycin, solithromycin, spiramycin, and troleandomycin; lincosamides such as lincomycin, clindamycin, and pirlimycin; cyclic lipopeptides such as daptomycin; glycopeptides such as vancomycin and teichoplanin; glycylcyclines such as tigecycline. Thus, any one or more of the foregoing antibiotics can be combined with any of the antisense oligomers described herein, for the treatment of any of the bacteria described herein.

In some embodiments, the antimicrobial agent is a beta-lactam antibiotic, as described herein. In certain of these and related embodiments, the bacterium comprises or expresses a beta-lactamase such as NDM-1, KPC or KPC1-4, and the antisense oligomer is targeted against the beta-lactamase. In particular embodiments, the antimicrobial agent is a carbapenem. Examples of carbapenems include meropenem, imipenem, ertapenem, doripenem, panipenem, biapenem, razupenem, tebipenem, lenapenem, and tomopenem. In certain of these and related embodiments, the bacterium comprises or expresses a carbapenemase such as NDM-1, KPC or KPC 1-4, and the antisense oligomer is targeted against the carbapenemase. In specific embodiments, the bacterium is *Escherichia coli, Acinetobacter baumannii*, or *Klebsiella pneumoniae*.

In some embodiments, the antimicrobial agent is an aminoglycoside such as tobramycin or gentamicin or a tetracycline, as described herein. In some of these and related embodiments, the bacterium comprises or expresses the antibiotic resistance gene adeA, and the antisense oligomer is targeted against the antibiotic resistance gene. In specific embodiments, the bacterium is *Escherichia coli, Acinetobacter baumannii*, or *Klebsiella pneumoniae*.

In some embodiments, the antimicrobial agent can be any antibiotic, such as, but not limited to, beta-lactams, aminoglycosides, tetracyclines, sulfonamides, quinolones, oxazolidinones, polymyxins, rifamycins, macrolides, lincosamides, cyclic lipopeptides, glycopeptides, glycylcyclines, or other antibiotics, as described herein. In certain of these and related embodiments, the bacterium comprises or expresses a porin such as OmpA, and the antisense oligomer is targeted against the porin. In particular embodiments, the antimicrobial agent comprises Clindamycin, Piperacillin-tazobactam, Doxycycline, Chloramphenicol, Fusidic acid, Oxacillin, Erythromycin and/or Trimethoprim.

In some embodiments, the antimicrobial agent is can be any antibiotic, such as, but not limited to, beta-lactams, aminoglycosides, tetracyclines, sulfonamides, quinolones, oxazolidinones, polymyxins, rifamycins, macrolides, lincosamides, cyclic lipopeptides, glycopeptides, glycylcyclines, or other antibiotics, as described herein. In certain of these and related embodiments, the bacterium comprises or expresses a protein associated with a multi-drug efflux pump such as AcrA, AcrB, AcrR or TolC, and the antisense oligomer is targeted against the protein associated with a multi-drug efflux pump or the function of a multi-drug efflux pump. In particular embodiments, the antimicrobial agent comprises Clindamycin, Piperacillin-tazobactam, Doxycycline, Chloramphenicol, Fusidic acid, Oxacillin, Erythromycin and/or Trimethoprim.

In certain embodiments, the antimicrobial agent includes one or more of ceftazidime, doxycycline, piperacillin, meropenem, chloramphenicol, and/or co-trimoxazole (trimethoprim/sulfamethoxazole). In some of these and related embodiments, the bacterium is a *Burkholderia* species that comprises or expresses one or more biofilm formation genes such as ceph cepR, and/or suhB, and the antisense oligomer is targeted against the biofilm formation gene(s). In specific embodiments, the bacterium is *Burkholderia cepacia* or a

*Burkholderia cepacia* complex. In specific embodiments, the subject is immunocompromised and has an underlying lung disease, such as cystic fibrosis (CF) or chronic granulomatous disease (CGD).

In certain embodiments, the antimicrobial agent includes one or more of ceftazidime, doxycycline, piperacillin, minocycline, meropenem, chloramphenicol, and/or co-trimoxazole (trimethoprim/sulfamethoxazole). In some of these and related embodiments, the bacterium is a *Acinetobacter* species that comprises or expresses one or more biofilm formation genes such as CsuE, SecA, Pg1L, and/or PilU1, and the antisense oligomer is targeted against the biofilm formation gene(s). In specific embodiments, the bacterium is *Acinetobacter baumannii*.

In certain embodiments, the antimicrobial agent includes one or more of ceftazidime, doxycycline, piperacillin, minocycline, meropenem, chloramphenicol, and/or co-trimoxazole (trimethoprim/sulfamethoxazole). In some of these and related embodiments, the bacterium is a *Pseudomonas* species that comprises or expresses one or more biofilm formation genes such as AlgZ, AlgU, LasR, FleR and/or PelF, and the antisense oligomer is targeted against the biofilm formation gene(s). In specific embodiments, the bacterium is *Pseudomonas aeruginosa*.

In certain embodiments, the antimicrobial agent includes one or more of ceftazidime, doxycycline, piperacillin, minocycline, meropenem, chloramphenicol, and/or co-trimoxazole (trimethoprim/sulfamethoxazole). In some of these and related embodiments, the bacterium is a *Acinetobacter* species that comprises or expresses one or more essential genes such as RpoD, and the antisense oligomer is targeted against the essential gene. In specific embodiments, the bacterium is *Acinetobacter baumannii*.

In certain embodiments, the antimicrobial agent includes one or more of ceftazidime, doxycycline, piperacillin, minocycline, meropenem, chloramphenicol, and/or co-trimoxazole (trimethoprim/sulfamethoxazole). In some of these and related embodiments, the bacterium is a *Pseudomonas* species that comprises or expresses one or more essential genes such as PolB, and the antisense oligomer is targeted against the essential gene. In specific embodiments, the bacterium is *Pseudomonas aeruginosa*.

In some embodiments, the antisense oligomer increases the sensitivity of a given bacteria to the antimicrobial agent, relative to the antimicrobial agent alone. For example, in certain embodiments, the antisense oligomer increases the sensitivity of the bacterium to the antimicrobial agent by increasing the bactericidal (cell-killing) and/or bacteriostatic (growth-slowing) activity of the antimicrobial agent against the bacterium being targeted, relative to the antimicrobial agent alone. In particular embodiments, the antisense increases the sensitivity by about or at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to the antimicrobial agent alone, or by about or at least about 2, 3, 4, 5, 6, 7, 8, 9, 10, 15, 20, 25, 30, 35, 40, 45, 50, 55, 60, 65, 70, 75, 80, 85, 90, 95, or 100-fold or more (including all integers and ranges in between), relative to the antimicrobial agent alone.

In some embodiments, the antisense oligomer reduces the minimum inhibitory concentration (MIC) of an antimicrobial agent against the bacterium being targeted, relative to the antimicrobial agent alone. The "minimum inhibitory concentration" or "MIC" refers to the lowest concentration of an antimicrobial agent that will inhibit the visible growth of a microorganism after overnight (in vitro) incubation. Minimum inhibitory concentrations are important in diagnostic laboratories to confirm resistance of microorganisms to an antimicrobial agent and also to monitor the activity of new antimicrobial agents. The MIC is generally regarded as the most basic laboratory measurement of the activity of an antimicrobial agent against a bacterial organism. Thus, in certain embodiments, the oligomer reduces the minimum inhibitory concentration (MIC) of an antimicrobial agent against the bacterium by at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to the antimicrobial agent alone. In certain embodiments, the oligomer reduces the minimum inhibitory concentration (MIC) of an antimicrobial agent against the bacterium by about or at least about 2, 3, 4, 5, 6, 7, 8, 9, 10, 15, 20, 25, 30, 35, 40, 45, 50, 55, 60, 65, 70, 75, 80, 85, 90, 95, or 100-fold or more (including all integers and ranges in between), relative to the antimicrobial agent alone.

In some embodiments, the antisense oligomer that increases the sensitivity or reduces the MIC is targeted against NDM-1, the bacterium is *Escherichia coli, Acinetobacter baumannii*, or *Klebsiella pneumoniae* that comprises or expresses NDM-1, and the antimicrobial agent is a carbapenem such as meropenem, imipenem, ertapenem, doripenem, panipenem, biapenem, razupenem, tebipenem, lenapenem, or tomopenem.

In some embodiments, the antisense oligomer that increases the sensitivity or reduces the MIC is targeted against KPC or KPC 1-4, the bacterium is *Escherichia coli, Acinetobacter baumannii*, or *Klebsiella pneumoniae* that comprises or expresses KPC or KPC 1-4, and the antimicrobial agent is a carbapenem such as meropenem, imipenem, ertapenem, doripenem, panipenem, biapenem, razupenem, tebipenem, lenapenem, or tomopenem.

In some embodiments, the antisense oligomer that increases the sensitivity or reduces the MIC is targeted against OmpA, the bacterium is *Escherichia coli, Acinetobacter baumannii*, or *Klebsiella pneumoniae* that comprises or expresses OmpA, and the antimicrobial agent is any antibiotic, such as, but not limited to, beta-lactams, aminoglycosides, tetracyclines, sulfonamides, quinolones, oxazolidinones, polymyxins, rifamycins, macrolides, lincosamides, cyclic lipopeptides, glycopeptides, glycylcyclines, or other antibiotics, as described herein. In particular embodiments, the antimicrobial agent comprises Clindamycin, Piperacillin-tazobactam, Doxycycline, Chloramphenicol, Fusidic acid, Oxacillin, Erythromycin and/or Trimethoprim.

In some embodiments, the antisense oligomer that increases the sensitivity or reduces the MIC is targeted against AcrA, AcrB, AcrR or TolC, the bacterium is *Escherichia coli, Acinetobacter baumannii*, or *Klebsiella pneumoniae* that comprises or expresses AcrA, AcrB, AcrR or TolC, and the antimicrobial agent is any antibiotic, such as, but not limited to, beta-lactams, aminoglycosides, tetracyclines, sulfonamides, quinolones, oxazolidinones, polymyxins, rifamycins, macrolides, lincosamides, cyclic lipopeptides, glycopeptides, glycylcyclines, or other antibiotics, as described herein. In particular embodiments, the antimicrobial agent comprises Clindamycin, Piperacillin-tazobactam, Doxycycline, Chloramphenicol, Fusidic acid, Oxacillin, Erythromycin and/or Trimethoprim.

In particular embodiments, the antisense oligomer that increases the sensitivity or reduces the MIC is targeted against adeA, the bacterium is *Escherichia coli, Acinetobacter baumannii*, or *Klebsiella pneumoniae* that comprises or expresses adeA, and the antimicrobial agent is an aminoglycoside antibiotic (e.g., tobramycin, gentamicin, kanamycin a, amikacin, dibekacin, sisomicin, netilmicin, neomycin B, neomycin C, neomycin E (paromomycin), streptomycin), a tetracycline antibiotic (e.g., tetracycline, chlortetracycline, oxytetracycline, demeclocycline, lymecycline, meclocycline, methacycline, minocycline, rolitetracycline, doxycyline), or a β-lactam antibiotic (e.g., carbapenem, penicillin derivative (penam), cephalosporin (cephem), monobactam).

In particular embodiments, the antisense oligomer that increases the sensitivity or reduces the MIC is targeted against cepl, the bacterium is a *Burkholderia* species, for example, *Burkholderia cepacia* (complex) or a sub-species thereof (e.g., *Burkholderia cenocepacia, Burkholderia multivorans, Burkholderia vietnamiensis, Burkholderia stabilis, Burkholderia anthina, Burkholderia pyrrocinia, Burkholderia dolosa, Burkholderia ambifaria*), which comprises or expresses cepl, and the antimicrobial agent is selected from one or more of ceftazidime, doxycycline, piperacillin, meropenem, chloramphenicol, and co-trimoxazole (trimethoprim/sulfamethoxazole).

In particular embodiments, the antisense oligomer that increases the sensitivity or reduces the MIC is targeted against suhB, the bacterium is a *Burkholderia* species, for example, *Burkholderia cepacia* (complex) or a sub-species thereof (e.g., *Burkholderia cenocepacia, Burkholderia multivorans, Burkholderia vietnamiensis, Burkholderia stabilis, Burkholderia anthina, Burkholderia pyrrocinia, Burkholderia dolosa, Burkholderia ambifaria*), which comprises or expresses suhB, and the antimicrobial agent is selected from one or more of ceftazidime, doxycycline, piperacillin, meropenem, chloramphenicol, and co-trimoxazole (trimethoprim/sulfamethoxazole).

In particular embodiments, the antisense oligomer that increases the sensitivity or reduces the MIC is targeted against CsuE, SecA, Pg1L or PilU1, the bacterium is an *Acinetobacter* species, for example, *Acinetobacter baumannii*, which comprises or expresses CsuE, SecA, Pg1L or PilU1, and the antimicrobial agent is selected from one or more of ceftazidime, doxycycline, piperacillin, minocycline, meropenem, chloramphenicol, and co-trimoxazole (trimethoprim/sulfamethoxazole).

In particular embodiments, the antisense oligomer that increases the sensitivity or reduces the MIC is targeted against AlgZ, AlgU, LasR, FleR or PelF, the bacterium is a *Pseudomonas* species, for example, *Pseudomonas aeruginosa*, which comprises or expresses AlgZ, AlgU, LasR, FleR or PelF, and the antimicrobial agent is selected from one or more of ceftazidime, doxycycline, piperacillin, minocycline, meropenem, chloramphenicol, and co-trimoxazole (trimethoprim/sulfamethoxazole).

In particular embodiments, the antisense oligomer that increases the sensitivity or reduces the MIC is targeted against RpoD, the bacterium is an *Acinetobacter* species, for example, *Acinetobacter baumannii*, which comprises or expresses RpoD, and the antimicrobial agent is selected from one or more of ceftazidime, doxycycline, piperacillin, minocycline, meropenem, chloramphenicol, and co-trimoxazole (trimethoprim/sulfamethoxazole).

In particular embodiments, the antisense oligomer that increases the sensitivity or reduces the MIC is targeted against PolB, the bacterium is a *Pseudomonas* species, for example, *Pseudomonas aeruginosa*, which comprises or expresses PolB, and the antimicrobial agent is selected from one or more of ceftazidime, doxycycline, piperacillin, minocycline, meropenem, chloramphenicol, and co-trimoxazole (trimethoprim/sulfamethoxazole).

IV. Treatment Monitoring Methods

The efficacy of a given therapeutic regimen involving the methods described herein may be monitored, for example, by general indicators of bacterial infection, such as complete blood count (CBC), nucleic acid detection methods, immunodiagnostic tests, or bacterial culture.

In some aspects, identification and monitoring of bacterial infection involves one or more of (1) nucleic acid detection methods, (2) serological detection methods, i.e., conventional immunoassay, (3) culture methods, and (4) biochemical methods. Such methods may be qualitative or quantitative.

Nucleic acid probes may be designed based on publicly available bacterial nucleic acid sequences, and used to detect target genes or metabolites (i.e., toxins) indicative of bacterial infection, which may be specific to a particular bacterial type, e.g., a particular species or strain, or common to more than one species or type of bacteria (i.e., Gram positive or Gram negative bacteria). Nucleic amplification tests (e.g., PCR) may also be used in such detection methods.

Serological identification may be accomplished using a bacterial sample or culture isolated from a biological specimen, e.g., stool, urine, cerebrospinal fluid, blood, etc. Immunoassay for the detection of bacteria is generally carried out by methods routinely employed by those of skill in the art, e.g., ELISA or Western blot. In addition, monoclonal antibodies specific to particular bacterial strains or species are often commercially available.

Culture methods may be used to isolate and identify particular types of bacteria, by employing techniques including, but not limited to, aerobic versus anaerobic culture, growth and morphology under various culture conditions. Exemplary biochemical tests include Gram stain (Gram, 1884; Gram positive bacteria stain dark blue, and Gram negative stain red), enzymatic analyses, and phage typing.

It will be understood that the exact nature of such diagnostic, and quantitative tests as well as other physiological factors indicative of bacterial infection will vary dependent upon the bacterial target, the condition being treated and whether the treatment is prophylactic or therapeutic.

In cases where the subject has been diagnosed as having a particular type of bacterial infection, the status of the bacterial infection is also monitored using diagnostic techniques typically used by those of skill in the art to monitor the particular type of bacterial infection under treatment.

The PMO or PPMO treatment regimen may be adjusted (dose, frequency, route, etc.), as indicated, based on the results of immunoassays, other biochemical tests and physiological examination of the subject under treatment.

From the foregoing, it will be appreciated how various objects and features of the disclosure are met. The method provides an improvement in therapy against bacterial infection, for example, multi-drug resistant (MDR) bacteria and/or biofilm-forming bacteria, using anti-virulence antisense oligomers to achieve enhanced cell uptake and anti-bacterial action. As a result, drug therapy is more effective and less expensive, both in terms of cost and amount of compound required.

One exemplary of the disclosure is that compounds effective against virtually any pathogenic bacterial can be readily designed and tested, e.g., for rapid response against new drug-resistant strains.

The following examples are intended to illustrate but not to limit the disclosure. Each of the patent and non-patent references referred to herein is incorporated by reference in its entirety.

EXAMPLES

Example 1

Development of Genus- and Gene-Specific PPMOs Against Specific Virulence Genes in the Multidrug-Resistant Pathogens *Acinetobacter baumannii* and *Pseudomonas aeruginosa*

Figure 3:
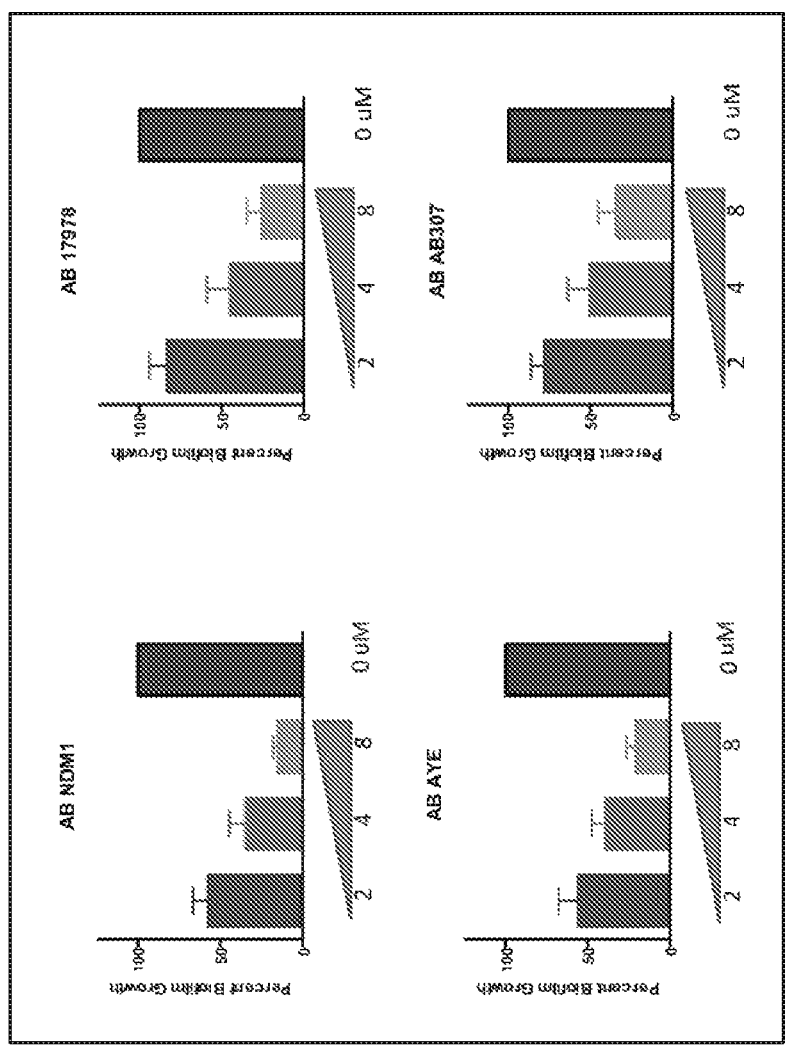
FIG. 3 shows reduction of biofilm in *Acinetobacter* spp. is dose-dependent. *Acinetobacter* biofilms were grown in the presence or absence of a CsuE PPMO for 20 hours. Concentrations of PPMO tested included 8 µM (green bars), 4 µM (red bars), 2 µM (blue bars) or no PPMO (black bars). Strains included AB NDM-1, AB AYE, AB 17978 and AB AB307. Reduction in biofilm formation was dose-dependent as seen in all strains tested.

Given the importance that biofilm plays in pathogenesis of infection, various biofilm or quorum-sensing genes were targets for PPMO development. While a number of PPMO targets were created and tested for their ability to inhibit *Acinetobacter* biofilm formation, the PPMO designed against CsuE was found to be most potent with over 83% of strains tested having a 50% or greater reduction in biofilm at a concentration of 8 µM (FIG. 2). This protein has been previously shown to play a role in attachment to surfaces and the development of biofilm. Most of the strains tested had a significantly greater reduction in biofilm formation at the target 8 µM concentration given as a single dose. Importantly for the development of PPMOs, activity is not linked to the underlying level of antibiotic resistance that a particular strain possesses. PPMO activity has been demonstrated in multidrug-resistant strains (such as *A. baumannii* AYE; FIG. 2) to the same or greater degree as drug-sensitive strains. The reduction in biofilm was frequently significantly greater than 50% and showed a dose-dependent response (FIG. 3). For example, in an NDM-1 positive *A. baumannii* strain (AB NDM-1) there was a greater than 80% reduction in biofilm at a concentration of 8 µM. Similar findings were observed in *A. baumannii* AYE, and these strains had a greater than 50% reduction in biofilm at 4 µM.

Figure 4:
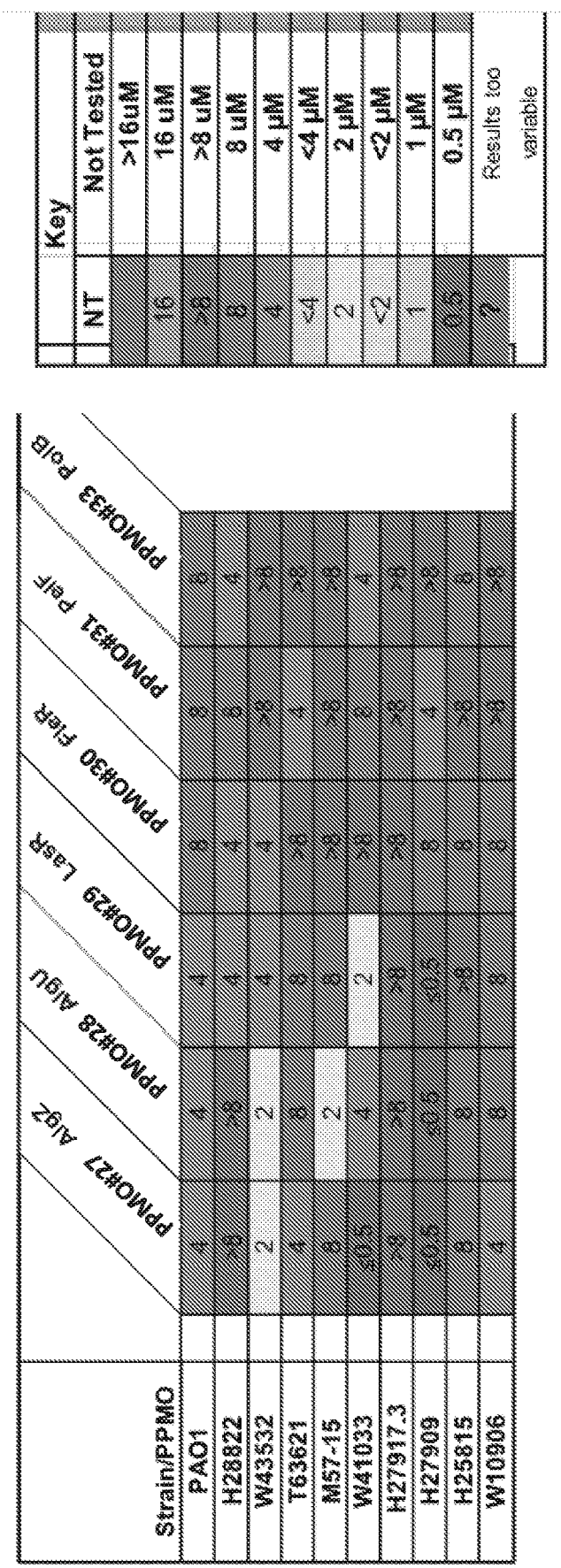
FIG. 4 shows that PPMOs prevent formation of biofilm in *Pseudomonas aeruginosa*. Strains were grown on MSEC biofilm plates for 18 hours in the presence of PMBN at 2 µg/ml and the PPMO, a scrambled PPMO or nothing. The numbers in each cell represent the concentration of PPMO that reduced biofilm by 50% or greater.

For *Pseudomonas aeruginosa*, genes that were known to be involved in biofilm and quorum sensing were also targeted. Polymyxin B nonapeptide (PMBN) was used at sub-inhibitory concentrations to enhance delivery of PPMOs in *Pseudomonas*. PPMOs in both standard genome sequenced laboratory strains (such as PAO1) as well as in clinical multidrug-resistant strains from patients with CF were tested. FIG. 4 shows the heatmap of the lead PPMOs. For *Pseudomonas*, there were 3 potential leads targeting the genes AlgZ, AlgU and LasR. These three gene targets have been shown previously to be important in the formation of biofilm, and the results developing PPMOs against these targets confirm this. 80% of strains tested had at least a 50% reduction in biofilm at 18 hours compared to no treatment. Concentrations needed to inhibit biofilm by at least 50% ranged from 8 µM to ≤0.5 µM. Scrambled sequence PPMOs did not significantly alter biofilm formation nor did PMBN alone.

Figure 5:
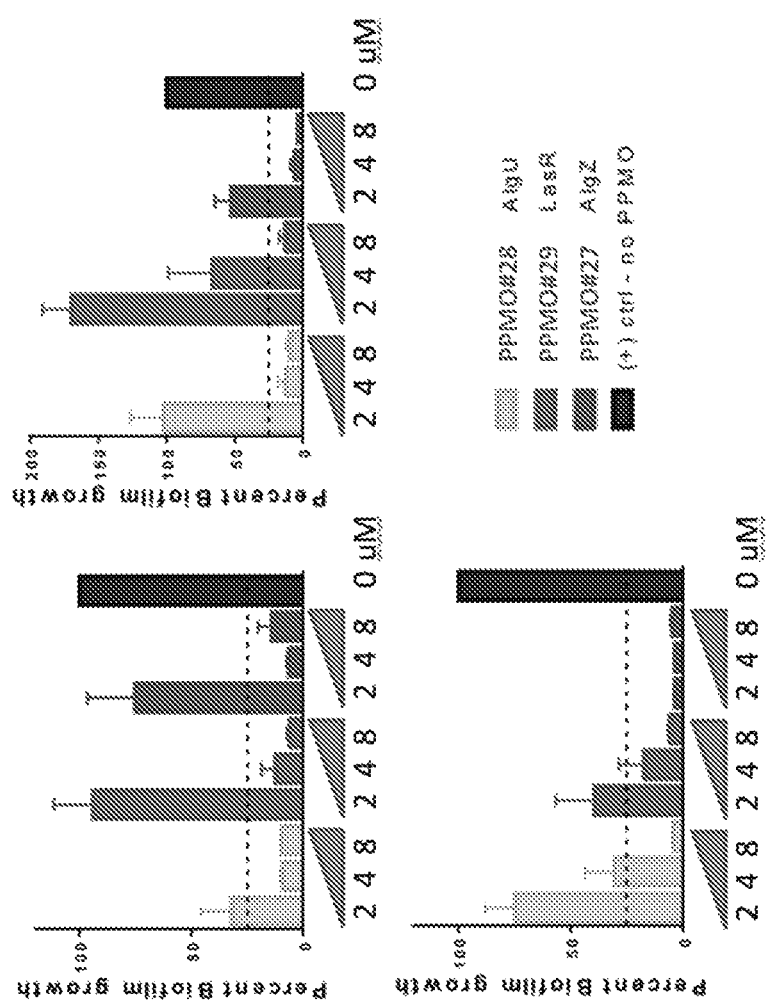
FIG. 5 shows that reduction of biofilm in *Pseudomonas aeruginosa* is dose-dependent. *Pseudomonas* biofilms were grown in the presence or absence of PPMOs (as indicated). Biofilms were grown for 18 hours and then stained with crystal violet. Three strains were tested with multiple PPMO doses as shown. Percent reduction compared to no PPMO control is shown.
Figure 6:
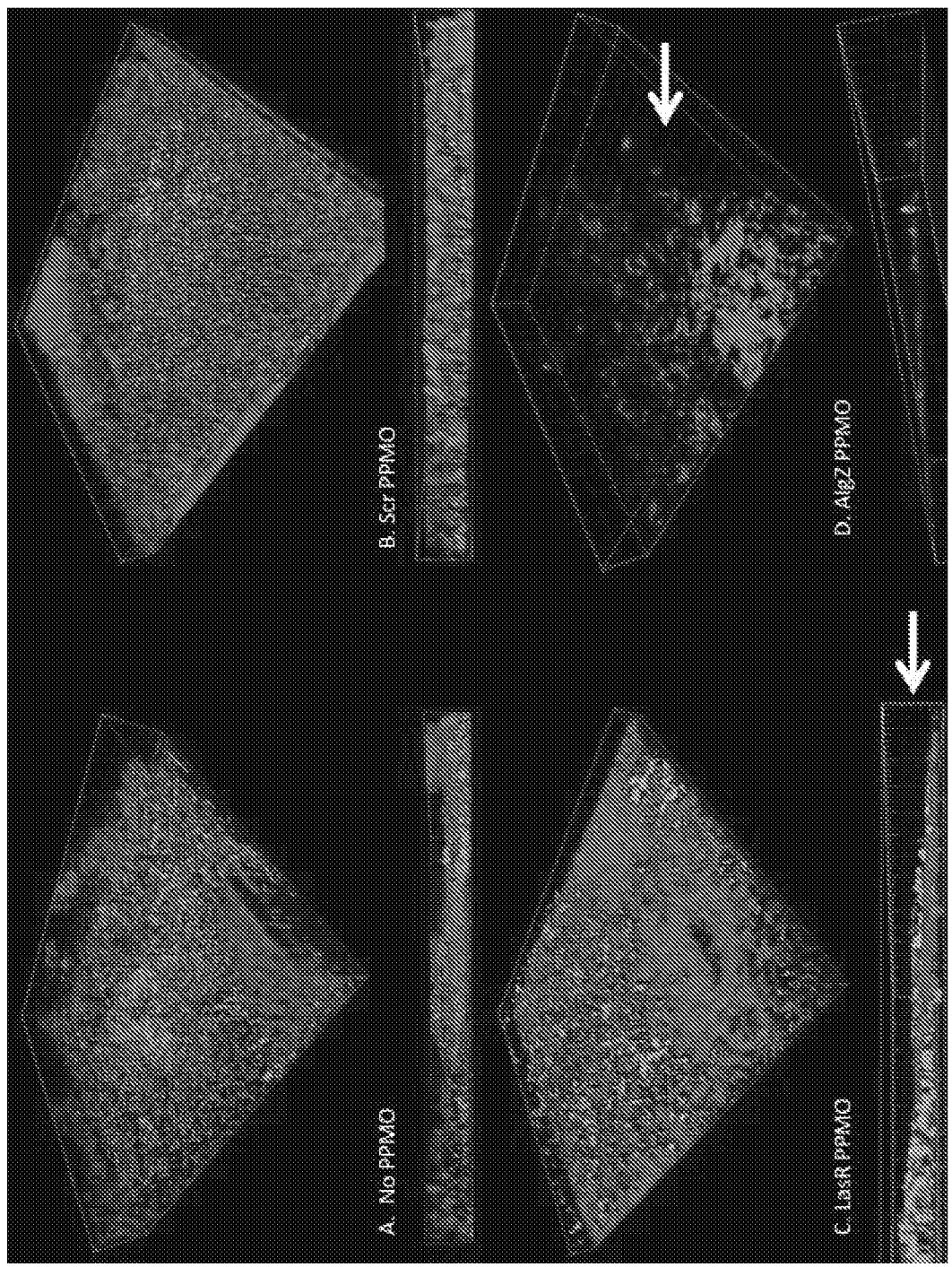
FIGS. 6A-6D show confocal microscopy demonstrating reduction of biofilm in *Pseudomonas aeruginosa* treated with the LasR PPMO#29 or AlgZ PPMO#27. GFP-PAO1 was grown for 18 hours in the presence of sub-inhibitory concentrations of PMBN alone (FIG. 6A), Ser PPMO+PMBN (FIG. 6B), LasR PPMO#29+PMBN (FIG. 6C) or AlgZ PPMO#27+PMBN (FIG. 6D). PPMOs were tested at 8 µM. Biofilm is shown in red and PAO1 in green. While PAO1 alone or with Ser PPMO displays robust biofilm formation, PAO1 with LasR PPMO#29 or PAO1 with AlgZ PPMO#27 show a substantial decrease in biofilm mass (white arrows).

As was seen in *Acinetobacter*, the reduction in biofilm was dose-dependent (FIG. 5). In 3 strains that were tested, the AlgZ PPMO#27 had a greater that 75% reduction in biofilm at both 4 and 8 µM. The LasR PPMO#29 and AlgU PPMO#28 also demonstrated a significantly larger reduction in biofilm at 8 µM that was greater than 50%.

MSEC pegs and confocal microscopy can be used to visualize the biofilms themselves. An example of this is shown in FIGS. 6A-6D, where a GFP-expressing *P. aeruginosa* PAO1 strain and a stain for biofilm were used to demonstrate the activity of a couple of the lead PPMOs. As can be seen in FIGS. 6A-6D, in the presence of PMBN alone (FIG. 6A) or the Scrambled PPMO (FIG. 6B), robust and thick biofilm is formed at 18 hours. However, when incubated with either the LasR PPMO#29 (FIG. 6C) or the AlgZ PPMO#27 (FIG. 6D), there is a decrease in the overall mass of the biofilm. Importantly, this occurred after just a single dose administration of PPMO. Animal studies, along with further dosing and kinetic studies, will be done to assess the impact on biofilm formation over time as well as studies on dosing in the setting of existing biofilms.

Example 2

PPMOs Targeted to Antibiotic Resistance Genes

Figure 7:
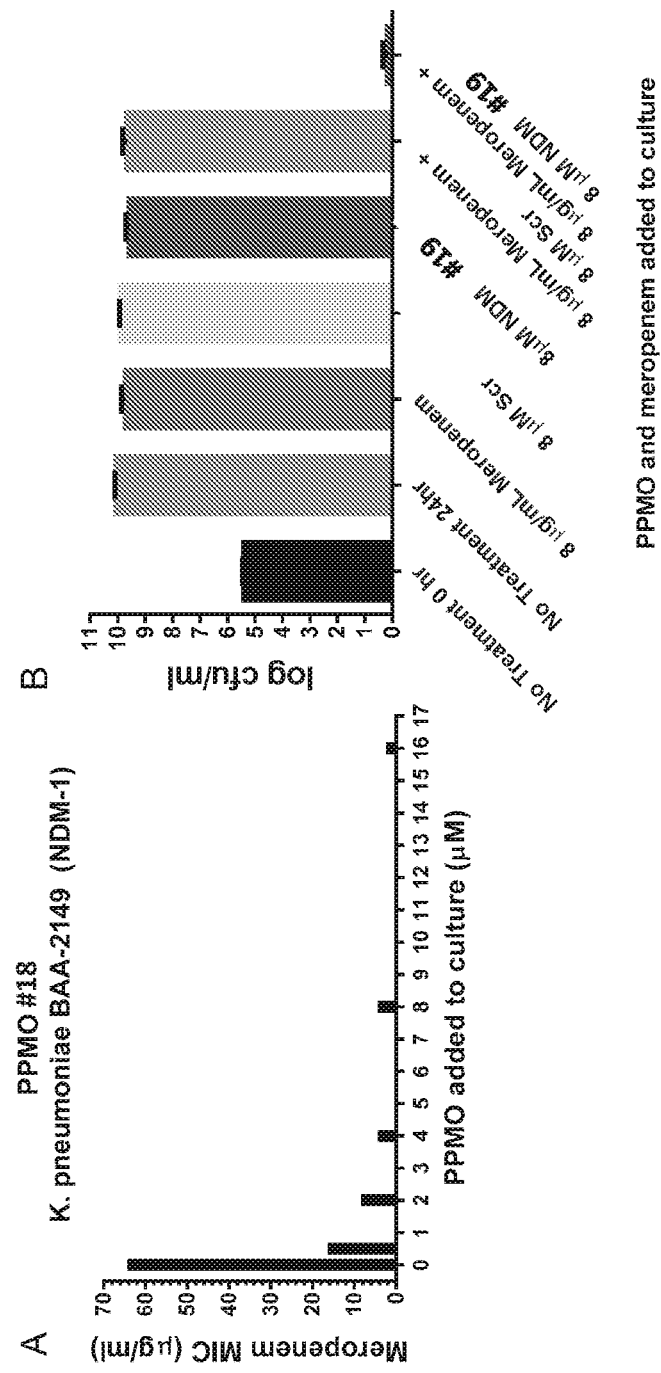
FIGS. 7A-7B show that PPMOs reduce the MIC of antibiotics in NDM-1 strains.

PPMOs were designed, synthesized and tested that target two of the most troublesome resistance genes, New Delhi metallo beta lactamase (NDM-1) and *Klebsiella pneumoniae* carbapenemase (KPC). It was found that 2 PPMOs were extremely effective in reducing the MIC of meropenem and imipenem in NDM-1 strains. The data show that 4 µM of NDM-1 PPMO#18 reduced the MIC of meropenem from 64 to 4 µg/ml (FIG. 7A). The CLSI breakpoint for meropenem in *K. pneumoniae* is 8 µg/ml. Another PPMO targeted to NDM-1 (PPMO#19) was similarly effective, and allowed meropenem to reduce viability by more than 4 orders of magnitude at 8 µg/ml (FIG. 7B). A similar reduction in MIC of meropenem was seen in other strains of *K. pneumoniae*. Importantly, these PPMOs are targeted to a region of the NDM-1 gene that is highly conserved across other variations of NDM, so they should be effective against strains that express the other known variations of NDM.

Figure 8A:
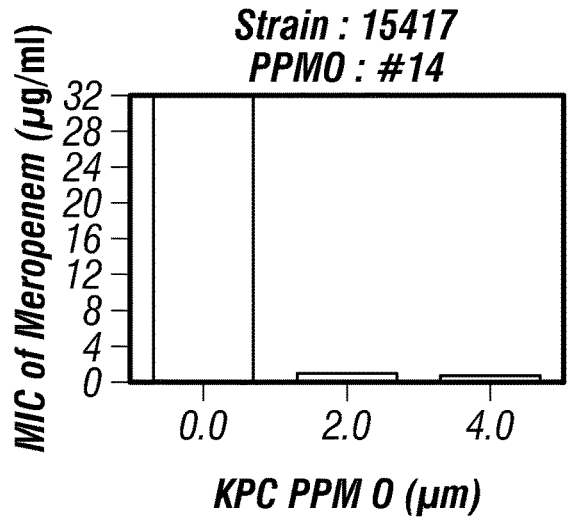
FIGS. 8A-8D show that PPMOs targeted to different regions of the KPC carbapenemase gene restored susceptibility of *K. pneumoniae* to meropenem. The MIC of meropenem was measured in various concentrations of KPC PPMO#14 (FIG. 8A) and KPC PPMO#13 (FIG. 8C). Viable cells were measured before (0 hr) or after growth for 24 hr with meropenem and/or KPC PPMO#14 (FIG. 8B) or KPC PPMO#13 (FIG. 8D).
Figure 8B:
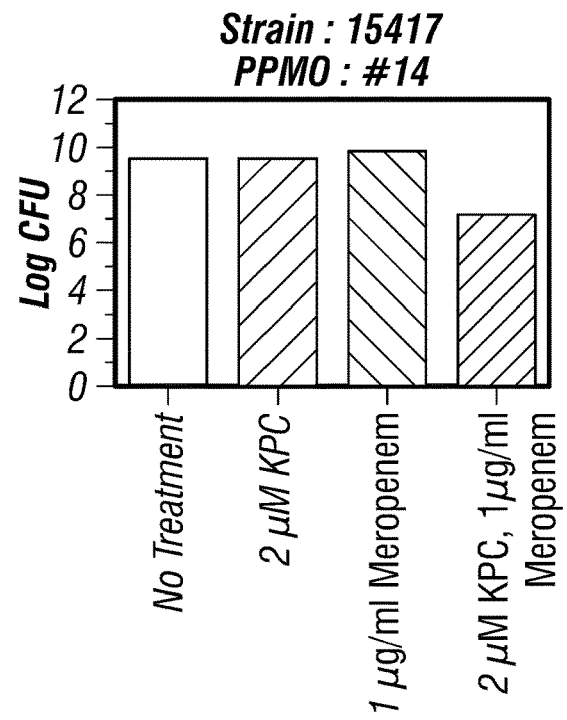
Figure 8C:
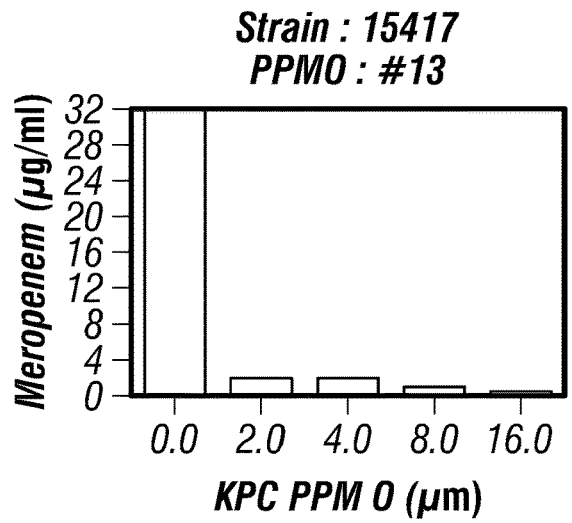
Figure 8D:
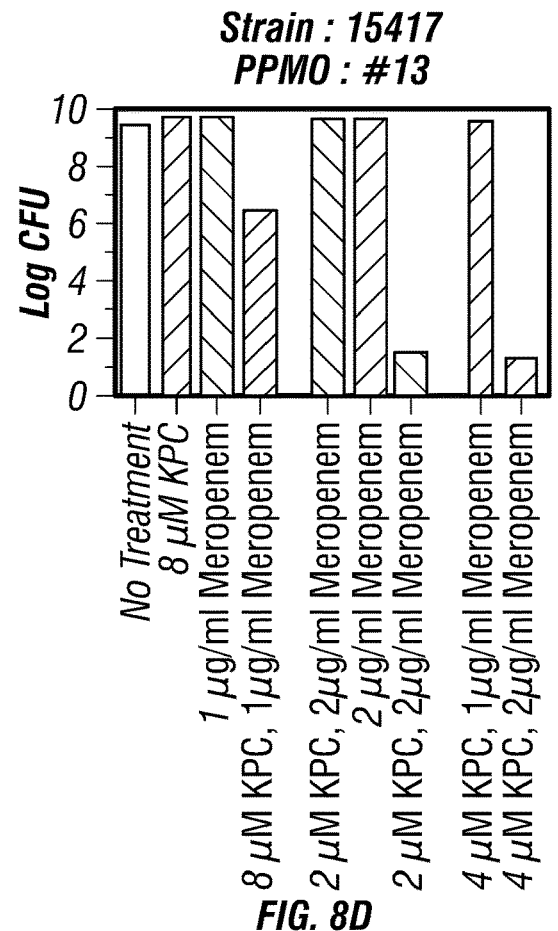

Two PPMOs targeted to different regions of the KPC carbapenemase gene restored susceptibility of *K. pneumoniae* to meropenem (FIGS. 8A-8D). The data show that 4 µM of KPC PPMO#14 reduced the MIC of meropenem from 32 to 0.5 µg/ml, and that 2 µM PPMO plus 1 µg/ml meropenem reduced growth by over 2 orders of magnitude (FIGS. 8A and 8B). KPC PPMO#13 had a similar potency (FIGS. 8C and 8D). Similar results were achieved with PPMO#35 as compared to PPMO#14 as shown in the table below.

| Potency of PPMO#14 vs PPMO#35 | | |
|---|---|---|
| | Relative Potency (µM$^{-1}$) with meropenem | |
| *K. pneumoniae* strain | PPMO#14 | PPMO#35 |
| 15410 | 2 | 4 |
| OR1 | 1 | 2 |
| OR13 | 2 | 0.5 |

Example 3

Preliminary Animal Tests

Figure 9A:
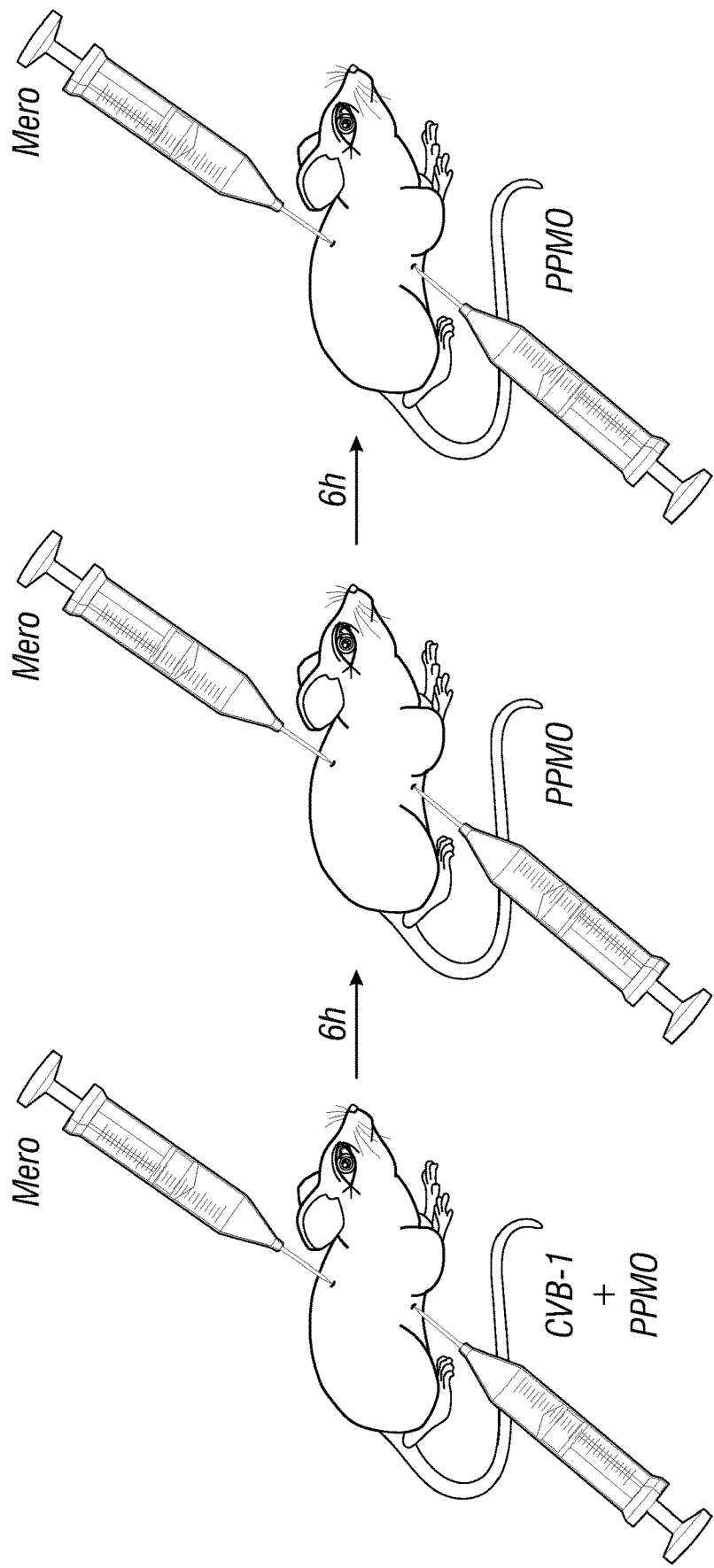
FIGS. 9a-9h show that the NDM-1 PPMO confers protection when administered concomitantly with meropenem in a systemic infection with NDM-1-positive *E. coli*. Mice were infected with *E. coli* CVB-1 and treated with either 1 mg of meropenem (n=8) (given subcutaneously), 100 pg (5 mg kg$^{-1}$) of PPMO (n=7) (given intraperitoneally), both treatments (n=12), a scrambled PPMO (Ser) with meropenem (n=11), or PBS (n=7).
Figure 9B:
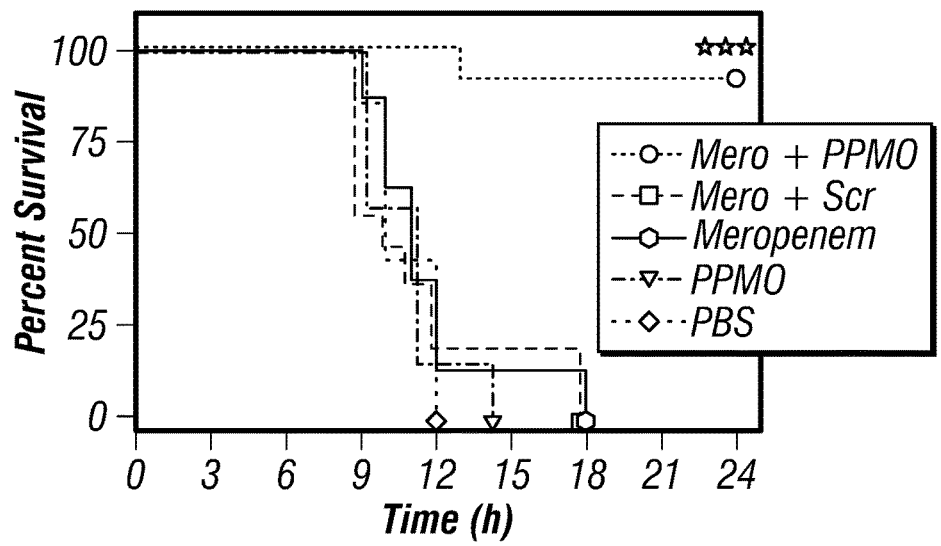
Figure 9C:
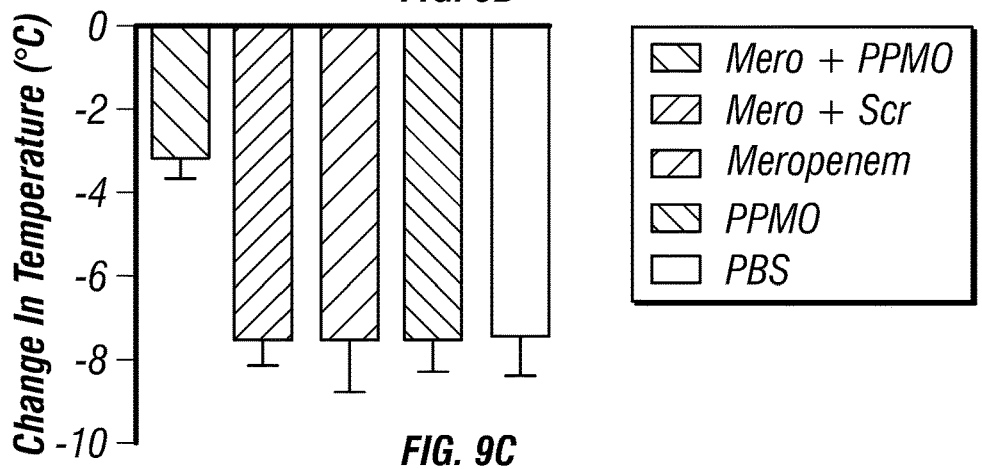
Figure 9D:
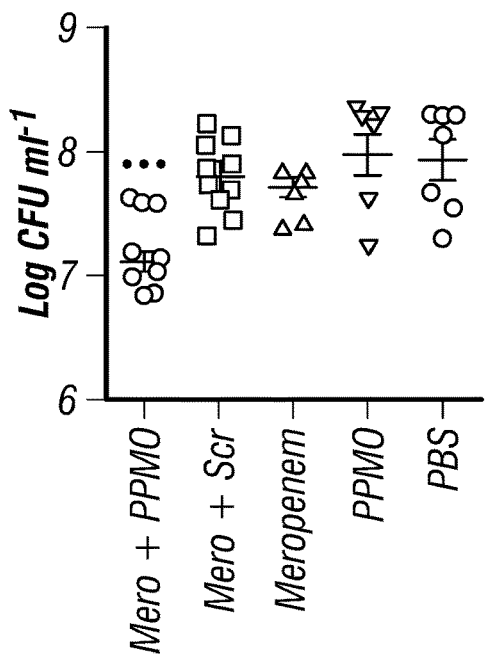

The NDM-1 PPMO#18 was tested in a mouse model of sepsis, using a strain of *E. coli* that expresses NDM-1. Mice were infected and treated by intraperitoneal injection of a freshly-prepared mixture of *E. coli* CVB-1 and NDM-1 PPMO (100 µg). Meropenem was then immediately administered subcutaneously. Treatments were administered every 6 h post-infection for the first 24 h, and the mice were monitored for survival for 7 days (FIG. 9a). The results show 92% survival of the mice treated concomitantly with PPMO and meropenem. This is a significant increase compared to mice treated with either PPMO or meropenem separately, or with co-administration of a scrambled PPMO (Ser) and meropenem, all of which died by 18 h (FIG. 9b). The mice treated with both NDM-1 PPMO and meropenem were healthier, as assessed by body temperature (FIG. 9c), and had significantly less bacterial burden in the bloodstream (FIG. 9d) and spleen.

Figure 9E:
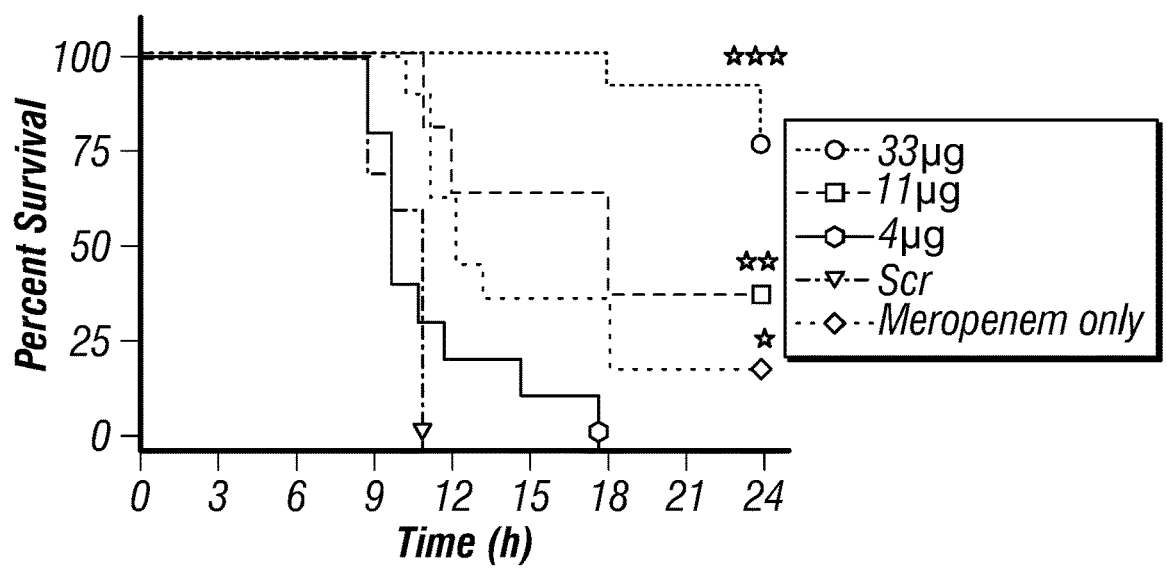
Figure 9F:
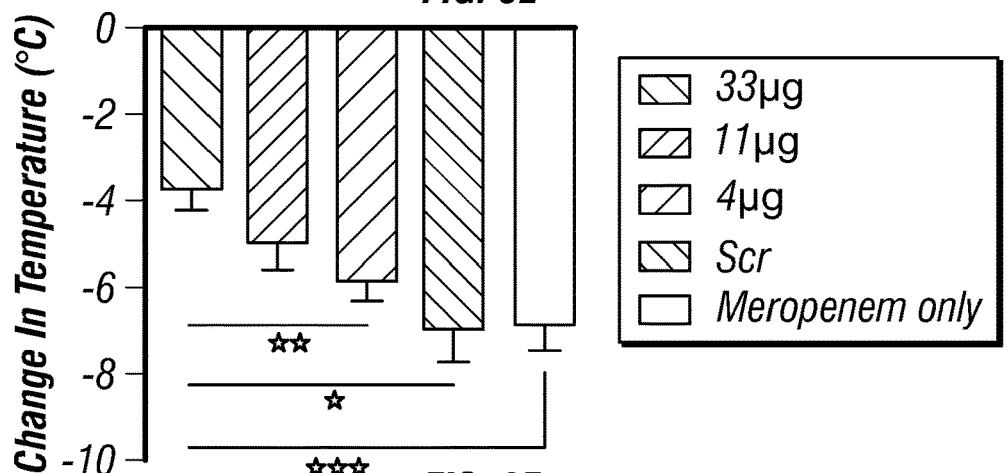
Figure 9G:
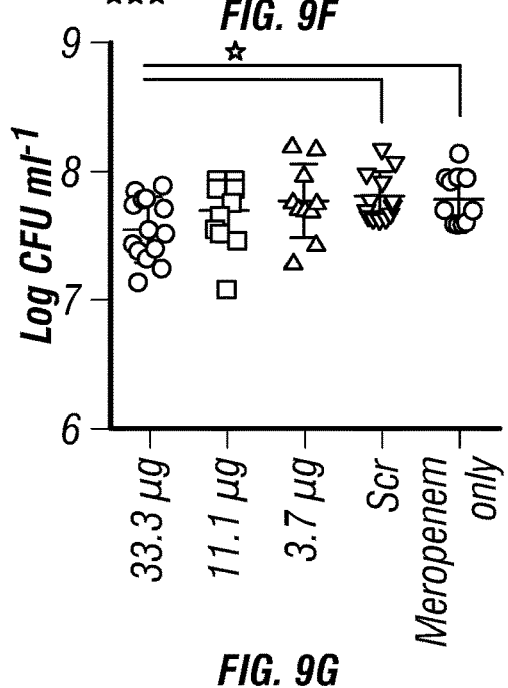

The dose of PPMO was reduced to 33, 11, or 4 µg. The morbidity and mortality of the mice was inversely proportional to the dose of PPMO (FIG. 9e-9g). Co-treatment with 33 µg of PPMO and 1 mg meropenem was sufficient to protect over 75% of the infected mice (FIG. 9e and FIG. 9f) and significantly decreased the viable bacteria in the blood (FIG. 9g). Lesser amounts of PPMO were less effective but still demonstrated significant improvement in survival as compared to the two negative controls. These data indicate that the PPMO increased bacterial susceptibility to antibiotic killing in vivo in a dose-dependent fashion.

Figure 9H:
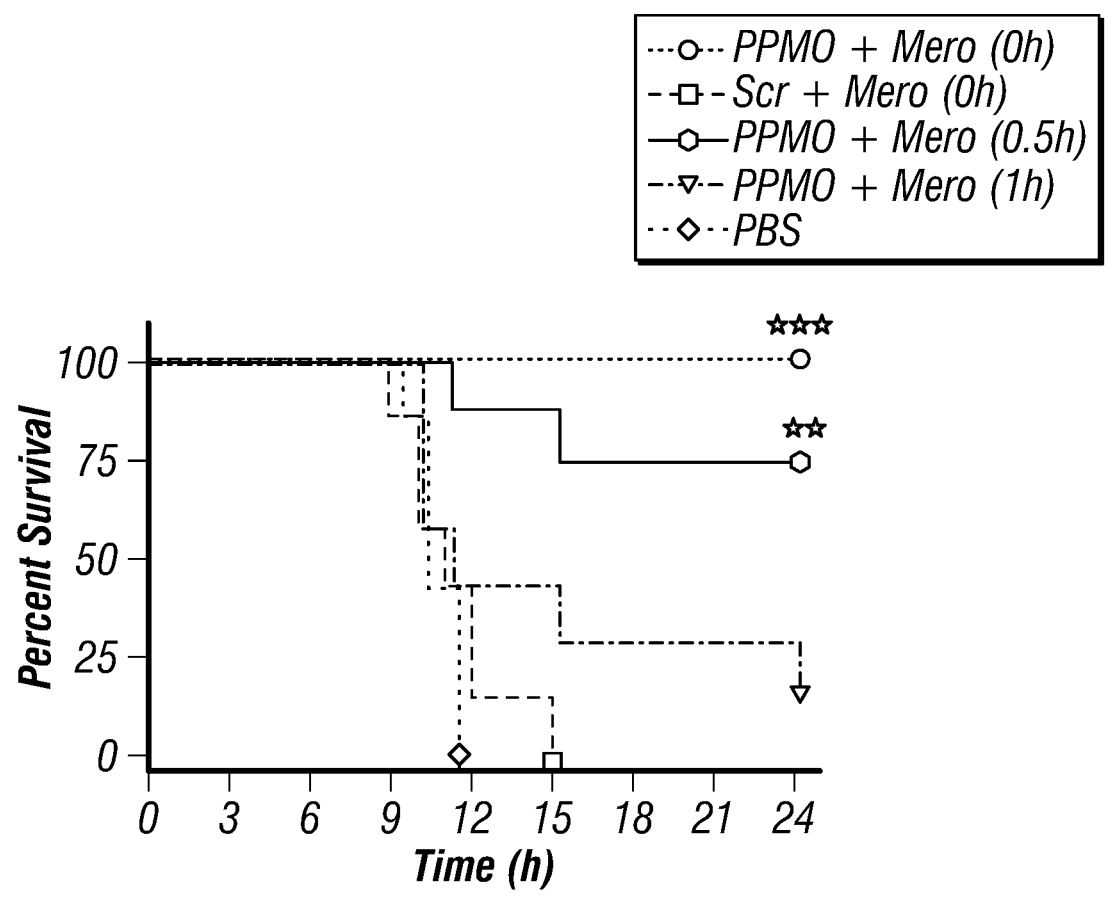

To determine whether PPMO could be used effectively as a delayed therapy, mice were infected as described above and then treated with both meropenem (subcutaneously) and 250 µg PPMO (intraperitoneally) at 0.5 h or 1 h after infection and every 6 h thereafter for 24 h. When treatment was delayed 0.5 h post-infection, the administration of meropenem and PPMO was able to rescue 75% of the mice (FIG. 9h), a significant effect compared to the treatments given the control groups. Treatment delayed 1 h was not statistically significant, but there was a trend toward an increase in mean time to death (14.86 h±2.454) as compared to the Ser PPMO with meropenem treated group (11.29 h±0.7469). These in vivo data demonstrate that NDM-1 PPMO can be used therapeutically and have a protective effect when administered concurrently with meropenem.

Example 4

PPMOs Targeted to Antibiotic Resistance Genes AcrA, AcrB, AcrR and TolC Reduce the MIC of Piperacillin-Tazobactam (PT)

Figure 10A:
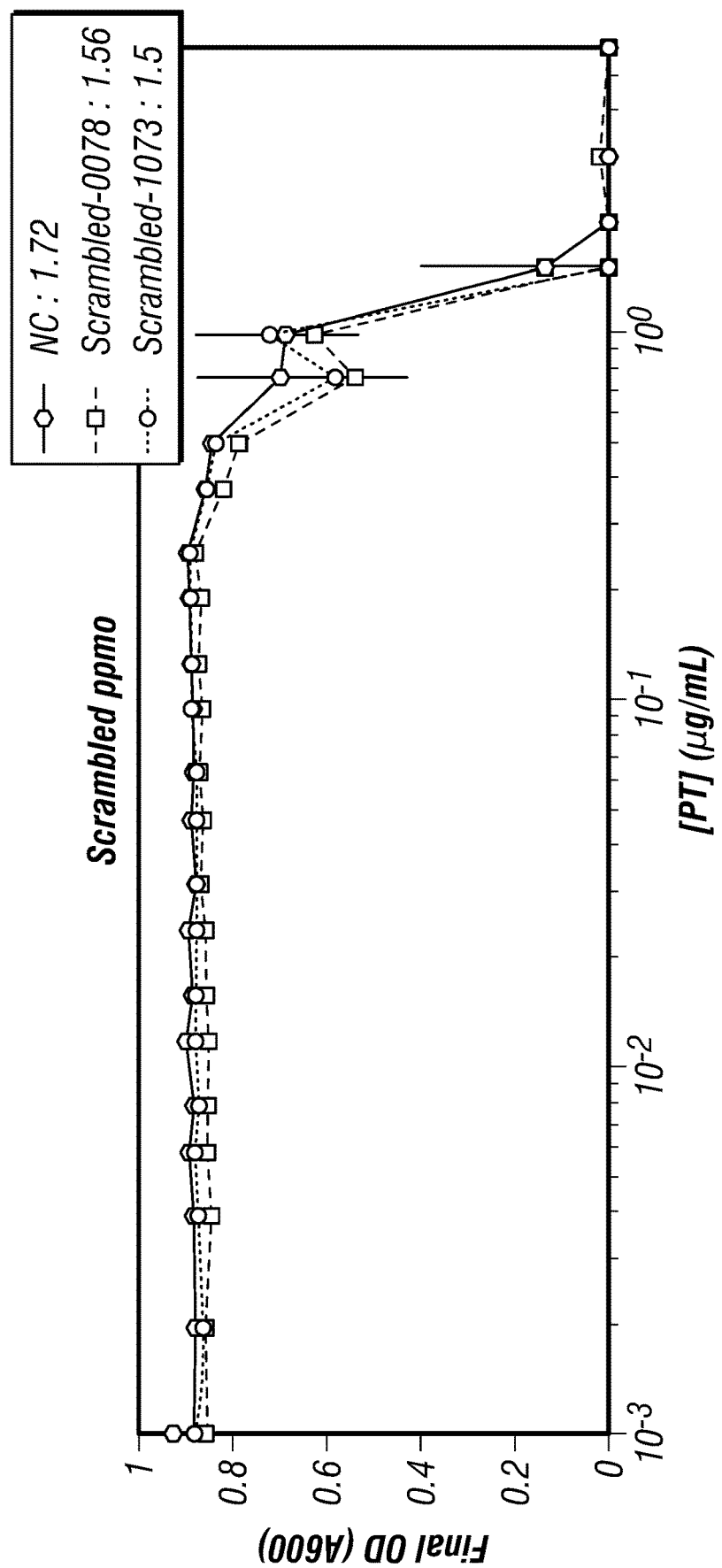
FIGS. 10A-10E show that PPMOs targeted to multi-drop efflux pump genes AcrA, AcrB, AcrR and TolC were effective at reducing viability of an *E. coli* strain when co-incubated with piperacillin-tazobactam (PT). *E. coli* were treated with scrambled PPMOs (FIG. 10A), AcrA PPMOs #3, #4 and #5 (FIG. 10B), AcrB PPMOs #6 and #8 (FIG. 10C), AcrR PPMO#9 (FIG. 10D), and TolC PPMO#11 (FIG. 10E). The addition of the active PPMOs reduced the MIC of PT by 2-8 fold depending on the PPMO tested.
Figure 10B:
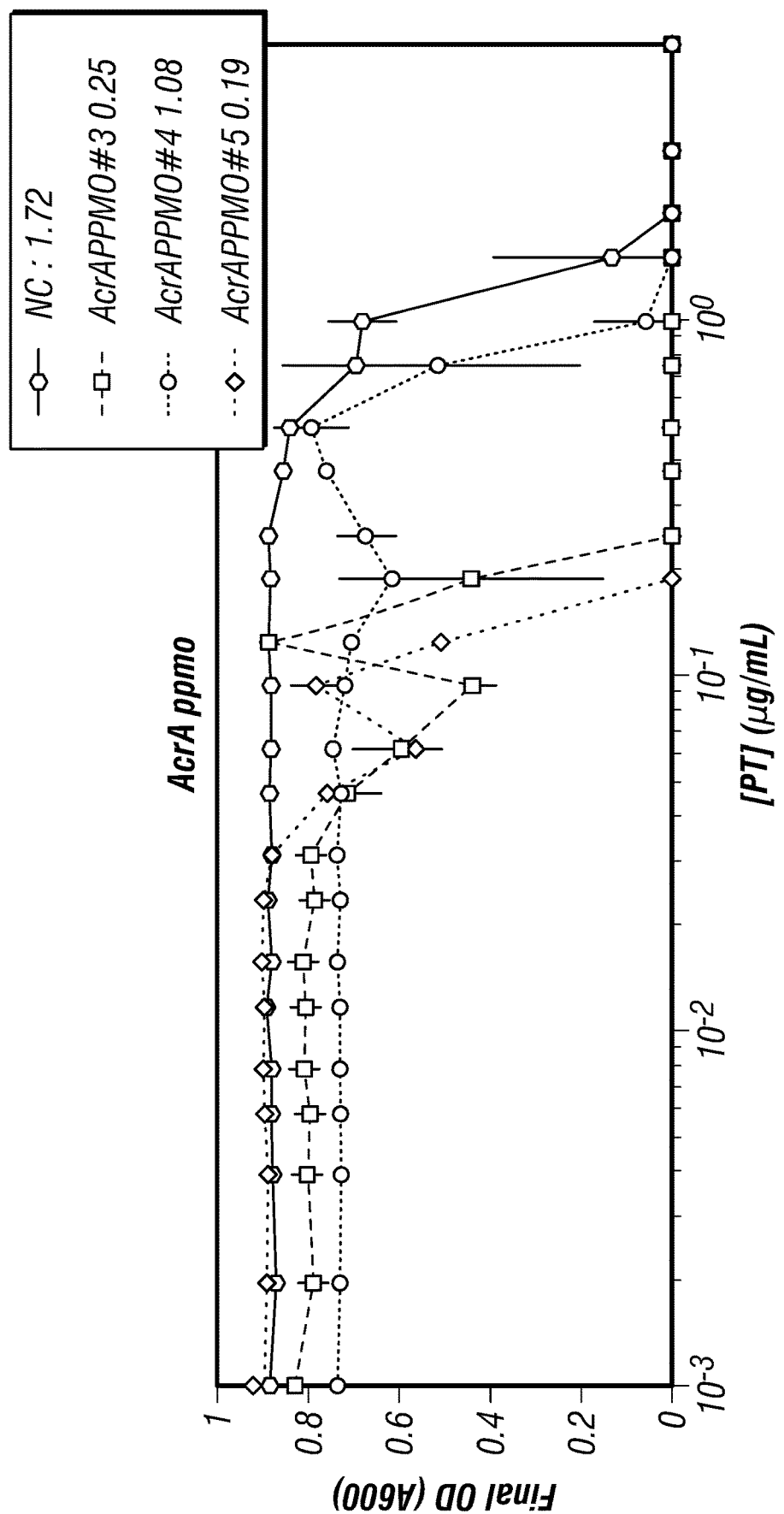
Figure 10C:
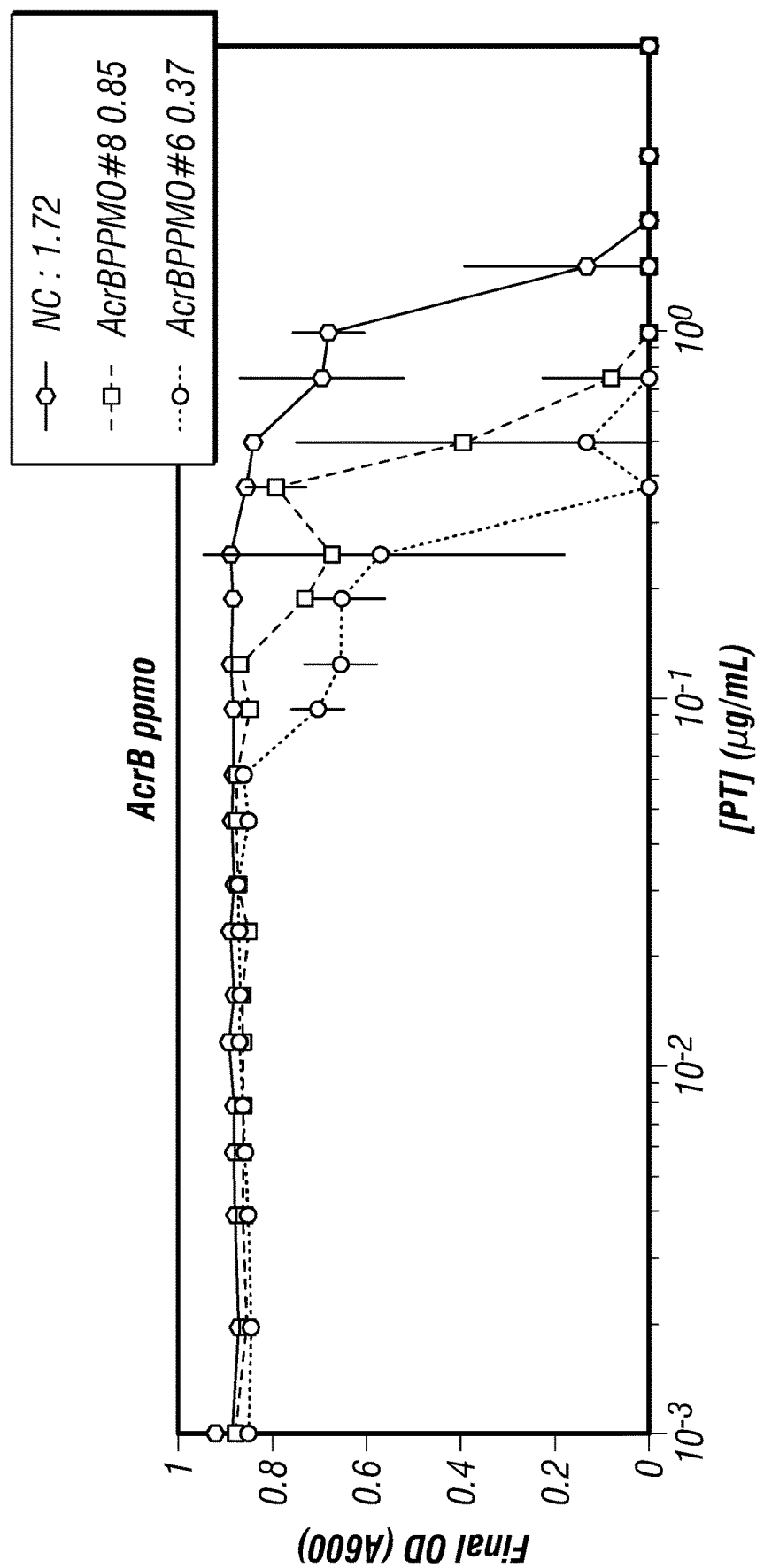
Figure 10D:
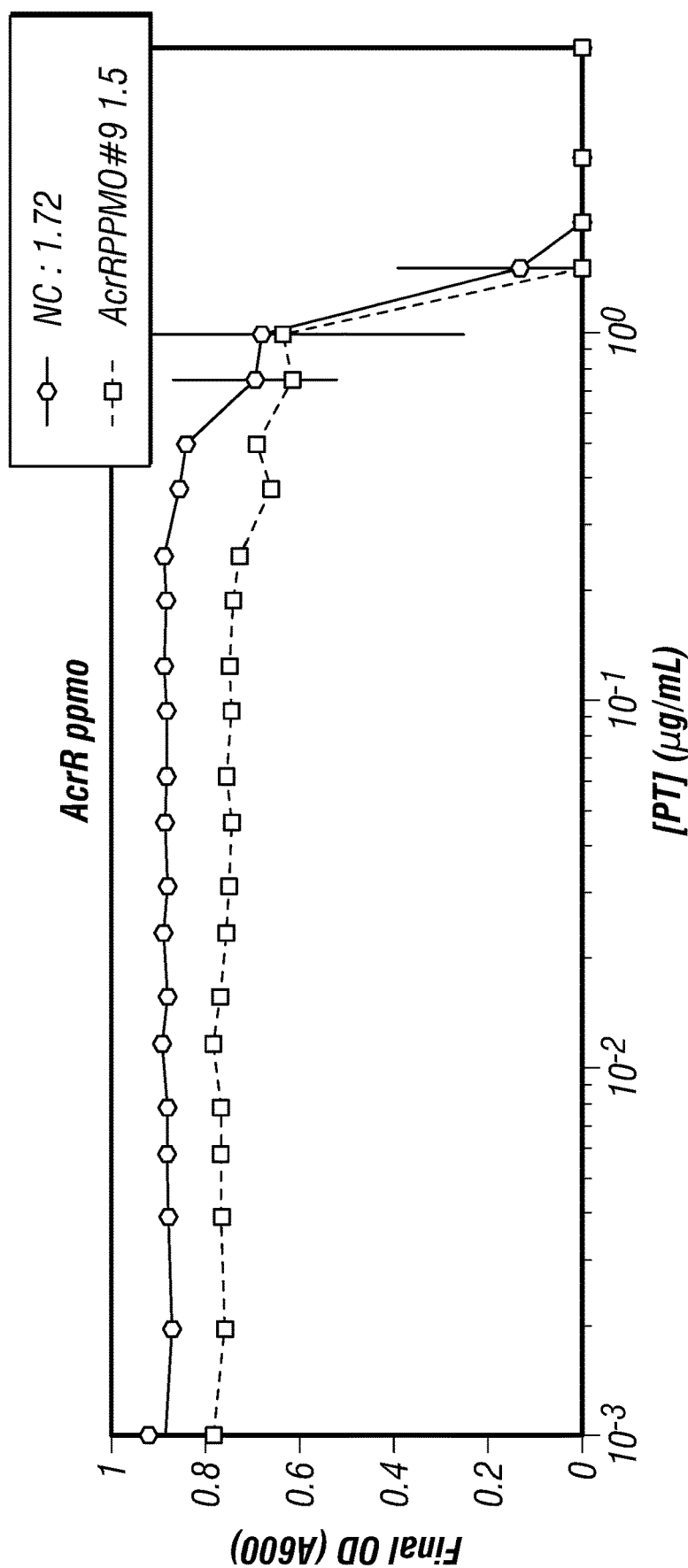
Figure 10E:
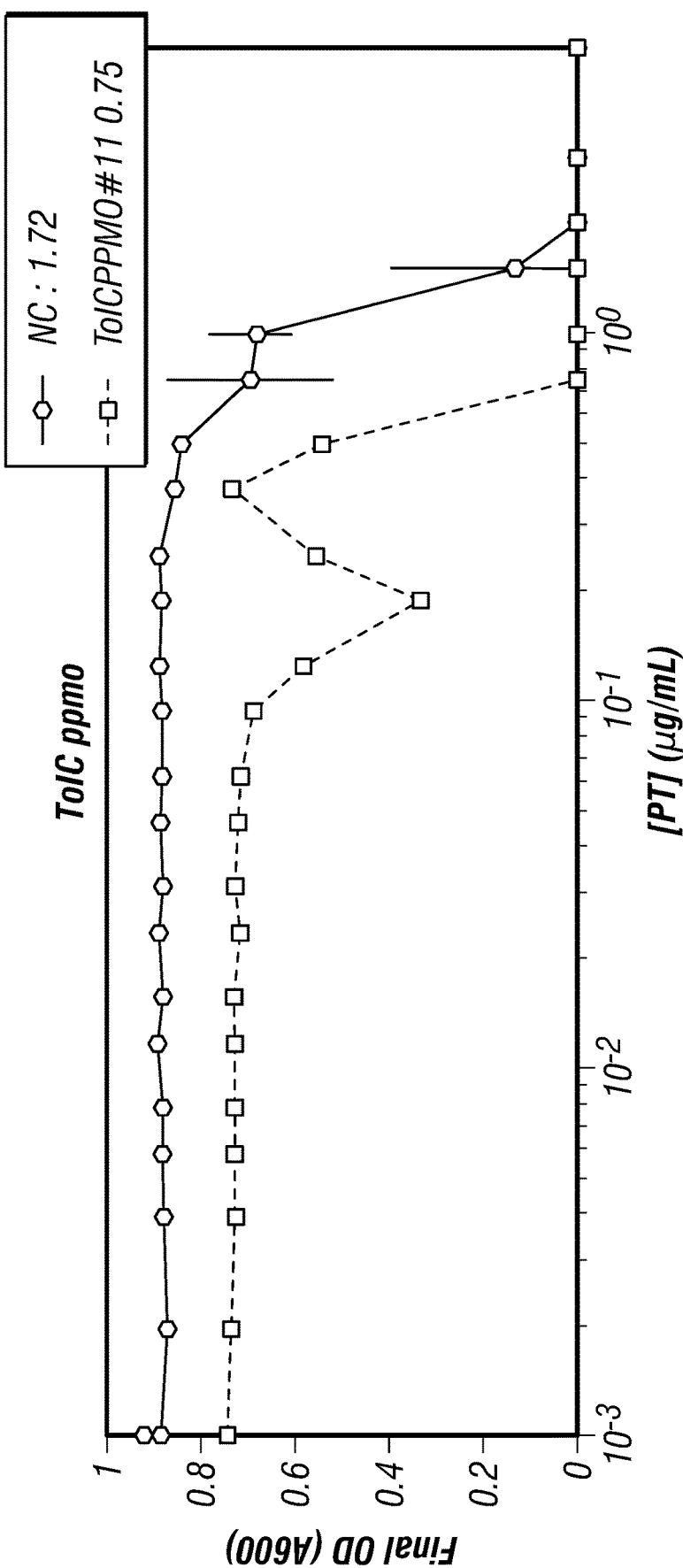

PPMOs were designed, synthesized and tested that target the AcrA, AcrB, AcrR and TolC multi-drug efflux pump genes of *E. coli*. *E. coli* were treated with PPMOs co-incubated with piperacillin-tazobactam (PT) (FIGS. 10A-10E) and MIC values were determined for PT with either active or scrambled PPMOs. Scrambled PPMOs had no effect on the MIC of PT (FIG. 10A), while addition of active PPMOs targeted against AcrA (PPMOs #3, #4, #5, FIG. 10B), AcrB (PPMOs #6 and #8, FIG. 10C), AcrR (PPMO#9, FIG. 10D) and TolC (PPMO#11, FIG. 10E) reduced the MIC of PT by 2-8 fold depending on the PPMO tested.

Example 5 acrA, acrB, and tolC: Antibiotic Hypersensitivity

The AcrAB-TolC efflux pump complex is among the best-characterized efflux pumps in *E. coli* and is composed of AcrB, the inner membrane antiporter, AcrA, the periplasmic adaptor protein, and TolC, the outer membrane channel. Deleting or silencing acrB or the two other genes (acrA and tolC) that form the AcrA-AcrB-TolC efflux pump complex (FIG. 11A) in *E. coli* may decrease the intrinsic antibiotic resistance of *E. coli*.

Figure 11:
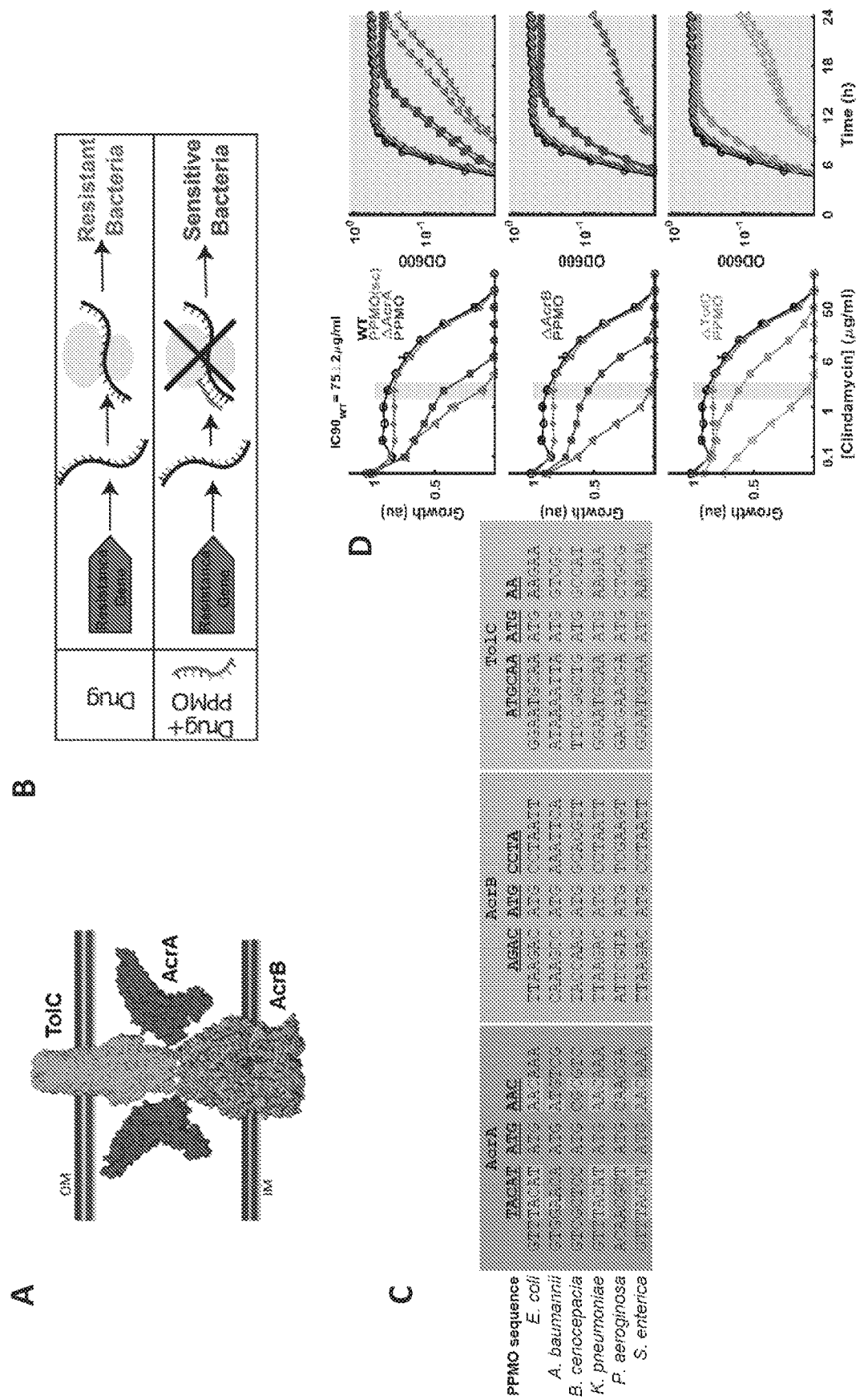
FIG. 11A: Representation of the AcrAB-TolC efflux system.
FIG. 11B: PPMOs are antisense molecules that may bind to mRNA molecules and block translation of resistance genes.
FIG. 11C: Three separate PPMOs were designed to target the acrA (PPMO#3, left), acrB (PPMO#8, middle), and tolC (PPMO#10, right) mRNAs. These PPMOs target regions that span the start codons of the transcribed mRNA. Alignment of the acrA, acrB, and tolC genes of different bacterial species describe sequence similarities.
FIG. 11D: (Left) Dose response curves as a function of clindamycin concentration for the wild type *E. coli* without PPMO (solid circle), with 10 μM scrambled control PPMO (open circle), with 10 μM acrA-PPMO (top panel, square), *E. coli* with acrA deletion (top panel, triangle), with 10 μM acrB-PPMO (middle panel, squares), *E. coli* with acrB deletion (middle panel, triangles), with 10 μM tolC-PPMO (bottom panel, squares), and *E. coli* with tolC deletion (bottom panel, triangles). (Right) Sample growth curves at the conditions shown within the grey shaded areas on the dose response curves on the left.
Figure 12:
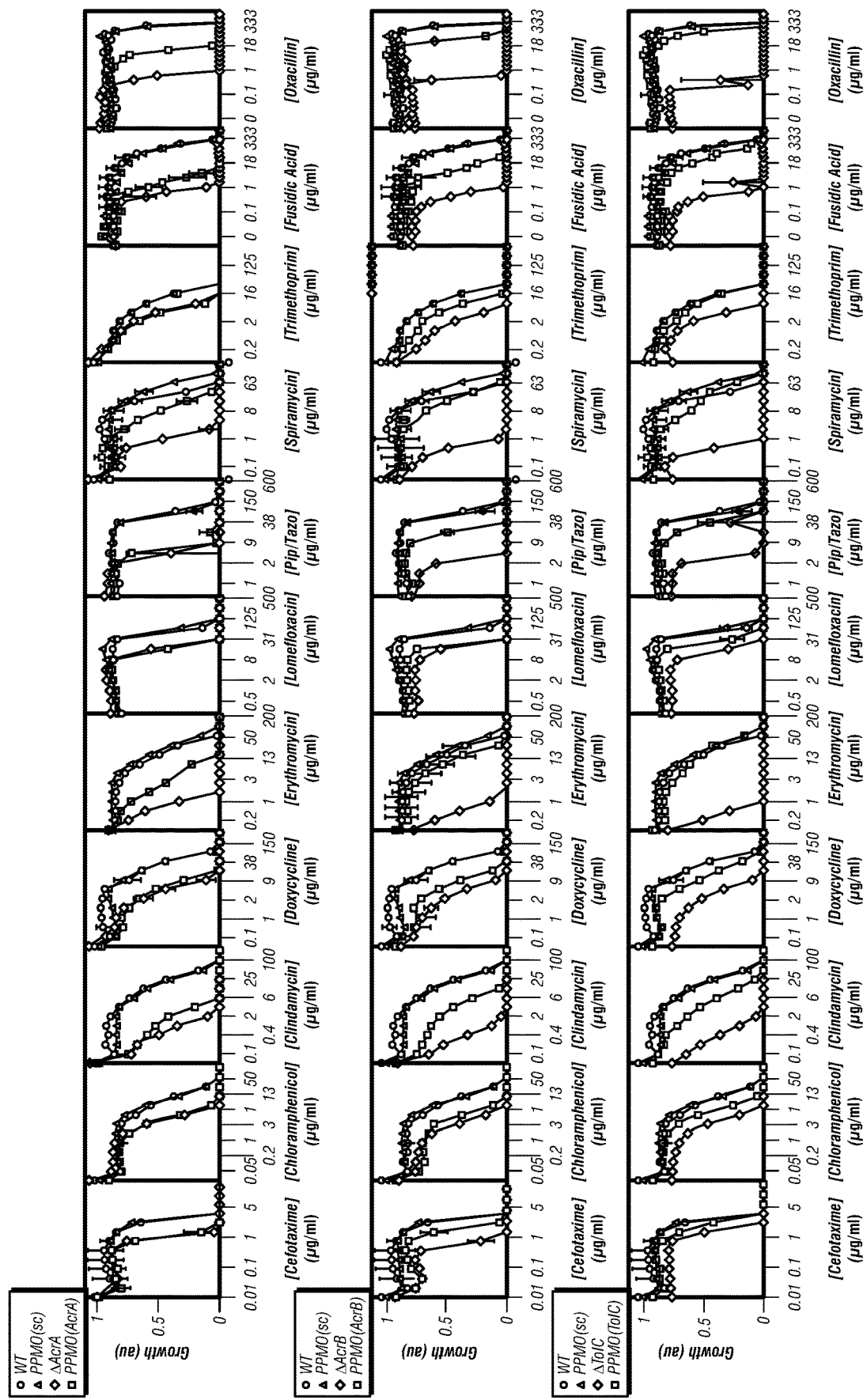
FIG. 12 shows dose response curves as a function of antibiotic concentration for a number of antibiotics. Top panel: the wild type *E. coli* without acrA-PPMO (open circles), with 10 μM scrambled control PPMO (solid circles), with 10 μM acrA-PPMO (squares), *E. coli* with acrA deletion (triangles). Middle panel: the wild type *E. coli* without acrB-PPMO (open circles), with 10 μM scrambled control PPMO (solid circles), with 10 μM acrB-PPMO (squares), *E. coli* with acrB deletion (triangles). Bottom panel: the wild type *E. coli* without tolC-PPMO (open circles), with 10 μM scrambled control PPMO (solid circles), with 10 μM tolC-PPMO (squares), and *E. coli* with tolC deletion triangles).

Three PPMOs were designed to target the acrA, acrB and tolC mRNAs respectively (FIG. 11B, FIG. 11C). These PPMOs are 11-base oligomers that are conjugated to a membrane penetrating peptide (acrA PPMO#3, acrB PPMO#8 and tolC PPMO#10). The efficacy of these PPMOs was tested by measuring *E. coli* minimum inhibitory concentration (MIC) for several antibiotics in the presence of PPMOs (FIG. 11D and FIG. 12). As depicted in FIG. 12 (solid squares), acrA PPMO, acrB PPMO and tolC PPMO each induced antibiotic sensitivity to *E. coli* cells. FIG. 11D demonstrates the effect of 10 µM acrA PPMO when used with clindamycin; clindamycin resistance decreased by ~16-fold (FIG. 11D, solid squares). The deletion of the acrA gene reduced clindamycin resistance by ~32-fold (FIG. 11D, triangles).

Figure 13:
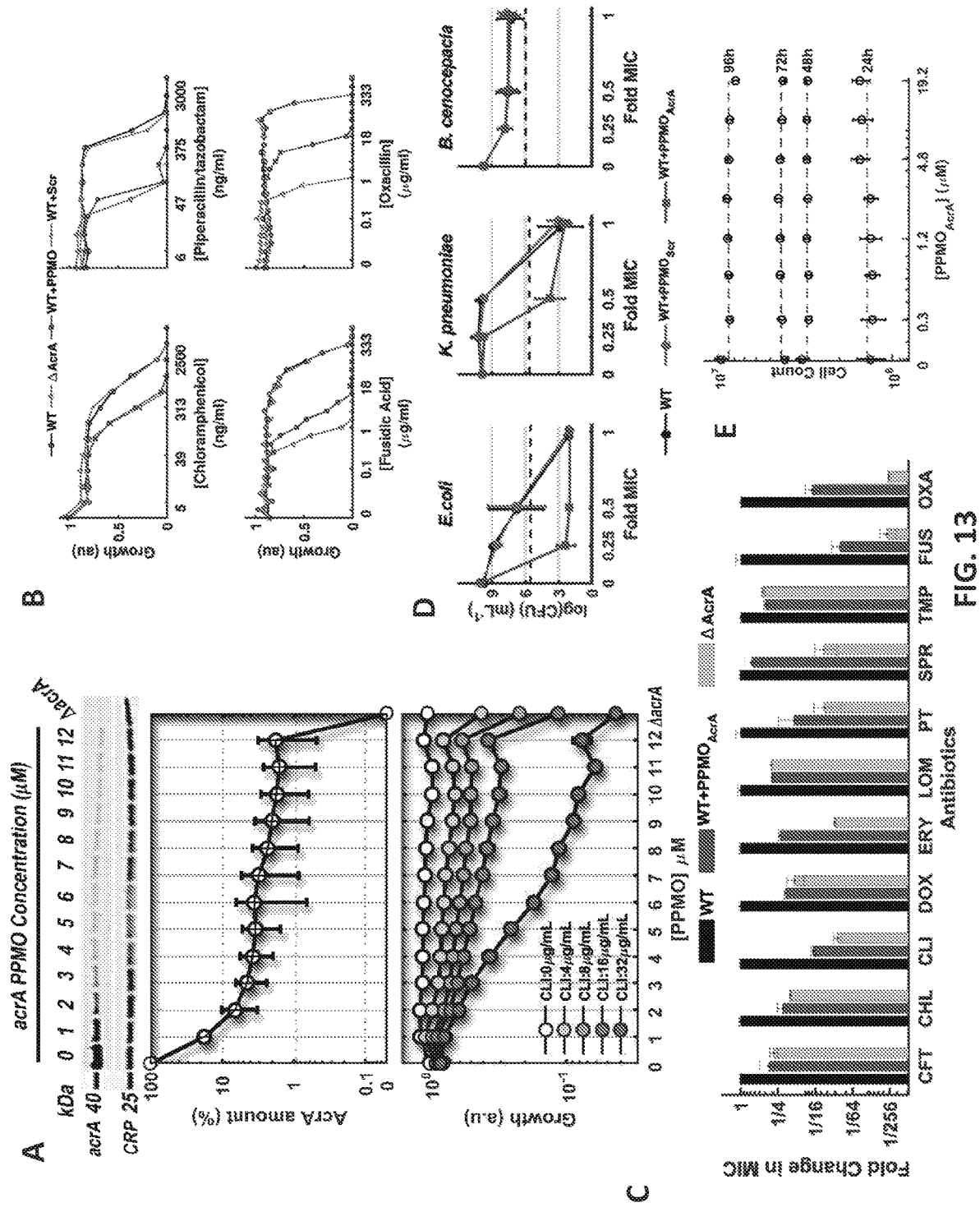
FIGS. 13A-13E depicts AcrA translation in the presence of AcrA-PPMO and sensitivity against numerous antibiotics.

Example 6 acrA-PPMO Blocks AcrA Translation in a Dose Dependent Manner and Reduces Resistance to Several Antibiotics acrA silencing was quantified by measuring the AcrA expression in *E. coli* using increasing concentrations of acrA PPMO (FIG. 13A). The expression of AcrA in *E. coli* decreased nearly thirty-fold at acrA PPMO concentrations greater than 2 µM. This effect was verified by measuring growth rates of *E. coli* cells at different sub-lethal clindamycin concentrations using increasing concentrations of acrA PPMO. Growth of *E. coli* cells in constant clindamycin doses gradually slowed down as acrA PPMO concentration was increased, indicating that clindamycin sensitivity was correlated with the AcrA expression in bacterial cells (FIG. 13A, bottom panel).

Targeting the acrA gene with the acrA PPMO decreased resistance of *E. coli* against eleven antibiotics (FIG. 13B, FIG. 13C). The sensitization effect varied between a 2- and 40-fold reduction (FIG. 13C). Importantly, the sensitization effect of acrA PPMO was specific to *E. coli*. The efficacy of acrA PPMO against *Burkholderia cenocepacia* (K56-2), *E. coli* (BW25113), and *Klebsiella pneumoniae* (F45153) was tested by incubating bacterial cells in increasing concentrations of piperacillin-tazobactam using 10 µM acrA PPMO and counting colony forming units (CPUs) after 18 hours of antibiotic exposure. At sub-lethal doses (MIC/4) of piperacillin-tazobactam, the number of CPUs decreased by ~$10^6$-fold when acrA PPMO was present (FIG. 13D, left). A similar sensitization effect was seen with acrA PPMO against *Klebsiella pneumoniae*, which shares the exact same acrA sequence with *E. coli* (FIG. 13D, middle). Without wishing to be bound by any particular theory, the acrA PPMO had no activity against *Burkholderia cenocepacia* may be because of sequence dissimilarity (FIG. 11C and FIG. 13D). Finally, the toxicity of acrA PPMO against mammalian cells using the HBEC3KT viability assay was tested and no toxicity was found (FIG. 13E). These observations provide clear evidence that acrA PPMO is a promising agent that works as an efficient antibiotic-enhancer molecule by blocking the formation of AcrAB-TolC efflux pump in a species-specific way.

Example 7

Using acrA-PPMO Together with Antibiotic Pairs is a Promising Strategy, Rescuing Even the Activity of Antagonistic Antibiotics The acrA PPMO was tested together with antibiotic pairs in order to amplify the antimicrobial activity of antibiotic pairs. Using antibiotics in combination is generally considered a promising strategy for using antibiotic compounds more effectively. Antibiotic therapies that combine synergistic drug pairs are justifiably favored in clinical practice. However, this requirement limits the number of drug combinations that can be used in clinical practice, as higher doses of drugs are required for clinical efficacy. In addition, when used together, several synergistic antibiotic pairs are expected to promote evolution of multidrug resistance since they have overlapping resistance mechanisms. Therefore, strategies that could rescue the use of antagonistic drug combinations will be a great advancement in medicine. The present disclosure demonstrates that sensitizing bacteria against antibiotics by silencing resistance genes can compensate for the antagonized activity of drug combinations and therefore allow the use of antagonistic pairs in combination therapies.

Figure 14:
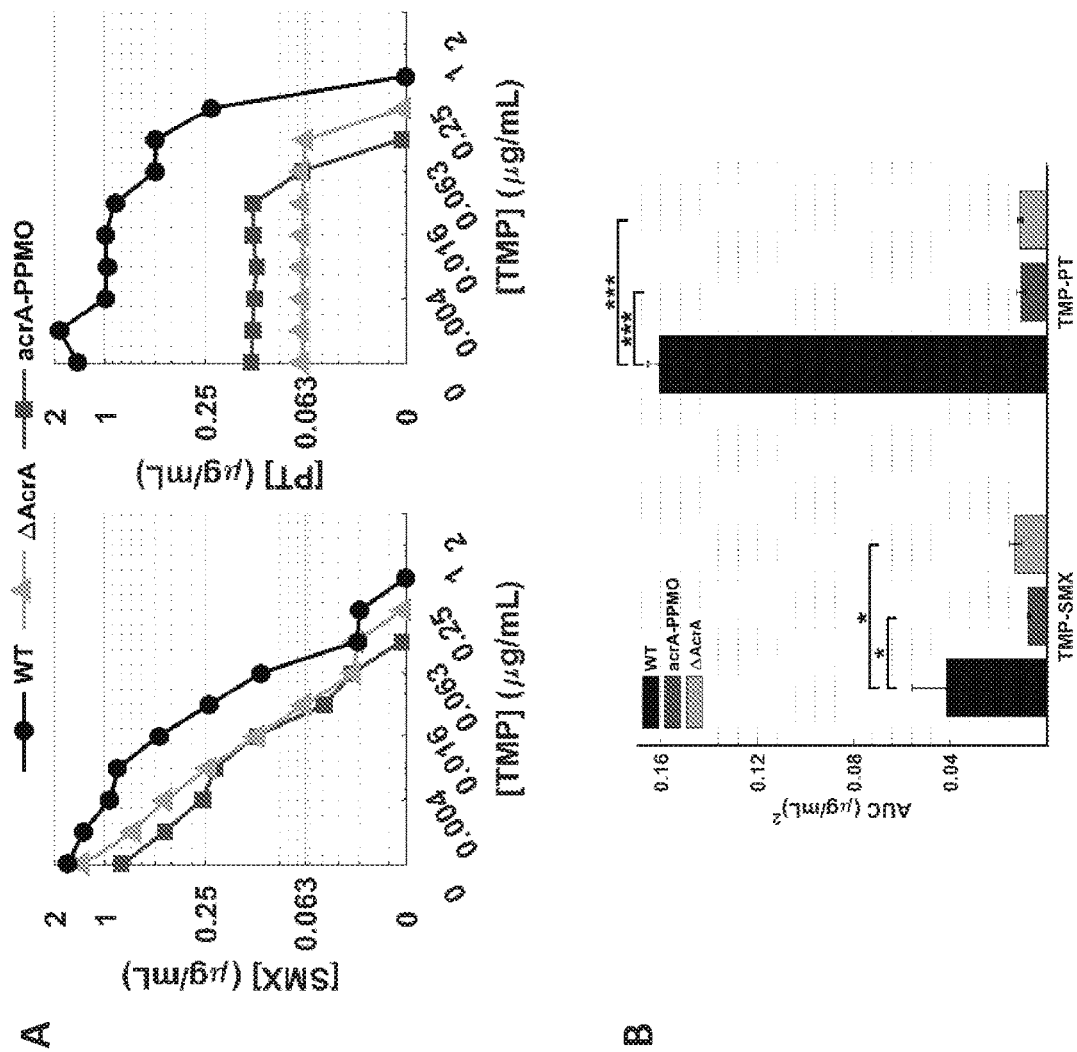
FIGS. 14A-14B shows efficacy of antibiotic combinations in the presence of acrA-PPMO including antagonistic antibiotic pairs.

Pairwise interactions were quantified between trimethoprim, sulfamethoxazole, and piperacillin-tazobactam in the presence and absence of acrA PPMO (FIG. 14A). Trimethoprim is an antifolate drug that blocks the activity of the dihydrofolate reductase enzyme. Trimethoprim is often used together with sulfamethoxazole (another antifolate) due to their synergistic interaction. Conversely, using trimethoprim with piperacillin-tazobactam is problematic since these two drugs antagonize each other's activities. Two-dimensional gradients of trimethoprim and sulfamethoxazole (FIG. 14A—left), and trimethoprim and piperacillin-tazobactam (FIG. 14A—right), were created and MIC values were measured for the wild type $E.$ $coli$ strain in the presence (FIG. 14A, triangles) and absence (FIG. 14A, circles) of acrA PPMO; the MIC values were also measured for the $E.$ $coli$ strain with acrA deletion (FIG. 14A, squares). The efficacies of drug combinations were compared by calculating the areas under the MIC curves (AUC, FIG. 14B). acrA PPMO increased the efficacy of both drug combinations by approximately five-fold and fifteen-fold for trimethoprim-sulfamethoxazole (FIG. 14B—left), and trimethoprim-piperacillin-tazobactam, respectively (FIG. 14B—right). This observation clearly indicates that even though trimethoprim and piperacillin-tazobactam have antagonistic interactions, hypersensitizing $E.$ $coli$ by silencing the acrA gene significantly (~15-fold, $p<0.001$) increases the efficacy of the trimethoprim-piperacillin-tazobactam combination. This advancement makes the trimethoprim-piperacillin-tazobactam combination a promising candidate for treating infections since trimethoprim and piperacillin-tazobactam have independent resistance mechanisms that make the emergence of cross-resistance unlikely.

The invention claimed is:

1. An antisense morpholino oligomer, composed of morpholino subunits and phosphorus-containing intersubunit linkages joining a morpholino nitrogen of one subunit to a 5'-exocyclic carbon of an adjacent subunit, and having (a) about 10-40 nucleotide bases, and (b) a targeting sequence selected from a) SEQ ID NO: 11 (ATG TAA ACC TC);
    b) SEQ ID NO: 12 (GTT CAT ATG TA);
    c) SEQ ID NO: 13 (AAC CCT CTG TT);
    d) SEQ ID NO: 14 (TGT TCA TAT GT);

wherein thymine, bases (T) may be uracil bases (U), and where the oligomer is conjugated to a cell-penetrating peptide (CPP).

2. The antisense morpholino oligomer of claim 1, wherein the antisense morpholino oligomer is of formula (1):

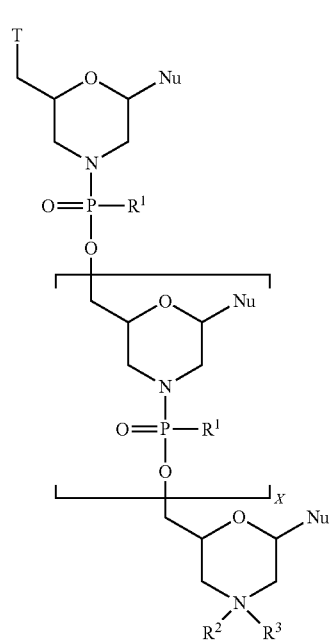

(I)

or a pharmaceutically acceptable salt thereof, where each Nu is a nucleobase which taken together forms a targeting sequence;

X is an integer from 9 to 38;

T is selected from OH and a moiety of the formula:

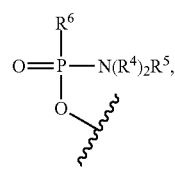

where each $R^4$ is independently $C_1$-$C_6$ alkyl, and $R^5$ is selected from an electron pair and H, and $R^6$ is selected from OH, —$N(R^7)CH_2C(O)NH_2$, and a moiety of the formula:

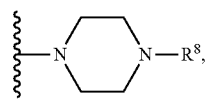

where:

$R^7$ is selected from H and $C_1$-$C_6$ alkyl, and $R^8$ is selected from G, —C(O)—$R^9$OH, acyl, trityl, and 4-methoxytrityl, where:

$R^9$ is of the formula —(O-alkyl)$_y$- wherein y is an integer from 3 to 10 and each of the y alkyl groups is independently selected from $C_2$-$C_6$ alkyl;

each instance of $R^1$ is —$N(R^{10})_2R^{11}$ wherein each $R^{10}$ is independently $C_1$-$C_6$ alkyl, and $R^{11}$ is selected from an electron pair and H;

$R^2$ is selected from H, G, acyl, trityl, 4-methoxytrityl, benzoyl, steamy', and a moiety of the formula:

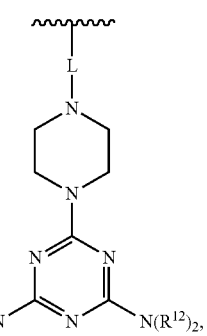

where L is selected from —C(O)(CH$_2$)$_6$C(O)— and —C(O)(CH$_2$)$_2$S$_2$(CH$_2$)$_2$C(O)—, and each $R^{12}$ is of the formula —(CH$_2$)$_2$OC(O) N(R$^{14}$)$_2$ wherein each $R^{14}$ is of the formula —(CH$_2$)$_6$N HC(=NH)NH$_2$; and $R^3$ is selected from an electron pair, H, and $C_1$-$C_6$ alkyl, wherein G is a cell penetrating peptide ("CPP") and linker moiety selected from —C(O)(CH$_2$)5N H—CPP, —C(O)(CH$_2$)$_2$N H—CPP, —C(O)(CH$_2$)$_2$NHC(O)(CH$_2$)5NH—CPP, and —C(O)CH$_2$NH—CPP, or G is of the formula:

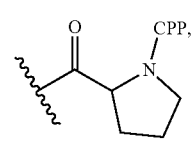

wherein the CPP is attached to the linker moiety by an amide bond at the CPP carboxy terminus, with the proviso that only one instance of G is present.

3. The antisense morpholino oligomer of claim 2, wherein T is selected from:

117

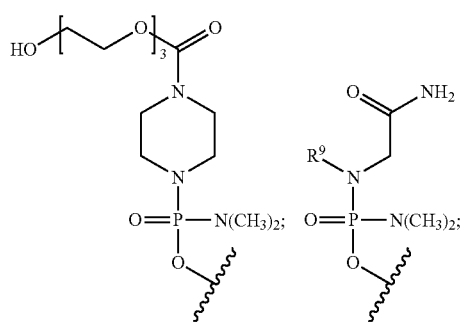

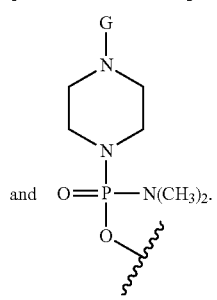

4. The antisense morpholino oligomer of claim 2, wherein $R^2$ is selected from H, G. acyl, trityl, 4-methoxytrityl, benzoyl, and stearoyl.

5. The antisense morpholino oligomer of claim 2, wherein T is selected from:

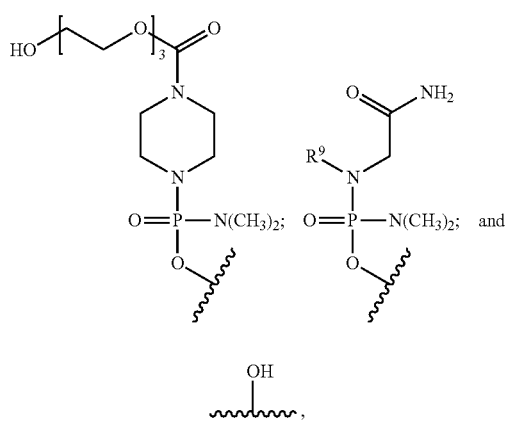

and
$R^2$ is G.

6. The antisense morpholino oligomer of claim 2, wherein T is of the formula:

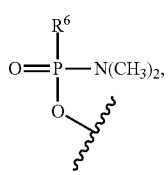

118

$R^6$ is of the formula:

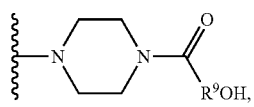

and
$R^2$ is G.

7. The antisense morpholino oligomer of claim 2, wherein T is of the formula:

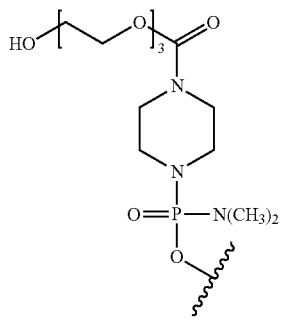

and
$R^2$ is G.

8. The antisense morpholino oligomer of claim 2, wherein T is of the formula:

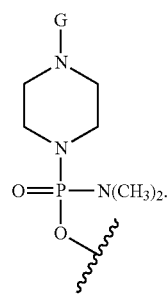

9. The antisense morpholino oligomer according to claim 2, wherein $R^2$ is selected from H, acyl, trityl, 4-methoxytrityl, benzoyl, and stearoyl.

10. The antisense morpholino oligomer according to claim 2, wherein at least one instance of $R^1$ is —N(CH$_3$)$_2$.

11. The antisense morpholino oligomer according to claim 1, wherein the CPP is selected from:

(SEQ ID NO: 44)

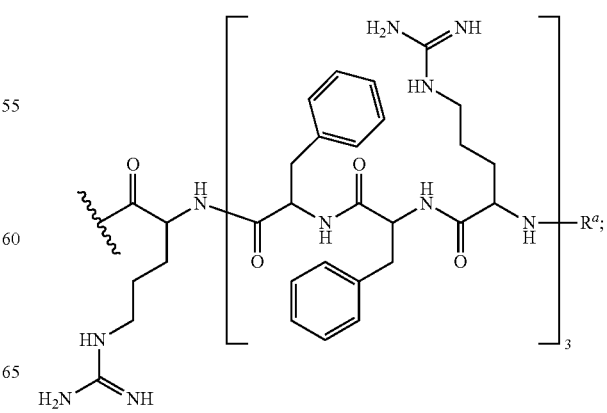

119
-continued
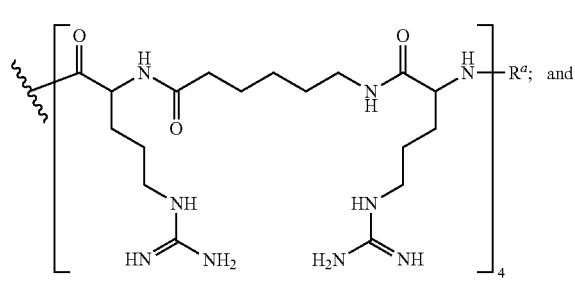
120
-continued
(SEQ ID NO: 49)
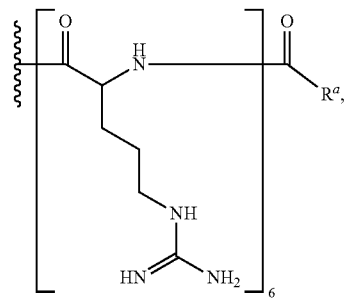
wherein R is selected from H, acetyl, benzoyl, and stearoyl.
12. The antisense morpholino oligomer according to claim 1, wherein G is selected from:
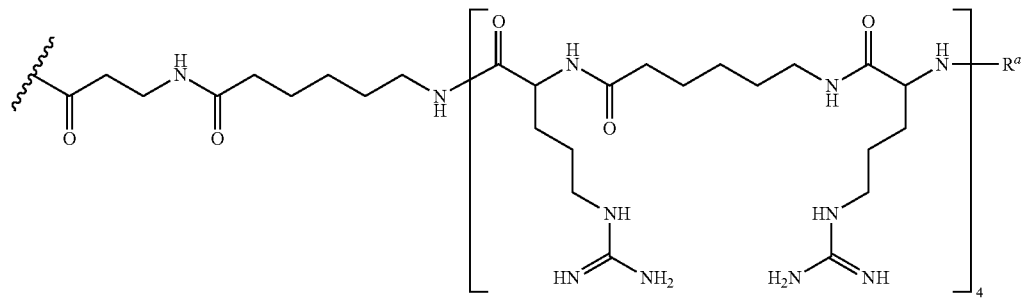
(SEQ ID NO: 44)
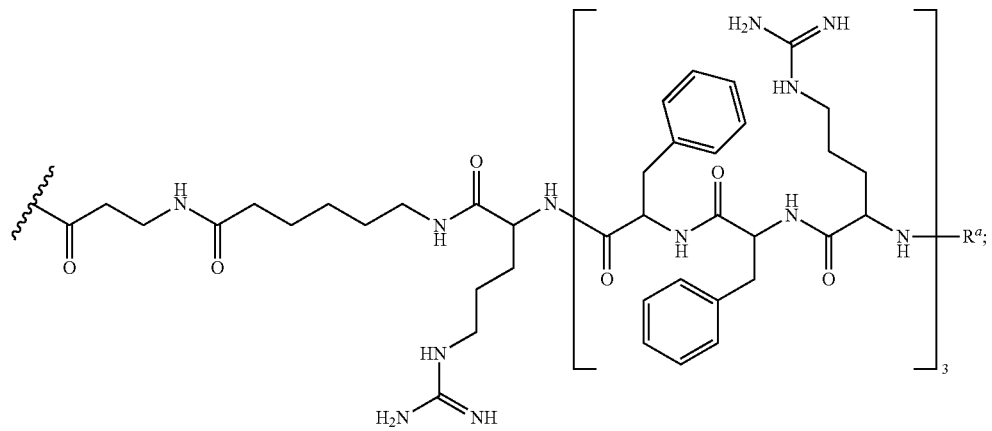
(SEQ ID NO: 51)
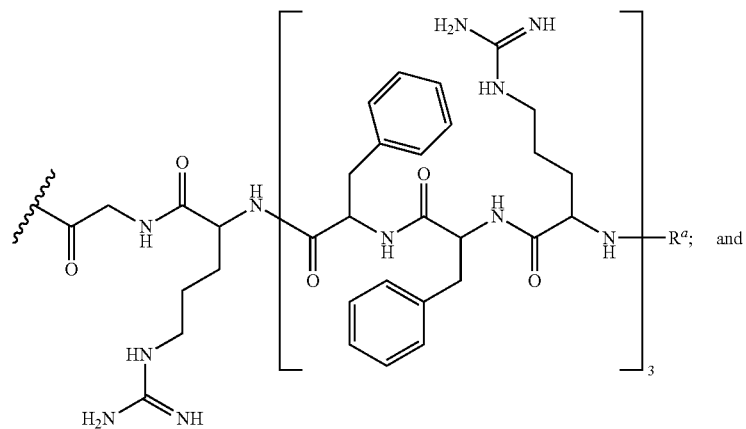

-continued
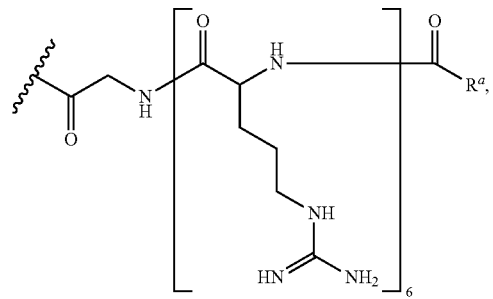
(SEQ ID NO: 49)
wherein $R^a$ is selected from H, acetyl, benzoyl, and stearoyl.
13. The antisense morpholino oligomer of claim 1, wherein the antisense oligomer is of the formula (VII) selected from:

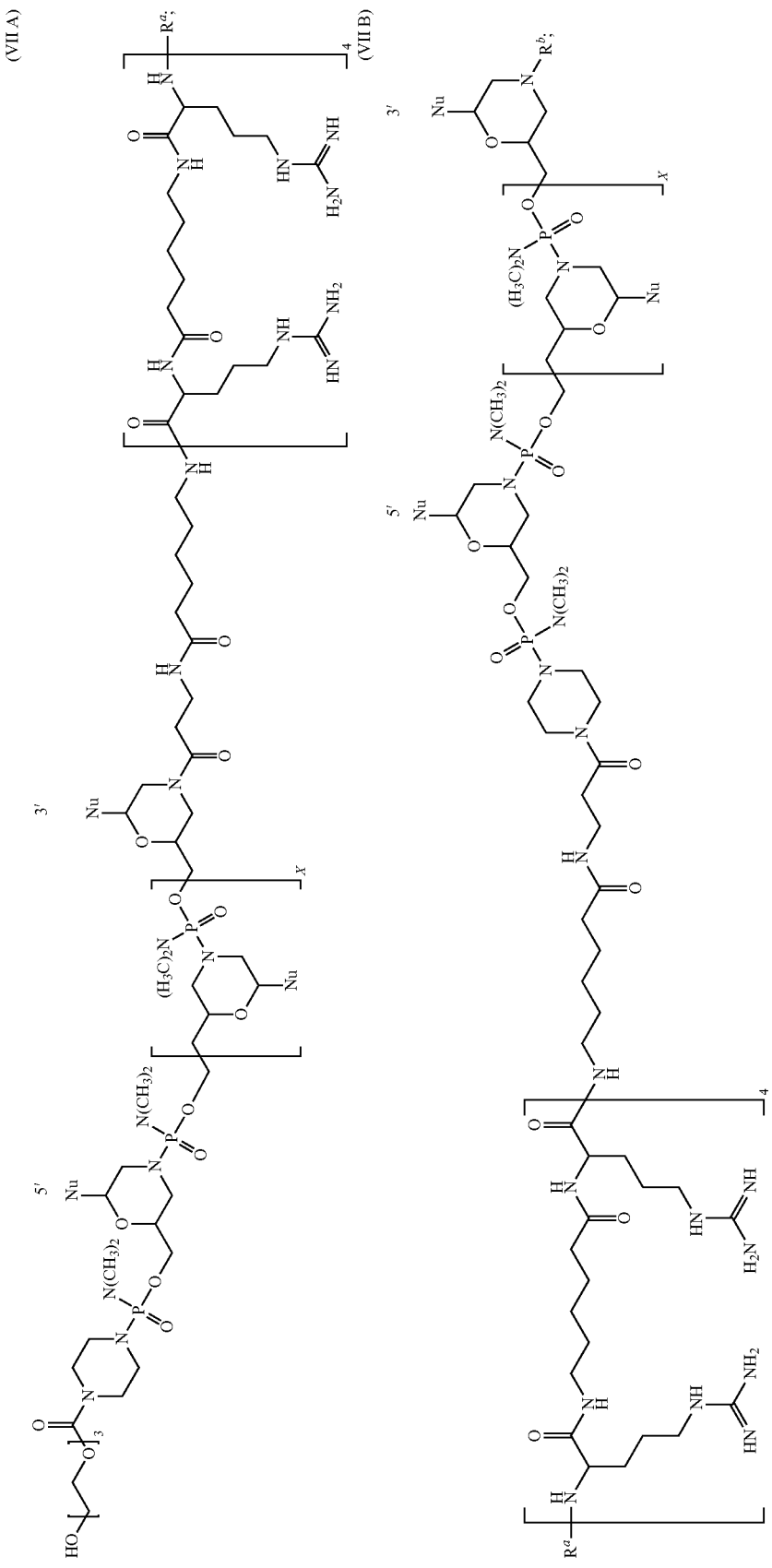

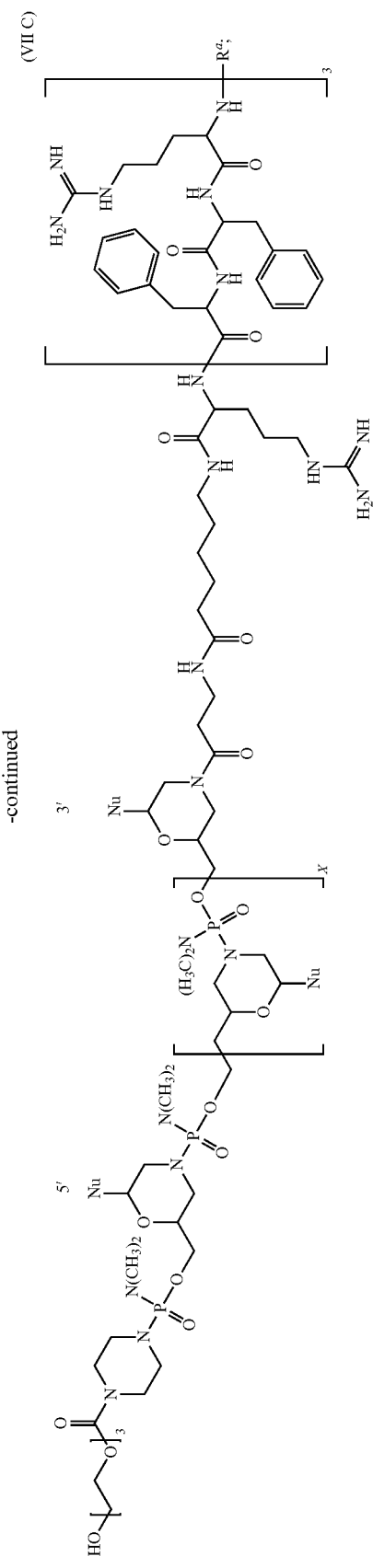
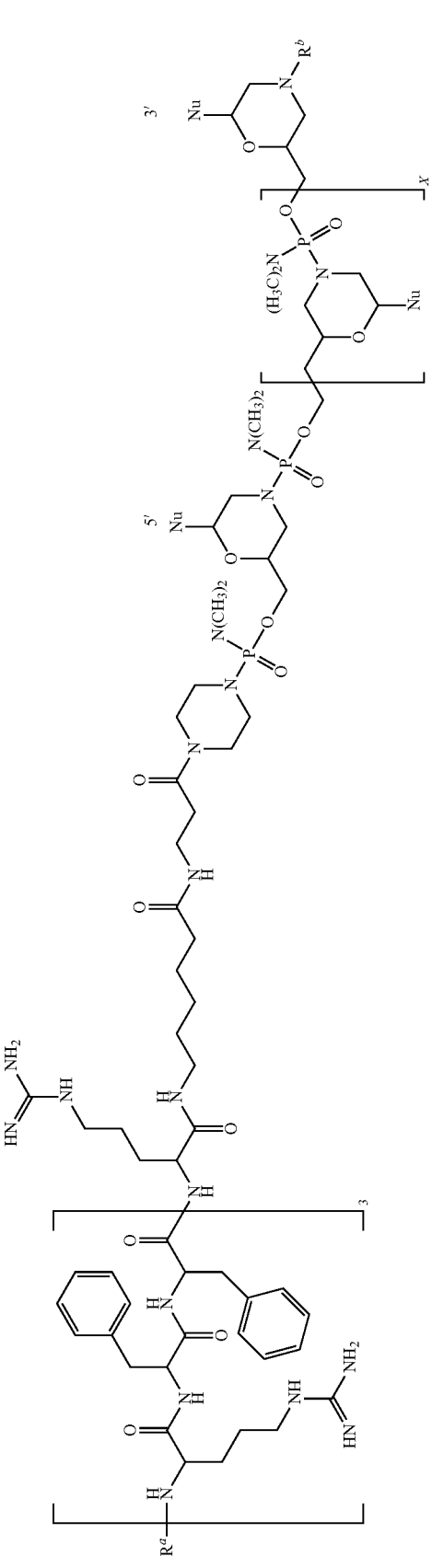

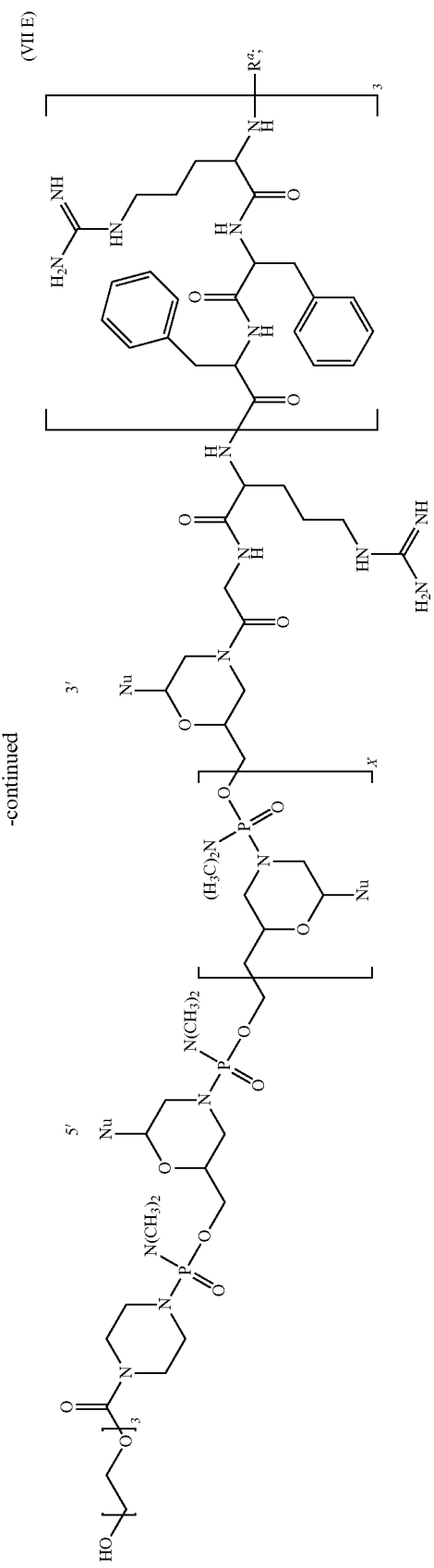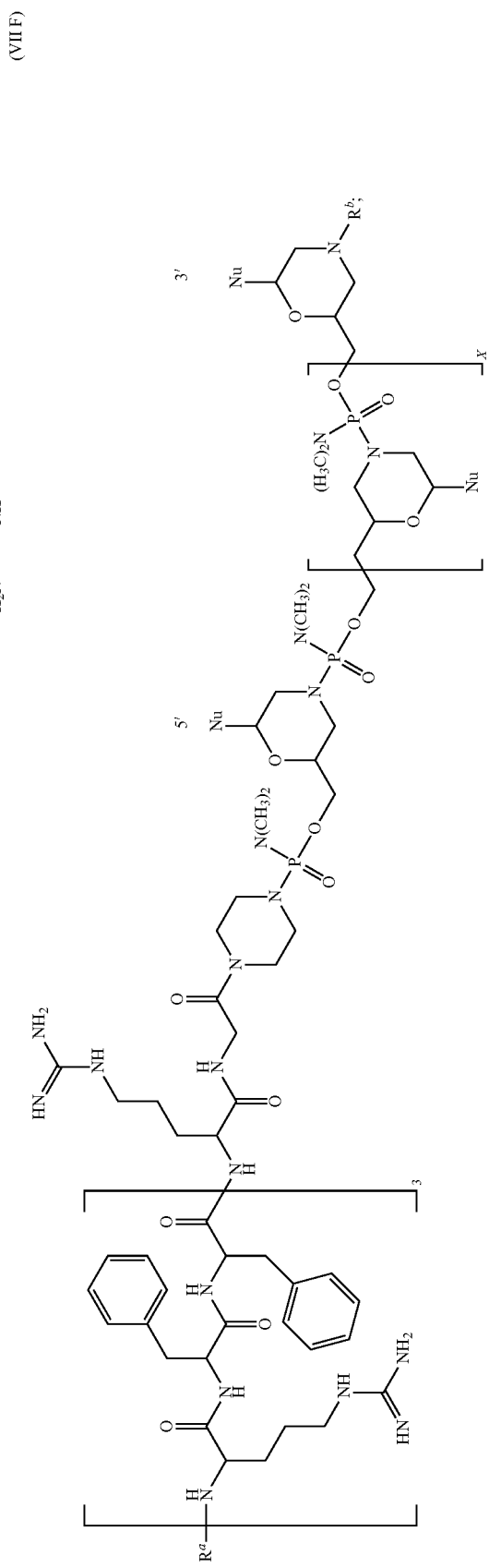

-continued
(VII G)
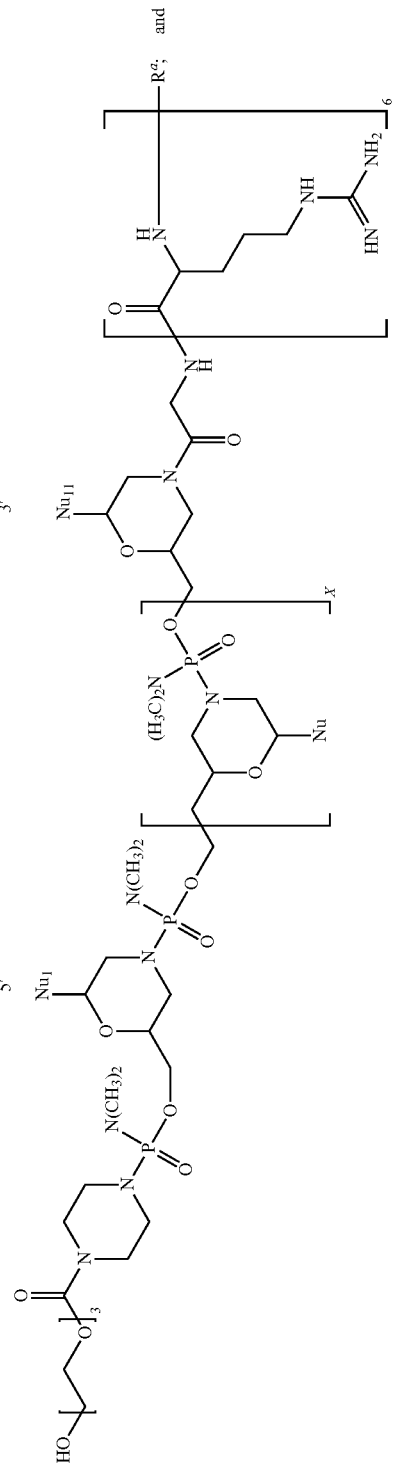
(VII H)
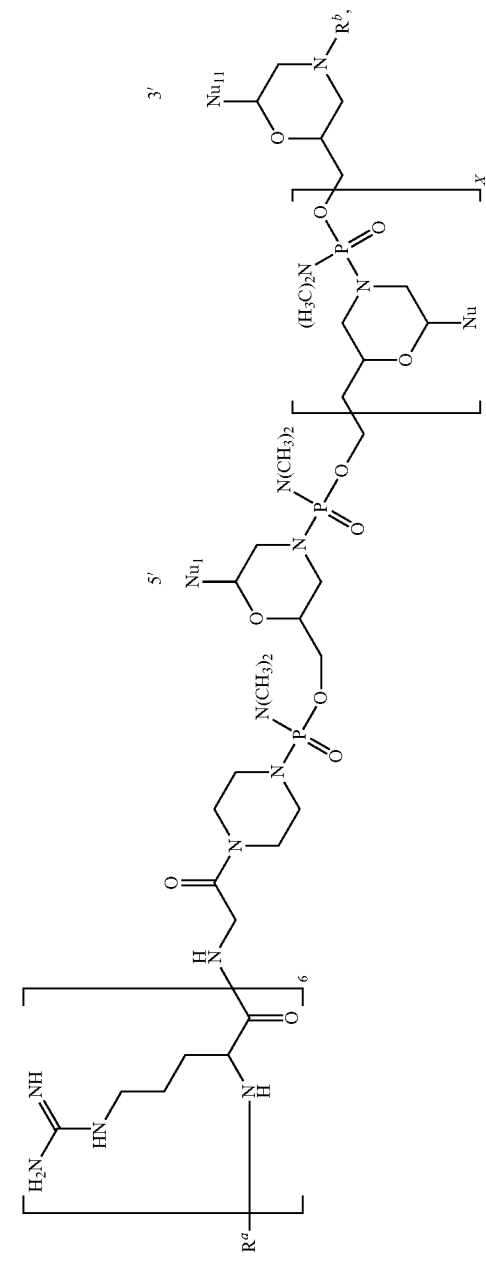

or a pharmaceutically acceptable salt of any of the foregoing, wherein $R^a$ is selected from U, acetyl, benzoyl, and stearoyl, $R^b$ is selected from H, acetyl, benzoyl, stearoyl, trityl, and 4-methoxytrityl, and X and Nu are as defined in claim 1.

14. A pharmaceutical composition, comprising a pharmaceutically acceptable carrier and an antisense morpholino oligomer, wherein the antisense morpholino oligomer is composed of morpholino subunits and phosphorus-containing intersubunit linkages joining a morpholino nitrogen of one subunit to a 5'-exocyclic carbon of an adjacent subunit, and having (a) about 10-40 nucleotide bases, and (b) a targeting sequence selected from:

```
a) SEQ ID NO: 11 (ATG TAA ACC TC);
b) SEQ ID NO: 12 (GTT CAT ATG TA);
c) SEQ ID NO: 13 (AAC CCT CTG TT);
d) SEQ ID NO: 14 (TGT TCA TAT GT);
``` wherein thymine bases (T) may he uracil bases (U), and where the oligomer is conjugated to a cell-penetrating peptide (CPP).

15. A method of reducing expression and activity of a virulence factor in a bacterium, comprising contacting the bacterium with an antisense morpholino oligomer, wherein the antisense morpholino oligomer is composed of morpholino subunits and phosphorus-containing intersubunit linkages joining a morpholino nitrogen of one subunit to a 5'-exocyclic carbon of an adjacent subunit, and having (a) about 10-40 nucleotide bases, and (b) a targeting sequence selected from:

```
a) SEQ ID NO: 11 (ATG TAA ACC TC);
b) SEQ ID NO: 12 (GTT CAT ATG TA);
c) SEQ ID NO: 13 (AAC CCT CTG TT);
d) SEQ ID NO: 14 (TGT TCA TAT GT);
``` wherein thymine bases (T) may be uracil bases (U), and where the oligomer is conjugated to a cell-penetrating peptide (CPP).

16. The antisense morpholino oligomer of claim 1, wherein the targeting sequence is SEQ ID NO: 11.

17. The antisense morpholino oligomer of claim 1, wherein the targeting sequence is SEQ ID NO: 12.

18. The antisense morpholino oligomer of claim 1, wherein the targeting sequence is SEQ ID NO: 13.

19. The antisense morpholino oligomer of claim 1, wherein the targeting sequence is SEQ ID NO: 14.

\* \* \* \* \*

SEQUENCE LISTING

```
<160> NUMBER OF SEQ ID NOS: 51

<210> SEQ ID NO 1
<211> LENGTH: 60
<212> TYPE: DNA
<213> ORGANISM: Escherichia coli
<220> FEATURE:
<221> NAME/KEY: misc_feature
<222> LOCATION: (2)..(6)
<223> OTHER INFORMATION: n may be thymidine or uracil
<220> FEATURE:
<221> NAME/KEY: misc_feature
<222> LOCATION: (9)..(9)
<223> OTHER INFORMATION: n may be thymidine or uracil
<220> FEATURE:
<221> NAME/KEY: misc_feature
<222> LOCATION: (12)..(12)
<223> OTHER INFORMATION: n may be thymidine or uracil
<220> FEATURE:
<221> NAME/KEY: misc_feature
<222> LOCATION: (16)..(16)
<223> OTHER INFORMATION: n may be thymidine or uracil
<220> FEATURE:
<221> NAME/KEY: misc_feature
<222> LOCATION: (28)..(29)
<223> OTHER INFORMATION: n may be thymidine or uracil
<220> FEATURE:
<221> NAME/KEY: misc_feature
<222> LOCATION: (32)..(32)
<223> OTHER INFORMATION: n may be thymidine or uracil
<220> FEATURE:
<221> NAME/KEY: misc_feature
<222> LOCATION: (37)..(38)
<223> OTHER INFORMATION: n may be thymidine or uracil
<220> FEATURE:
<221> NAME/KEY: misc_feature
<222> LOCATION: (45)..(45)
<223> OTHER INFORMATION: n may be thymidine or uracil
<220> FEATURE:
<221> NAME/KEY: misc_feature
<222> LOCATION: (47)..(48)
<223> OTHER INFORMATION: n may be thymidine or uracil
<220> FEATURE:
<221> NAME/KEY: misc_feature
<222> LOCATION: (50)..(50)
<223> OTHER INFORMATION: n may be thymidine or uracil
```

```
<220> FEATURE:
<221> NAME/KEY: misc_feature
<222> LOCATION: (59)..(59)
<223> OTHER INFORMATION: n may be thymidine or uracil

<400> SEQUENCE: 1
gnnnnnaang cngaanaaaa ggaaaacnng anggaanngc ccaanannan gcacccggnc        60

<210> SEQ ID NO 2
<211> LENGTH: 60
<212> TYPE: DNA
<213> ORGANISM: Klebsiella pneumoniae
<220> FEATURE:
<221> NAME/KEY: misc_feature
<222> LOCATION: (2)..(6)
<223> OTHER INFORMATION: n may be thymidine or uracil
<220> FEATURE:
<221> NAME/KEY: misc_feature
<222> LOCATION: (9)..(9)
<223> OTHER INFORMATION: n may be thymidine or uracil
<220> FEATURE:
<221> NAME/KEY: misc_feature
<222> LOCATION: (12)..(12)
<223> OTHER INFORMATION: n may be thymidine or uracil
<220> FEATURE:
<221> NAME/KEY: misc_feature
<222> LOCATION: (16)..(16)
<223> OTHER INFORMATION: n may be thymidine or uracil
<220> FEATURE:
<221> NAME/KEY: misc_feature
<222> LOCATION: (28)..(29)
<223> OTHER INFORMATION: n may be thymidine or uracil
<220> FEATURE:
<221> NAME/KEY: misc_feature
<222> LOCATION: (32)..(32)
<223> OTHER INFORMATION: n may be thymidine or uracil
<220> FEATURE:
<221> NAME/KEY: misc_feature
<222> LOCATION: (37)..(38)
<223> OTHER INFORMATION: n may be thymidine or uracil
<220> FEATURE:
<221> NAME/KEY: misc_feature
<222> LOCATION: (45)..(45)
<223> OTHER INFORMATION: n may be thymidine or uracil
<220> FEATURE:
<221> NAME/KEY: misc_feature
<222> LOCATION: (47)..(48)
<223> OTHER INFORMATION: n may be thymidine or uracil
<220> FEATURE:
<221> NAME/KEY: misc_feature
<222> LOCATION: (50)..(50)
<223> OTHER INFORMATION: n may be thymidine or uracil
<220> FEATURE:
<221> NAME/KEY: misc_feature
<222> LOCATION: (59)..(59)
<223> OTHER INFORMATION: n may be thymidine or uracil

<400> SEQUENCE: 2
gnnnnnaang cngaanaaaa ggaaaacnng anggaanngc ccaanannan gcacccggnc        60

<210> SEQ ID NO 3
<211> LENGTH: 60
<212> TYPE: DNA
<213> ORGANISM: Acinetobacter baumannii
<220> FEATURE:
<221> NAME/KEY: misc_feature
<222> LOCATION: (5)..(5)
<223> OTHER INFORMATION: n may be thymidine or uracil
<220> FEATURE:
<221> NAME/KEY: misc_feature
<222> LOCATION: (13)..(13)
<223> OTHER INFORMATION: n may be thymidine or uracil
<220> FEATURE:
<221> NAME/KEY: misc_feature
<222> LOCATION: (17)..(17)
```

<223> OTHER INFORMATION: n may be thymidine or uracil
<220> FEATURE:
<221> NAME/KEY: misc_feature
<222> LOCATION: (21)..(23)
<223> OTHER INFORMATION: n may be thymidine or uracil
<220> FEATURE:
<221> NAME/KEY: misc_feature
<222> LOCATION: (30)..(30)
<223> OTHER INFORMATION: n may be thymidine or uracil
<220> FEATURE:
<221> NAME/KEY: misc_feature
<222> LOCATION: (32)..(32)
<223> OTHER INFORMATION: n may be thymidine or uracil
<220> FEATURE:
<221> NAME/KEY: misc_feature
<222> LOCATION: (42)..(42)
<223> OTHER INFORMATION: n may be thymidine or uracil
<220> FEATURE:
<221> NAME/KEY: misc_feature
<222> LOCATION: (44)..(47)
<223> OTHER INFORMATION: n may be thymidine or uracil
<220> FEATURE:
<221> NAME/KEY: misc_feature
<222> LOCATION: (50)..(51)
<223> OTHER INFORMATION: n may be thymidine or uracil
<220> FEATURE:
<221> NAME/KEY: misc_feature
<222> LOCATION: (54)..(56)
<223> OTHER INFORMATION: n may be thymidine or uracil
<220> FEATURE:
<221> NAME/KEY: misc_feature
<222> LOCATION: (58)..(60)
<223> OTHER INFORMATION: n may be thymidine or uracil

<400> SEQUENCE: 3
aacancaaaa agncacnagg nnnggacagn angcaaaagc ancnnnnacn nccnnnannn    60

<210> SEQ ID NO 4
<211> LENGTH: 60
<212> TYPE: DNA
<213> ORGANISM: Acinetobacter baumannii
<220> FEATURE:
<221> NAME/KEY: misc_feature
<222> LOCATION: (5)..(5)
<223> OTHER INFORMATION: n may be thymidine or uracil
<220> FEATURE:
<221> NAME/KEY: misc_feature
<222> LOCATION: (13)..(13)
<223> OTHER INFORMATION: n may be thymidine or uracil
<220> FEATURE:
<221> NAME/KEY: misc_feature
<222> LOCATION: (17)..(17)
<223> OTHER INFORMATION: n may be thymidine or uracil
<220> FEATURE:
<221> NAME/KEY: misc_feature
<222> LOCATION: (21)..(23)
<223> OTHER INFORMATION: n may be thymidine or uracil
<220> FEATURE:
<221> NAME/KEY: misc_feature
<222> LOCATION: (30)..(30)
<223> OTHER INFORMATION: n may be thymidine or uracil
<220> FEATURE:
<221> NAME/KEY: misc_feature
<222> LOCATION: (32)..(32)
<223> OTHER INFORMATION: n may be thymidine or uracil
<220> FEATURE:
<221> NAME/KEY: misc_feature
<222> LOCATION: (42)..(42)
<223> OTHER INFORMATION: n may be thymidine or uracil
<220> FEATURE:
<221> NAME/KEY: misc_feature
<222> LOCATION: (44)..(47)
<223> OTHER INFORMATION: n may be thymidine or uracil
<220> FEATURE:
<221> NAME/KEY: misc_feature
<222> LOCATION: (50)..(51)
<223> OTHER INFORMATION: n may be thymidine or uracil

```
<220> FEATURE:
<221> NAME/KEY: misc_feature
<222> LOCATION: (54)..(56)
<223> OTHER INFORMATION: n may be thymidine or uracil
<220> FEATURE:
<221> NAME/KEY: misc_feature
<222> LOCATION: (58)..(60)
<223> OTHER INFORMATION: n may be thymidine or uracil

<400> SEQUENCE: 4
aacancaaaa agncacnagg nnnggacagn angcaaaagc ancnnnnacn nccnnnannn    60

<210> SEQ ID NO 5
<211> LENGTH: 60
<212> TYPE: DNA
<213> ORGANISM: Burkholderia cenocepacia
<220> FEATURE:
<221> NAME/KEY: misc_feature
<222> LOCATION: (4)..(4)
<223> OTHER INFORMATION: n may be thymidine or uracil
<220> FEATURE:
<221> NAME/KEY: misc_feature
<222> LOCATION: (18)..(18)
<223> OTHER INFORMATION: n may be thymidine or uracil
<220> FEATURE:
<221> NAME/KEY: misc_feature
<222> LOCATION: (28)..(28)
<223> OTHER INFORMATION: n may be thymidine or uracil
<220> FEATURE:
<221> NAME/KEY: misc_feature
<222> LOCATION: (32)..(32)
<223> OTHER INFORMATION: n may be thymidine or uracil
<220> FEATURE:
<221> NAME/KEY: misc_feature
<222> LOCATION: (40)..(41)
<223> OTHER INFORMATION: n may be thymidine or uracil
<220> FEATURE:
<221> NAME/KEY: misc_feature
<222> LOCATION: (44)..(45)
<223> OTHER INFORMATION: n may be thymidine or uracil

<400> SEQUENCE: 5
gcanacaaaa gcacagancc gaggacancc angcagaccn ncgnncacga ggaagggcgg    60

<210> SEQ ID NO 6
<211> LENGTH: 60
<212> TYPE: DNA
<213> ORGANISM: Actinetobacter baumannii
<220> FEATURE:
<221> NAME/KEY: misc_feature
<222> LOCATION: (1)..(1)
<223> OTHER INFORMATION: n may be thymidine or uracil
<220> FEATURE:
<221> NAME/KEY: misc_feature
<222> LOCATION: (5)..(6)
<223> OTHER INFORMATION: n may be thymidine or uracil
<220> FEATURE:
<221> NAME/KEY: misc_feature
<222> LOCATION: (13)..(13)
<223> OTHER INFORMATION: n may be thymidine or uracil
<220> FEATURE:
<221> NAME/KEY: misc_feature
<222> LOCATION: (17)..(17)
<223> OTHER INFORMATION: n may be thymidine or uracil
<220> FEATURE:
<221> NAME/KEY: misc_feature
<222> LOCATION: (26)..(27)
<223> OTHER INFORMATION: n may be thymidine or uracil
<220> FEATURE:
<221> NAME/KEY: misc_feature
<222> LOCATION: (29)..(29)
<223> OTHER INFORMATION: n may be thymidine or uracil
<220> FEATURE:
<221> NAME/KEY: misc_feature
<222> LOCATION: (32)..(32)
```

<223> OTHER INFORMATION: n may be thymidine or uracil
<220> FEATURE:
<221> NAME/KEY: misc_feature
<222> LOCATION: (36)..(36)
<223> OTHER INFORMATION: n may be thymidine or uracil
<220> FEATURE:
<221> NAME/KEY: misc_feature
<222> LOCATION: (38)..(39)
<223> OTHER INFORMATION: n may be thymidine or uracil
<220> FEATURE:
<221> NAME/KEY: misc_feature
<222> LOCATION: (41)..(42)
<223> OTHER INFORMATION: n may be thymidine or uracil
<220> FEATURE:
<221> NAME/KEY: misc_feature
<222> LOCATION: (45)..(45)
<223> OTHER INFORMATION: n may be thymidine or uracil
<220> FEATURE:
<221> NAME/KEY: misc_feature
<222> LOCATION: (49)..(51)
<223> OTHER INFORMATION: n may be thymidine or uracil
<220> FEATURE:
<221> NAME/KEY: misc_feature
<222> LOCATION: (60)..(60)
<223> OTHER INFORMATION: n may be thymidine or uracil

<400> SEQUENCE: 6
ncacnngaaa aanaagngga agcacnngna angaananna nngcnggann ncaaaacaan    60

<210> SEQ ID NO 7
<211> LENGTH: 60
<212> TYPE: DNA
<213> ORGANISM: Actinetobacter baumannii
<220> FEATURE:
<221> NAME/KEY: misc_feature
<222> LOCATION: (1)..(1)
<223> OTHER INFORMATION: n may be thymidine or uracil
<220> FEATURE:
<221> NAME/KEY: misc_feature
<222> LOCATION: (3)..(4)
<223> OTHER INFORMATION: n may be thymidine or uracil
<220> FEATURE:
<221> NAME/KEY: misc_feature
<222> LOCATION: (9)..(11)
<223> OTHER INFORMATION: n may be thymidine or uracil
<220> FEATURE:
<221> NAME/KEY: misc_feature
<222> LOCATION: (13)..(13)
<223> OTHER INFORMATION: n may be thymidine or uracil
<220> FEATURE:
<221> NAME/KEY: misc_feature
<222> LOCATION: (15)..(16)
<223> OTHER INFORMATION: n may be thymidine or uracil
<220> FEATURE:
<221> NAME/KEY: misc_feature
<222> LOCATION: (18)..(18)
<223> OTHER INFORMATION: n may be thymidine or uracil
<220> FEATURE:
<221> NAME/KEY: misc_feature
<222> LOCATION: (21)..(21)
<223> OTHER INFORMATION: n may be thymidine or uracil
<220> FEATURE:
<221> NAME/KEY: misc_feature
<222> LOCATION: (25)..(25)
<223> OTHER INFORMATION: n may be thymidine or uracil
<220> FEATURE:
<221> NAME/KEY: misc_feature
<222> LOCATION: (27)..(28)
<223> OTHER INFORMATION: n may be thymidine or uracil
<220> FEATURE:
<221> NAME/KEY: misc_feature
<222> LOCATION: (32)..(32)
<223> OTHER INFORMATION: n may be thymidine or uracil
<220> FEATURE:
<221> NAME/KEY: misc_feature
<222> LOCATION: (39)..(39)
<223> OTHER INFORMATION: n may be thymidine or uracil

```
<220> FEATURE:
<221> NAME/KEY: misc_feature
<222> LOCATION: (41)..(41)
<223> OTHER INFORMATION: n may be thymidine or uracil
<220> FEATURE:
<221> NAME/KEY: misc_feature
<222> LOCATION: (44)..(44)
<223> OTHER INFORMATION: n may be thymidine or uracil
<220> FEATURE:
<221> NAME/KEY: misc_feature
<222> LOCATION: (47)..(47)
<223> OTHER INFORMATION: n may be thymidine or uracil
<220> FEATURE:
<221> NAME/KEY: misc_feature
<222> LOCATION: (50)..(50)
<223> OTHER INFORMATION: n may be thymidine or uracil
<220> FEATURE:
<221> NAME/KEY: misc_feature
<222> LOCATION: (54)..(54)
<223> OTHER INFORMATION: n may be thymidine or uracil
<220> FEATURE:
<221> NAME/KEY: misc_feature
<222> LOCATION: (60)..(60)
<223> OTHER INFORMATION: n may be thymidine or uracil

<400> SEQUENCE: 7
ncnncaaann ngnanngnag ngggngnnca anggaaccna nggnggngan ggcngcgcgn        60

<210> SEQ ID NO 8
<211> LENGTH: 60
<212> TYPE: DNA
<213> ORGANISM: Burkholderia cenocepacia
<220> FEATURE:
<221> NAME/KEY: misc_feature
<222> LOCATION: (5)..(5)
<223> OTHER INFORMATION: n may be thymidine or uracil
<220> FEATURE:
<221> NAME/KEY: misc_feature
<222> LOCATION: (15)..(15)
<223> OTHER INFORMATION: n may be thymidine or uracil
<220> FEATURE:
<221> NAME/KEY: misc_feature
<222> LOCATION: (22)..(22)
<223> OTHER INFORMATION: n may be thymidine or uracil
<220> FEATURE:
<221> NAME/KEY: misc_feature
<222> LOCATION: (29)..(29)
<223> OTHER INFORMATION: n may be thymidine or uracil
<220> FEATURE:
<221> NAME/KEY: misc_feature
<222> LOCATION: (32)..(32)
<223> OTHER INFORMATION: n may be thymidine or uracil
<220> FEATURE:
<221> NAME/KEY: misc_feature
<222> LOCATION: (36)..(36)
<223> OTHER INFORMATION: n may be thymidine or uracil
<220> FEATURE:
<221> NAME/KEY: misc_feature
<222> LOCATION: (41)..(41)
<223> OTHER INFORMATION: n may be thymidine or uracil
<220> FEATURE:
<221> NAME/KEY: misc_feature
<222> LOCATION: (44)..(44)
<223> OTHER INFORMATION: n may be thymidine or uracil
<220> FEATURE:
<221> NAME/KEY: misc_feature
<222> LOCATION: (50)..(51)
<223> OTHER INFORMATION: n may be thymidine or uracil
<220> FEATURE:
<221> NAME/KEY: misc_feature
<222> LOCATION: (54)..(54)
<223> OTHER INFORMATION: n may be thymidine or uracil
<220> FEATURE:
<221> NAME/KEY: misc_feature
<222> LOCATION: (56)..(56)
<223> OTHER INFORMATION: n may be thymidine or uracil
```

-continued

<400> SEQUENCE: 8
cccgngccgc cggcnacagg anccaggcnc angcanccca ngcncaacan ngcngncaag    60

<210> SEQ ID NO 9
<211> LENGTH: 767
<212> TYPE: DNA
<213> ORGANISM: Actinetobacter baumannii
<220> FEATURE:
<221> NAME/KEY: misc_feature
<222> LOCATION: (5)..(5)
<223> OTHER INFORMATION: n may be thymidine or uracil
<220> FEATURE:
<221> NAME/KEY: misc_feature
<222> LOCATION: (15)..(15)
<223> OTHER INFORMATION: n may be thymidine or uracil
<220> FEATURE:
<221> NAME/KEY: misc_feature
<222> LOCATION: (22)..(22)
<223> OTHER INFORMATION: n may be thymidine or uracil
<220> FEATURE:
<221> NAME/KEY: misc_feature
<222> LOCATION: (29)..(29)
<223> OTHER INFORMATION: n may be thymidine or uracil
<220> FEATURE:
<221> NAME/KEY: misc_feature
<222> LOCATION: (32)..(32)
<223> OTHER INFORMATION: n may be thymidine or uracil
<220> FEATURE:
<221> NAME/KEY: misc_feature
<222> LOCATION: (36)..(36)
<223> OTHER INFORMATION: n may be thymidine or uracil
<220> FEATURE:
<221> NAME/KEY: misc_feature
<222> LOCATION: (41)..(41)
<223> OTHER INFORMATION: n may be thymidine or uracil
<220> FEATURE:
<221> NAME/KEY: misc_feature
<222> LOCATION: (44)..(44)
<223> OTHER INFORMATION: n may be thymidine or uracil
<220> FEATURE:
<221> NAME/KEY: misc_feature
<222> LOCATION: (50)..(51)
<223> OTHER INFORMATION: n may be thymidine or uracil
<220> FEATURE:
<221> NAME/KEY: misc_feature
<222> LOCATION: (54)..(54)
<223> OTHER INFORMATION: n may be thymidine or uracil
<220> FEATURE:
<221> NAME/KEY: misc_feature
<222> LOCATION: (56)..(56)
<223> OTHER INFORMATION: n may be thymidine or uracil
<220> FEATURE:
<221> NAME/KEY: misc_feature
<222> LOCATION: (63)..(63)
<223> OTHER INFORMATION: n may be thymidine or uracil
<220> FEATURE:
<221> NAME/KEY: misc_feature
<222> LOCATION: (83)..(83)
<223> OTHER INFORMATION: n may be thymidine or uracil
<220> FEATURE:
<221> NAME/KEY: misc_feature
<222> LOCATION: (86)..(86)
<223> OTHER INFORMATION: n may be thymidine or uracil
<220> FEATURE:
<221> NAME/KEY: misc_feature
<222> LOCATION: (90)..(90)
<223> OTHER INFORMATION: n may be thymidine or uracil
<220> FEATURE:
<221> NAME/KEY: misc_feature
<222> LOCATION: (97)..(97)
<223> OTHER INFORMATION: n may be thymidine or uracil
<220> FEATURE:
<221> NAME/KEY: misc_feature
<222> LOCATION: (101)..(101)
<223> OTHER INFORMATION: n may be thymidine or uracil
<220> FEATURE:
<221> NAME/KEY: misc_feature

```
<222> LOCATION: (105)..(105)
<223> OTHER INFORMATION: n may be thymidine or uracil
<220> FEATURE:
<221> NAME/KEY: misc_feature
<222> LOCATION: (107)..(107)
<223> OTHER INFORMATION: n may be thymidine or uracil
<220> FEATURE:
<221> NAME/KEY: misc_feature
<222> LOCATION: (113)..(113)
<223> OTHER INFORMATION: n may be thymidine or uracil
<220> FEATURE:
<221> NAME/KEY: misc_feature
<222> LOCATION: (116)..(116)
<223> OTHER INFORMATION: n may be thymidine or uracil
<220> FEATURE:
<221> NAME/KEY: misc_feature
<222> LOCATION: (122)..(122)
<223> OTHER INFORMATION: n may be thymidine or uracil
<220> FEATURE:
<221> NAME/KEY: misc_feature
<222> LOCATION: (145)..(146)
<223> OTHER INFORMATION: n may be thymidine or uracil
<220> FEATURE:
<221> NAME/KEY: misc_feature
<222> LOCATION: (149)..(149)
<223> OTHER INFORMATION: n may be thymidine or uracil
<220> FEATURE:
<221> NAME/KEY: misc_feature
<222> LOCATION: (158)..(158)
<223> OTHER INFORMATION: n may be thymidine or uracil
<220> FEATURE:
<221> NAME/KEY: misc_feature
<222> LOCATION: (182)..(182)
<223> OTHER INFORMATION: n may be thymidine or uracil
<220> FEATURE:
<221> NAME/KEY: misc_feature
<222> LOCATION: (185)..(185)
<223> OTHER INFORMATION: n may be thymidine or uracil
<220> FEATURE:
<221> NAME/KEY: misc_feature
<222> LOCATION: (194)..(194)
<223> OTHER INFORMATION: n may be thymidine or uracil
<220> FEATURE:
<221> NAME/KEY: misc_feature
<222> LOCATION: (205)..(205)
<223> OTHER INFORMATION: n may be thymidine or uracil
<220> FEATURE:
<221> NAME/KEY: misc_feature
<222> LOCATION: (221)..(221)
<223> OTHER INFORMATION: n may be thymidine or uracil
<220> FEATURE:
<221> NAME/KEY: misc_feature
<222> LOCATION: (224)..(224)
<223> OTHER INFORMATION: n may be thymidine or uracil
<220> FEATURE:
<221> NAME/KEY: misc_feature
<222> LOCATION: (235)..(235)
<223> OTHER INFORMATION: n may be thymidine or uracil
<220> FEATURE:
<221> NAME/KEY: misc_feature
<222> LOCATION: (244)..(244)
<223> OTHER INFORMATION: n may be thymidine or uracil
<220> FEATURE:
<221> NAME/KEY: misc_feature
<222> LOCATION: (256)..(256)
<223> OTHER INFORMATION: n may be thymidine or uracil
<220> FEATURE:
<221> NAME/KEY: misc_feature
<222> LOCATION: (262)..(263)
<223> OTHER INFORMATION: n may be thymidine or uracil
<220> FEATURE:
<221> NAME/KEY: misc_feature
<222> LOCATION: (268)..(268)
<223> OTHER INFORMATION: n may be thymidine or uracil
<220> FEATURE:
<221> NAME/KEY: misc_feature
<222> LOCATION: (272)..(272)
<223> OTHER INFORMATION: n may be thymidine or uracil
<220> FEATURE:
```

```
<221> NAME/KEY: misc_feature
<222> LOCATION: (275)..(275)
<223> OTHER INFORMATION: n may be thymidine or uracil
<220> FEATURE:
<221> NAME/KEY: misc_feature
<222> LOCATION: (279)..(279)
<223> OTHER INFORMATION: n may be thymidine or uracil
<220> FEATURE:
<221> NAME/KEY: misc_feature
<222> LOCATION: (284)..(284)
<223> OTHER INFORMATION: n may be thymidine or uracil
<220> FEATURE:
<221> NAME/KEY: misc_feature
<222> LOCATION: (301)..(302)
<223> OTHER INFORMATION: n may be thymidine or uracil
<220> FEATURE:
<221> NAME/KEY: misc_feature
<222> LOCATION: (305)..(305)
<223> OTHER INFORMATION: n may be thymidine or uracil
<220> FEATURE:
<221> NAME/KEY: misc_feature
<222> LOCATION: (313)..(314)
<223> OTHER INFORMATION: n may be thymidine or uracil
<220> FEATURE:
<221> NAME/KEY: misc_feature
<222> LOCATION: (319)..(319)
<223> OTHER INFORMATION: n may be thymidine or uracil
<220> FEATURE:
<221> NAME/KEY: misc_feature
<222> LOCATION: (321)..(322)
<223> OTHER INFORMATION: n may be thymidine or uracil
<220> FEATURE:
<221> NAME/KEY: misc_feature
<222> LOCATION: (325)..(325)
<223> OTHER INFORMATION: n may be thymidine or uracil
<220> FEATURE:
<221> NAME/KEY: misc_feature
<222> LOCATION: (329)..(329)
<223> OTHER INFORMATION: n may be thymidine or uracil
<220> FEATURE:
<221> NAME/KEY: misc_feature
<222> LOCATION: (331)..(331)
<223> OTHER INFORMATION: n may be thymidine or uracil
<220> FEATURE:
<221> NAME/KEY: misc_feature
<222> LOCATION: (335)..(335)
<223> OTHER INFORMATION: n may be thymidine or uracil
<220> FEATURE:
<221> NAME/KEY: misc_feature
<222> LOCATION: (341)..(341)
<223> OTHER INFORMATION: n may be thymidine or uracil
<220> FEATURE:
<221> NAME/KEY: misc_feature
<222> LOCATION: (356)..(356)
<223> OTHER INFORMATION: n may be thymidine or uracil
<220> FEATURE:
<221> NAME/KEY: misc_feature
<222> LOCATION: (359)..(359)
<223> OTHER INFORMATION: n may be thymidine or uracil
<220> FEATURE:
<221> NAME/KEY: misc_feature
<222> LOCATION: (371)..(371)
<223> OTHER INFORMATION: n may be thymidine or uracil
<220> FEATURE:
<221> NAME/KEY: misc_feature
<222> LOCATION: (374)..(374)
<223> OTHER INFORMATION: n may be thymidine or uracil
<220> FEATURE:
<221> NAME/KEY: misc_feature
<222> LOCATION: (376)..(376)
<223> OTHER INFORMATION: n may be thymidine or uracil
<220> FEATURE:
<221> NAME/KEY: misc_feature
<222> LOCATION: (381)..(381)
<223> OTHER INFORMATION: n may be thymidine or uracil
<220> FEATURE:
<221> NAME/KEY: misc_feature
<222> LOCATION: (398)..(398)
<223> OTHER INFORMATION: n may be thymidine or uracil
```

-continued

```
<220> FEATURE:
<221> NAME/KEY: misc_feature
<222> LOCATION: (400)..(401)
<223> OTHER INFORMATION: n may be thymidine or uracil
<220> FEATURE:
<221> NAME/KEY: misc_feature
<222> LOCATION: (427)..(427)
<223> OTHER INFORMATION: n may be thymidine or uracil
<220> FEATURE:
<221> NAME/KEY: misc_feature
<222> LOCATION: (431)..(431)
<223> OTHER INFORMATION: n may be thymidine or uracil
<220> FEATURE:
<221> NAME/KEY: misc_feature
<222> LOCATION: (446)..(446)
<223> OTHER INFORMATION: n may be thymidine or uracil
<220> FEATURE:
<221> NAME/KEY: misc_feature
<222> LOCATION: (452)..(452)
<223> OTHER INFORMATION: n may be thymidine or uracil
<220> FEATURE:
<221> NAME/KEY: misc_feature
<222> LOCATION: (470)..(470)
<223> OTHER INFORMATION: n may be thymidine or uracil
<220> FEATURE:
<221> NAME/KEY: misc_feature
<222> LOCATION: (482)..(482)
<223> OTHER INFORMATION: n may be thymidine or uracil
<220> FEATURE:
<221> NAME/KEY: misc_feature
<222> LOCATION: (485)..(485)
<223> OTHER INFORMATION: n may be thymidine or uracil
<220> FEATURE:
<221> NAME/KEY: misc_feature
<222> LOCATION: (496)..(497)
<223> OTHER INFORMATION: n may be thymidine or uracil
<220> FEATURE:
<221> NAME/KEY: misc_feature
<222> LOCATION: (502)..(503)
<223> OTHER INFORMATION: n may be thymidine or uracil
<220> FEATURE:
<221> NAME/KEY: misc_feature
<222> LOCATION: (521)..(521)
<223> OTHER INFORMATION: n may be thymidine or uracil
<220> FEATURE:
<221> NAME/KEY: misc_feature
<222> LOCATION: (529)..(529)
<223> OTHER INFORMATION: n may be thymidine or uracil
<220> FEATURE:
<221> NAME/KEY: misc_feature
<222> LOCATION: (539)..(539)
<223> OTHER INFORMATION: n may be thymidine or uracil
<220> FEATURE:
<221> NAME/KEY: misc_feature
<222> LOCATION: (541)..(542)
<223> OTHER INFORMATION: n may be thymidine or uracil
<220> FEATURE:
<221> NAME/KEY: misc_feature
<222> LOCATION: (551)..(551)
<223> OTHER INFORMATION: n may be thymidine or uracil
<220> FEATURE:
<221> NAME/KEY: misc_feature
<222> LOCATION: (562)..(562)
<223> OTHER INFORMATION: n may be thymidine or uracil
<220> FEATURE:
<221> NAME/KEY: misc_feature
<222> LOCATION: (572)..(572)
<223> OTHER INFORMATION: n may be thymidine or uracil
<220> FEATURE:
<221> NAME/KEY: misc_feature
<222> LOCATION: (579)..(579)
<223> OTHER INFORMATION: n may be thymidine or uracil
<220> FEATURE:
<221> NAME/KEY: misc_feature
<222> LOCATION: (596)..(596)
<223> OTHER INFORMATION: n may be thymidine or uracil
<220> FEATURE:
<221> NAME/KEY: misc_feature
<222> LOCATION: (600)..(600)
```

-continued

```
<223> OTHER INFORMATION: n may be thymidine or uracil
<220> FEATURE:
<221> NAME/KEY: misc_feature
<222> LOCATION: (602)..(602)
<223> OTHER INFORMATION: n may be thymidine or uracil
<220> FEATURE:
<221> NAME/KEY: misc_feature
<222> LOCATION: (611)..(611)
<223> OTHER INFORMATION: n may be thymidine or uracil
<220> FEATURE:
<221> NAME/KEY: misc_feature
<222> LOCATION: (626)..(626)
<223> OTHER INFORMATION: n may be thymidine or uracil
<220> FEATURE:
<221> NAME/KEY: misc_feature
<222> LOCATION: (634)..(635)
<223> OTHER INFORMATION: n may be thymidine or uracil
<220> FEATURE:
<221> NAME/KEY: misc_feature
<222> LOCATION: (637)..(638)
<223> OTHER INFORMATION: n may be thymidine or uracil
<220> FEATURE:
<221> NAME/KEY: misc_feature
<222> LOCATION: (650)..(650)
<223> OTHER INFORMATION: n may be thymidine or uracil
<220> FEATURE:
<221> NAME/KEY: misc_feature
<222> LOCATION: (656)..(656)
<223> OTHER INFORMATION: n may be thymidine or uracil
<220> FEATURE:
<221> NAME/KEY: misc_feature
<222> LOCATION: (658)..(658)
<223> OTHER INFORMATION: n may be thymidine or uracil
<220> FEATURE:
<221> NAME/KEY: misc_feature
<222> LOCATION: (665)..(665)
<223> OTHER INFORMATION: n may be thymidine or uracil
<220> FEATURE:
<221> NAME/KEY: misc_feature
<222> LOCATION: (680)..(680)
<223> OTHER INFORMATION: n may be thymidine or uracil
<220> FEATURE:
<221> NAME/KEY: misc_feature
<222> LOCATION: (683)..(683)
<223> OTHER INFORMATION: n may be thymidine or uracil
<220> FEATURE:
<221> NAME/KEY: misc_feature
<222> LOCATION: (686)..(686)
<223> OTHER INFORMATION: n may be thymidine or uracil
<220> FEATURE:
<221> NAME/KEY: misc_feature
<222> LOCATION: (704)..(704)
<223> OTHER INFORMATION: n may be thymidine or uracil
<220> FEATURE:
<221> NAME/KEY: misc_feature
<222> LOCATION: (707)..(707)
<223> OTHER INFORMATION: n may be thymidine or uracil
<220> FEATURE:
<221> NAME/KEY: misc_feature
<222> LOCATION: (715)..(715)
<223> OTHER INFORMATION: n may be thymidine or uracil
<220> FEATURE:
<221> NAME/KEY: misc_feature
<222> LOCATION: (732)..(734)
<223> OTHER INFORMATION: n may be thymidine or uracil
<220> FEATURE:
<221> NAME/KEY: misc_feature
<222> LOCATION: (737)..(737)
<223> OTHER INFORMATION: n may be thymidine or uracil
<220> FEATURE:
<221> NAME/KEY: misc_feature
<222> LOCATION: (741)..(741)
<223> OTHER INFORMATION: n may be thymidine or uracil
<220> FEATURE:
<221> NAME/KEY: misc_feature
<222> LOCATION: (752)..(752)
<223> OTHER INFORMATION: n may be thymidine or uracil
<220> FEATURE:
<221> NAME/KEY: misc_feature
```

```
<222> LOCATION: (755)..(755)
<223> OTHER INFORMATION: n may be thymidine or uracil

<400> SEQUENCE: 9
cccgngccgc cggcnacagg anccaggcnc angcanccca ngcncaacan ngcngncaag      60
gcngcgcgcc gcgccggaca gancancaan cgcgcgnccc ncgancncga ccngancgag     120
anccgcaaga agcagcagaa cgacnncgnc accgaagngg acaaggccgc cgaagacgcg     180
ancancgaga cgcngaagac cgccnaccccc gaccacgcga nccncgcgga ggaancgggc    240
gaanccgaca acgaanccga anncaagngg ancancganc cgcncgacgg cacgaccaac    300
nncanccacg gcnncccgna nnacngcgna ncgancgcgc ncgagcacaa gggcgncgnc    360
acgcaggccg ncgncnacga nccgaacaag aacgaccngn ncacggccac ccgcggccgc    420
ggcgcanacc ngaacgaccg ccgcanccgc gncggccgcc gcgaccgcc ggcagacgca     480 cnggncggca cgggcnnccc gnnccgcgag aaggacggcc ncgacgccna cgcgcgccnc    540
nncaccgaaa ngacgcaggc cngcacgggc cngcgccgnc cgggcgcggc ggcgncgan    600 cncgcgaacg ncgcggccgg ccgccncgac gcgnncnncg agcaaggcan caacgngngg    660
gacanggcag cgggcagccn gcngancacc gaggccggcg gccncgncgg gaacnacacg    720
ggcgacgccg annnccngca ncgccacgag ancgncgccg cgaaccc                  767

<210> SEQ ID NO 10
<211> LENGTH: 11
<212> TYPE: DNA
<213> ORGANISM: Acinetobacter baumannii
<220> FEATURE:
<221> NAME/KEY: misc_feature
<222> LOCATION: (3)..(3)
<223> OTHER INFORMATION: n may be thymidine or uracil
<220> FEATURE:
<221> NAME/KEY: misc_feature
<222> LOCATION: (7)..(7)
<223> OTHER INFORMATION: n may be thymidine or uracil
<220> FEATURE:
<221> NAME/KEY: misc_feature
<222> LOCATION: (9)..(9)
<223> OTHER INFORMATION: n may be thymidine or uracil

<400> SEQUENCE: 10
canggananc c                                                          11

<210> SEQ ID NO 11
<211> LENGTH: 11
<212> TYPE: DNA
<213> ORGANISM: Escherichia coli
<220> FEATURE:
<221> NAME/KEY: misc_feature
<222> LOCATION: (2)..(2)
<223> OTHER INFORMATION: n may be thymidine or uracil
<220> FEATURE:
<221> NAME/KEY: misc_feature
<222> LOCATION: (4)..(4)
<223> OTHER INFORMATION: n may be thymidine or uracil
<220> FEATURE:
<221> NAME/KEY: misc_feature
<222> LOCATION: (10)..(10)
<223> OTHER INFORMATION: n may be thymidine or uracil

<400> SEQUENCE: 11
angnaaaccn c                                                          11

<210> SEQ ID NO 12
<211> LENGTH: 11
<212> TYPE: DNA
```

-continued

```
<213> ORGANISM: Escherichia coli
<220> FEATURE:
<221> NAME/KEY: misc_feature
<222> LOCATION: (2)..(3)
<223> OTHER INFORMATION: n may be thymidine or uracil
<220> FEATURE:
<221> NAME/KEY: misc_feature
<222> LOCATION: (6)..(6)
<223> OTHER INFORMATION: n may be thymidine or uracil
<220> FEATURE:
<221> NAME/KEY: misc_feature
<222> LOCATION: (8)..(8)
<223> OTHER INFORMATION: n may be thymidine or uracil
<220> FEATURE:
<221> NAME/KEY: misc_feature
<222> LOCATION: (10)..(10)
<223> OTHER INFORMATION: n may be thymidine or uracil

<400> SEQUENCE: 12
gnncanangn a                                                          11

<210> SEQ ID NO 13
<211> LENGTH: 11
<212> TYPE: DNA
<213> ORGANISM: Escherichia coli
<220> FEATURE:
<221> NAME/KEY: misc_feature
<222> LOCATION: (6)..(6)
<223> OTHER INFORMATION: n may be thymidine or uracil
<220> FEATURE:
<221> NAME/KEY: misc_feature
<222> LOCATION: (8)..(8)
<223> OTHER INFORMATION: n may be thymidine or uracil
<220> FEATURE:
<221> NAME/KEY: misc_feature
<222> LOCATION: (10)..(11)
<223> OTHER INFORMATION: n may be thymidine or uracil

<400> SEQUENCE: 13
aacccncngn n                                                          11

<210> SEQ ID NO 14
<211> LENGTH: 11
<212> TYPE: DNA
<213> ORGANISM: Escherichia coli
<220> FEATURE:
<221> NAME/KEY: misc_feature
<222> LOCATION: (1)..(1)
<223> OTHER INFORMATION: n may be thymidine or uracil
<220> FEATURE:
<221> NAME/KEY: misc_feature
<222> LOCATION: (3)..(4)
<223> OTHER INFORMATION: n may be thymidine or uracil
<220> FEATURE:
<221> NAME/KEY: misc_feature
<222> LOCATION: (7)..(7)
<223> OTHER INFORMATION: n may be thymidine or uracil
<220> FEATURE:
<221> NAME/KEY: misc_feature
<222> LOCATION: (9)..(9)
<223> OTHER INFORMATION: n may be thymidine or uracil
<220> FEATURE:
<221> NAME/KEY: misc_feature
<222> LOCATION: (11)..(11)
<223> OTHER INFORMATION: n may be thymidine or uracil

<400> SEQUENCE: 14
ngnncanang n                                                          11

<210> SEQ ID NO 15
<211> LENGTH: 11
<212> TYPE: DNA
<213> ORGANISM: Escherichia coli
```

```
<220> FEATURE:
<221> NAME/KEY: misc_feature
<222> LOCATION: (2)..(2)
<223> OTHER INFORMATION: n may be thymidine or uracil
<220> FEATURE:
<221> NAME/KEY: misc_feature
<222> LOCATION: (4)..(5)
<223> OTHER INFORMATION: n may be thymidine or uracil

<400> SEQUENCE: 15
gncnnaacgg c                                                        11

<210> SEQ ID NO 16
<211> LENGTH: 11
<212> TYPE: DNA
<213> ORGANISM: Escherichia coli
<220> FEATURE:
<221> NAME/KEY: misc_feature
<222> LOCATION: (6)..(6)
<223> OTHER INFORMATION: n may be thymidine or uracil
<220> FEATURE:
<221> NAME/KEY: misc_feature
<222> LOCATION: (8)..(8)
<223> OTHER INFORMATION: n may be thymidine or uracil
<220> FEATURE:
<221> NAME/KEY: misc_feature
<222> LOCATION: (10)..(11)
<223> OTHER INFORMATION: n may be thymidine or uracil

<400> SEQUENCE: 16
aggcangncn n                                                        11

<210> SEQ ID NO 17
<211> LENGTH: 11
<212> TYPE: DNA
<213> ORGANISM: Escherichia coli
<220> FEATURE:
<221> NAME/KEY: misc_feature
<222> LOCATION: (1)..(1)
<223> OTHER INFORMATION: n may be thymidine or uracil
<220> FEATURE:
<221> NAME/KEY: misc_feature
<222> LOCATION: (7)..(7)
<223> OTHER INFORMATION: n may be thymidine or uracil
<220> FEATURE:
<221> NAME/KEY: misc_feature
<222> LOCATION: (9)..(9)
<223> OTHER INFORMATION: n may be thymidine or uracil
<220> FEATURE:
<221> NAME/KEY: misc_feature
<222> LOCATION: (11)..(11)
<223> OTHER INFORMATION: n may be thymidine or uracil

<400> SEQUENCE: 17
naggcangnc n                                                        11

<210> SEQ ID NO 18
<211> LENGTH: 11
<212> TYPE: DNA
<213> ORGANISM: Escherichia coli
<220> FEATURE:
<221> NAME/KEY: misc_feature
<222> LOCATION: (1)..(1)
<223> OTHER INFORMATION: n may be thymidine or uracil
<220> FEATURE:
<221> NAME/KEY: misc_feature
<222> LOCATION: (3)..(3)
<223> OTHER INFORMATION: n may be thymidine or uracil
<220> FEATURE:
<221> NAME/KEY: misc_feature
<222> LOCATION: (5)..(6)
<223> OTHER INFORMATION: n may be thymidine or uracil
<220> FEATURE:
```

<221> NAME/KEY: misc_feature
<222> LOCATION: (9)..(9)
<223> OTHER INFORMATION: n may be thymidine or uracil

<400> SEQUENCE: 18
nangnncgng a                                                                           11

<210> SEQ ID NO 19
<211> LENGTH: 11
<212> TYPE: DNA
<213> ORGANISM: Escherichia coli
<220> FEATURE:
<221> NAME/KEY: misc_feature
<222> LOCATION: (1)..(2)
<223> OTHER INFORMATION: n may be thymidine or uracil
<220> FEATURE:
<221> NAME/KEY: misc_feature
<222> LOCATION: (5)..(7)
<223> OTHER INFORMATION: n may be thymidine or uracil
<220> FEATURE:
<221> NAME/KEY: misc_feature
<222> LOCATION: (11)..(11)
<223> OTHER INFORMATION: n may be thymidine or uracil

<400> SEQUENCE: 19
nncannngca n                                                                           11

<210> SEQ ID NO 20
<211> LENGTH: 11
<212> TYPE: DNA
<213> ORGANISM: Escherichia coli
<220> FEATURE:
<221> NAME/KEY: misc_feature
<222> LOCATION: (2)..(3)
<223> OTHER INFORMATION: n may be thymidine or uracil
<220> FEATURE:
<221> NAME/KEY: misc_feature
<222> LOCATION: (6)..(7)
<223> OTHER INFORMATION: n may be thymidine or uracil
<220> FEATURE:
<221> NAME/KEY: misc_feature
<222> LOCATION: (9)..(9)
<223> OTHER INFORMATION: n may be thymidine or uracil

<400> SEQUENCE: 20 anncenngng g                                                                           11

<210> SEQ ID NO 21
<211> LENGTH: 11
<212> TYPE: DNA
<213> ORGANISM: Escherichia coli
<220> FEATURE:
<221> NAME/KEY: misc_feature
<222> LOCATION: (1)..(3)
<223> OTHER INFORMATION: n may be thymidine or uracil
<220> FEATURE:
<221> NAME/KEY: misc_feature
<222> LOCATION: (7)..(8)
<223> OTHER INFORMATION: n may be thymidine or uracil
<220> FEATURE:
<221> NAME/KEY: misc_feature
<222> LOCATION: (11)..(11)
<223> OTHER INFORMATION: n may be thymidine or uracil

<400> SEQUENCE: 21
nnngcanncc n                                                                           11

<210> SEQ ID NO 22
<211> LENGTH: 11
<212> TYPE: DNA
<213> ORGANISM: Klebsiella pneumoniae

```
<220> FEATURE:
<221> NAME/KEY: misc_feature
<222> LOCATION: (3)..(3)
<223> OTHER INFORMATION: n may be thymidine or uracil
<220> FEATURE:
<221> NAME/KEY: misc_feature
<222> LOCATION: (8)..(8)
<223> OTHER INFORMATION: n may be thymidine or uracil

<400> SEQUENCE: 22
ganacagnga c                                                          11

<210> SEQ ID NO 23
<211> LENGTH: 11
<212> TYPE: DNA
<213> ORGANISM: Klebsiella pneumoniae
<220> FEATURE:
<221> NAME/KEY: misc_feature
<222> LOCATION: (6)..(6)
<223> OTHER INFORMATION: n may be thymidine or uracil
<220> FEATURE:
<221> NAME/KEY: misc_feature
<222> LOCATION: (8)..(9)
<223> OTHER INFORMATION: n may be thymidine or uracil

<400> SEQUENCE: 23
aacganannc c                                                          11

<210> SEQ ID NO 24
<211> LENGTH: 11
<212> TYPE: DNA
<213> ORGANISM: Escherichia coli
<220> FEATURE:
<221> NAME/KEY: misc_feature
<222> LOCATION: (1)..(1)
<223> OTHER INFORMATION: n may be thymidine or uracil
<220> FEATURE:
<221> NAME/KEY: misc_feature
<222> LOCATION: (6)..(9)
<223> OTHER INFORMATION: n may be thymidine or uracil

<400> SEQUENCE: 24
ncaagnnnnc c                                                          11

<210> SEQ ID NO 25
<211> LENGTH: 11
<212> TYPE: DNA
<213> ORGANISM: Escherichia coli
<220> FEATURE:
<221> NAME/KEY: misc_feature
<222> LOCATION: (1)..(1)
<223> OTHER INFORMATION: n may be thymidine or uracil
<220> FEATURE:
<221> NAME/KEY: misc_feature
<222> LOCATION: (4)..(7)
<223> OTHER INFORMATION: n may be thymidine or uracil
<220> FEATURE:
<221> NAME/KEY: misc_feature
<222> LOCATION: (9)..(10)
<223> OTHER INFORMATION: n may be thymidine or uracil

<400> SEQUENCE: 25
nccnnnnann c                                                          11

<210> SEQ ID NO 26
<211> LENGTH: 12
<212> TYPE: DNA
<213> ORGANISM: Acinetobacter baumannii
<220> FEATURE:
<221> NAME/KEY: misc_feature
<222> LOCATION: (1)..(2)
```

```
<223> OTHER INFORMATION: n may be thymidine or uracil
<220> FEATURE:
<221> NAME/KEY: misc_feature
<222> LOCATION: (4)..(4)
<223> OTHER INFORMATION: n may be thymidine or uracil
<220> FEATURE:
<221> NAME/KEY: misc_feature
<222> LOCATION: (6)..(7)
<223> OTHER INFORMATION: n may be thymidine or uracil
<220> FEATURE:
<221> NAME/KEY: misc_feature
<222> LOCATION: (10)..(10)
<223> OTHER INFORMATION: n may be thymidine or uracil

<400> SEQUENCE: 26
nnananncan gg                                                      12

<210> SEQ ID NO 27
<211> LENGTH: 11
<212> TYPE: DNA
<213> ORGANISM: Acinetobacter baumannii
<220> FEATURE:
<221> NAME/KEY: misc_feature
<222> LOCATION: (1)..(1)
<223> OTHER INFORMATION: n may be thymidine or uracil
<220> FEATURE:
<221> NAME/KEY: misc_feature
<222> LOCATION: (4)..(4)
<223> OTHER INFORMATION: n may be thymidine or uracil

<400> SEQUENCE: 27
ncanggcaaa g                                                       11

<210> SEQ ID NO 28
<211> LENGTH: 11
<212> TYPE: DNA
<213> ORGANISM: Acinetobacter baumannii
<220> FEATURE:
<221> NAME/KEY: misc_feature
<222> LOCATION: (1)..(3)
<223> OTHER INFORMATION: n may be thymidine or uracil
<220> FEATURE:
<221> NAME/KEY: misc_feature
<222> LOCATION: (6)..(6)
<223> OTHER INFORMATION: n may be thymidine or uracil
<220> FEATURE:
<221> NAME/KEY: misc_feature
<222> LOCATION: (8)..(8)
<223> OTHER INFORMATION: n may be thymidine or uracil

<400> SEQUENCE: 28
nnnccngnca a                                                       11

<210> SEQ ID NO 29
<211> LENGTH: 11
<212> TYPE: DNA
<213> ORGANISM: Acinetobacter baumannii
<220> FEATURE:
<221> NAME/KEY: misc_feature
<222> LOCATION: (1)..(2)
<223> OTHER INFORMATION: n may be thymidine or uracil
<220> FEATURE:
<221> NAME/KEY: misc_feature
<222> LOCATION: (10)..(10)
<223> OTHER INFORMATION: n may be thymidine or uracil

<400> SEQUENCE: 29
nngccaacan g                                                       11

<210> SEQ ID NO 30
<211> LENGTH: 11
```

```
<212> TYPE: DNA
<213> ORGANISM: Acinetobacter baumannii
<220> FEATURE:
<221> NAME/KEY: misc_feature
<222> LOCATION: (3)..(4)
<223> OTHER INFORMATION: n may be thymidine or uracil

<400> SEQUENCE: 30
cannacccaa g                                                            11

<210> SEQ ID NO 31
<211> LENGTH: 11
<212> TYPE: DNA
<213> ORGANISM: Acinetobacter baumannii
<220> FEATURE:
<221> NAME/KEY: misc_feature
<222> LOCATION: (1)..(2)
<223> OTHER INFORMATION: n may be thymidine or uracil
<220> FEATURE:
<221> NAME/KEY: misc_feature
<222> LOCATION: (7)..(7)
<223> OTHER INFORMATION: n may be thymidine or uracil
<220> FEATURE:
<221> NAME/KEY: misc_feature
<222> LOCATION: (11)..(11)
<223> OTHER INFORMATION: n may be thymidine or uracil

<400> SEQUENCE: 31
nnaaaancca n                                                            11

<210> SEQ ID NO 32
<211> LENGTH: 11
<212> TYPE: DNA
<213> ORGANISM: Pseudomonas aeruginosa
<220> FEATURE:
<221> NAME/KEY: misc_feature
<222> LOCATION: (1)..(1)
<223> OTHER INFORMATION: n may be thymidine or uracil
<220> FEATURE:
<221> NAME/KEY: misc_feature
<222> LOCATION: (7)..(7)
<223> OTHER INFORMATION: n may be thymidine or uracil

<400> SEQUENCE: 32
naggcancga c                                                            11

<210> SEQ ID NO 33
<211> LENGTH: 11
<212> TYPE: DNA
<213> ORGANISM: Pseudomonas aeruginosa
<220> FEATURE:
<221> NAME/KEY: misc_feature
<222> LOCATION: (6)..(6)
<223> OTHER INFORMATION: n may be thymidine or uracil
<220> FEATURE:
<221> NAME/KEY: misc_feature
<222> LOCATION: (9)..(9)
<223> OTHER INFORMATION: n may be thymidine or uracil
<220> FEATURE:
<221> NAME/KEY: misc_feature
<222> LOCATION: (11)..(11)
<223> OTHER INFORMATION: n may be thymidine or uracil

<400> SEQUENCE: 33
aaagcnccnc n                                                            11

<210> SEQ ID NO 34
<211> LENGTH: 11
<212> TYPE: DNA
<213> ORGANISM: Pseudomonas aeruginosa
<220> FEATURE:
```

<221> NAME/KEY: misc_feature
<222> LOCATION: (7)..(7)
<223> OTHER INFORMATION: n may be thymidine or uracil

<400> SEQUENCE: 34
aggccanagc g    11

<210> SEQ ID NO 35
<211> LENGTH: 11
<212> TYPE: DNA
<213> ORGANISM: Pseudomonas aeruginosa
<220> FEATURE:
<221> NAME/KEY: misc_feature
<222> LOCATION: (1)..(2)
<223> OTHER INFORMATION: n may be thymidine or uracil
<220> FEATURE:
<221> NAME/KEY: misc_feature
<222> LOCATION: (5)..(5)
<223> OTHER INFORMATION: n may be thymidine or uracil
<220> FEATURE:
<221> NAME/KEY: misc_feature
<222> LOCATION: (8)..(8)
<223> OTHER INFORMATION: n may be thymidine or uracil

<400> SEQUENCE: 35
nnacnccnga a    11

<210> SEQ ID NO 36
<211> LENGTH: 11
<212> TYPE: DNA
<213> ORGANISM: Pseudomonas aeruginosa
<220> FEATURE:
<221> NAME/KEY: misc_feature
<222> LOCATION: (1)..(2)
<223> OTHER INFORMATION: n may be thymidine or uracil
<220> FEATURE:
<221> NAME/KEY: misc_feature
<222> LOCATION: (6)..(6)
<223> OTHER INFORMATION: n may be thymidine or uracil
<220> FEATURE:
<221> NAME/KEY: misc_feature
<222> LOCATION: (9)..(9)
<223> OTHER INFORMATION: n may be thymidine or uracil
<220> FEATURE:
<221> NAME/KEY: misc_feature
<222> LOCATION: (11)..(11)
<223> OTHER INFORMATION: n may be thymidine or uracil

<400> SEQUENCE: 36
nncggncang n    11

<210> SEQ ID NO 37
<211> LENGTH: 11
<212> TYPE: DNA
<213> ORGANISM: Acinetobacter baumannii
<220> FEATURE:
<221> NAME/KEY: misc_feature
<222> LOCATION: (1)..(1)
<223> OTHER INFORMATION: n may be thymidine or uracil
<220> FEATURE:
<221> NAME/KEY: misc_feature
<222> LOCATION: (4)..(4)
<223> OTHER INFORMATION: n may be thymidine or uracil
<220> FEATURE:
<221> NAME/KEY: misc_feature
<222> LOCATION: (6)..(8)
<223> OTHER INFORMATION: n may be thymidine or uracil
<220> FEATURE:
<221> NAME/KEY: misc_feature
<222> LOCATION: (11)..(11)
<223> OTHER INFORMATION: n may be thymidine or uracil

<400> SEQUENCE: 37

```
ncancnnngc n                                                              11

<210> SEQ ID NO 38
<211> LENGTH: 11
<212> TYPE: DNA
<213> ORGANISM: Pseudomonas aeruginosa
<220> FEATURE:
<221> NAME/KEY: misc_feature
<222> LOCATION: (3)..(3)
<223> OTHER INFORMATION: n may be thymidine or uracil
<220> FEATURE:
<221> NAME/KEY: misc_feature
<222> LOCATION: (7)..(7)
<223> OTHER INFORMATION: n may be thymidine or uracil

<400> SEQUENCE: 38
agnaacncca c                                                              11

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43
<211> LENGTH: 12
<212> TYPE: PRT
<213> ORGANISM: Artificial Sequence
<220> FEATURE:
<223> OTHER INFORMATION: (RXR)4 Cell-Penetrating Peptide
<220> FEATURE:
<221> NAME/KEY: misc_feature
<222> LOCATION: (2)..(2)
<223> OTHER INFORMATION: Xaa may be 6-aminohexanoic acid
<220> FEATURE:
<221> NAME/KEY: misc_feature
<222> LOCATION: (5)..(5)
<223> OTHER INFORMATION: Xaa may be 6-aminohexanoic acid
<220> FEATURE:
<221> NAME/KEY: misc_feature
<222> LOCATION: (8)..(8)
<223> OTHER INFORMATION: Xaa may be 6-aminohexanoic acid
<220> FEATURE:
<221> NAME/KEY: misc_feature
<222> LOCATION: (11)..(11)
<223> OTHER INFORMATION: Xaa may be 6-aminohexanoic acid

<400> SEQUENCE: 43

Arg Xaa Arg Arg Xaa Arg Arg Xaa Arg Arg Xaa Arg
1               5                   10
```

```
<210> SEQ ID NO 44
<211> LENGTH: 10
<212> TYPE: PRT
<213> ORGANISM: Artificial Sequence
<220> FEATURE:
<223> OTHER INFORMATION: (RFF)3R Cell-Penetrating Peptide

<400> SEQUENCE: 44

Arg Phe Phe Arg Phe Phe Arg Phe Phe Arg
1               5                   10

<210> SEQ ID NO 45
<211> LENGTH: 14
<212> TYPE: PRT
<213> ORGANISM: Artificial Sequence
<220> FEATURE:
<223> OTHER INFORMATION: (RXR)4XB Cell-Penetrating Peptide
<220> FEATURE:
<221> NAME/KEY: misc_feature
<222> LOCATION: (2)..(2)
<223> OTHER INFORMATION: Xaa may be 6-aminohexanoic acid
<220> FEATURE:
<221> NAME/KEY: misc_feature
<222> LOCATION: (5)..(5)
<223> OTHER INFORMATION: Xaa may be 6-aminohexanoic acid
<220> FEATURE:
<221> NAME/KEY: misc_feature
<222> LOCATION: (8)..(8)
<223> OTHER INFORMATION: Xaa may be 6-aminohexanoic acid
<220> FEATURE:
<221> NAME/KEY: misc_feature
<222> LOCATION: (11)..(11)
<223> OTHER INFORMATION: Xaa may be 6-aminohexanoic acid
<220> FEATURE:
<221> NAME/KEY: misc_feature
<222> LOCATION: (13)..(13)
<223> OTHER INFORMATION: Xaa may be 6-aminohexanoic acid
<220> FEATURE:
<221> NAME/KEY: misc_feature
<222> LOCATION: (14)..(14)
<223> OTHER INFORMATION: Xaa may be beta-alanine

<400> SEQUENCE: 45

Arg Xaa Arg Arg Xaa Arg Arg Xaa Arg Arg Xaa Arg Xaa Xaa
1               5                   10

<210> SEQ ID NO 46
<211> LENGTH: 12
<212> TYPE: PRT
<213> ORGANISM: Artificial Sequence
<220> FEATURE:
<223> OTHER INFORMATION: (RFF)3RXB Cell-Penetrating Peptide
<220> FEATURE:
<221> NAME/KEY: misc_feature
<222> LOCATION: (11)..(11)
<223> OTHER INFORMATION: Xaa may be 6-aminohexanoic acid
<220> FEATURE:
<221> NAME/KEY: misc_feature
<222> LOCATION: (12)..(12)
<223> OTHER INFORMATION: Xaa may be beta-alanine

<400> SEQUENCE: 46

Arg Phe Phe Arg Phe Phe Arg Phe Phe Arg Xaa Xaa
1               5                   10
```

<210> SEQ ID NO 47
<211> LENGTH: 10
<212> TYPE: PRT
<213> ORGANISM: Artificial Sequence
<220> FEATURE:
<223> OTHER INFORMATION: (RFF)3RG Cell-Penetrating Peptide

<400> SEQUENCE: 47

Arg Phe Phe Arg Phe Phe Arg Phe Phe Arg
1               5                   10

<210> SEQ ID NO 48
<211> LENGTH: 7
<212> TYPE: PRT
<213> ORGANISM: Artificial Sequence
<220> FEATURE:
<223> OTHER INFORMATION: R6G Cell-Penetrating Peptide

<400> SEQUENCE: 48

Arg Arg Arg Arg Arg Arg Gly
1               5

<210> SEQ ID NO 49
<211> LENGTH: 6
<212> TYPE: PRT
<213> ORGANISM: artificial sequence
<220> FEATURE:
<223> OTHER INFORMATION: R6 Cell-Penetrating Peptide

<400> SEQUENCE: 49

Arg Arg Arg Arg Arg Arg
1               5

<210> SEQ ID NO 50
<211> LENGTH: 11
<212> TYPE: DNA
<213> ORGANISM: Escherichia coli
<220> FEATURE:
<221> NAME/KEY: misc_feature
<222> LOCATION: (6)..(7)
<223> OTHER INFORMATION: n may be thymidine or uracil
<220> FEATURE:
<221> NAME/KEY: misc_feature
<222> LOCATION: (11)..(11)
<223> OTHER INFORMATION: n may be thymidine or uracil

<400> SEQUENCE: 50
ggcaanncca n                                                    11

<210> SEQ ID NO 51
<211> LENGTH: 11
<212> TYPE: PRT
<213> ORGANISM: Artificial Sequence
<220> FEATURE:
<223> OTHER INFORMATION: Synthetic peptide

<400> SEQUENCE: 51

Arg Phe Phe Arg Phe Phe Arg Phe Phe Arg Gly
1               5                   10

UNITED STATES PATENT AND TRADEMARK OFFICE
CERTIFICATE OF CORRECTION

| | | |
|---|---|---|
| PATENT NO. | : 10,907,158 B2 | Page 1 of 1 |
| APPLICATION NO. | : 16/064273 | |
| DATED | : February 2, 2021 | |
| INVENTOR(S) | : David Greenberg et al. | |

It is certified that error appears in the above-identified patent and that said Letters Patent is hereby corrected as shown below:

In the Claims

In Claim 2, Column 116, Line 21, delete "steamy'" and insert --stearoyl-- therefor.

In Claim 11, Column 120, Line 16, delete "R" and insert --$R^a$-- therefor.

In Claim 13, Column 131, Line 3, delete "U" and insert --H-- therefor.

In Claim 14, Column 131, Line 21, delete "he" and insert --be-- therefor.

Signed and Sealed this
Eighth Day of June, 2021

Drew Hirshfeld
*Performing the Functions and Duties of the
Under Secretary of Commerce for Intellectual Property and
Director of the United States Patent and Trademark Office*